US006987211B1

(12) United States Patent
Soreq et al.

(10) Patent No.: US 6,987,211 B1
(45) Date of Patent: Jan. 17, 2006

(54) TRANSGENIC NON-HUMAN MAMMALS PRODUCING A CHOLINESTERASE IN THEIR MILK

(75) Inventors: Hermona Soreq, Jerusalem (IL); Haim Zakut, Savyon (IL); Moshe Shani, Hacabim (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/310,638

(22) Filed: May 12, 1999

Related U.S. Application Data

(63) Continuation-in-part of application No. 08/370,156, filed on Jan. 9, 1995, now Pat. No. 5,932,780, which is a continuation-in-part of application No. 08/202,755, filed on Feb. 28, 1994, now abandoned.

(51) Int. Cl.
*A01K 67/027* (2006.01)
*C12P 21/00* (2006.01)

(52) U.S. Cl. .............................. 800/14; 800/15; 800/16; 800/17; 800/18; 800/7

(58) Field of Classification Search ..................... 800/7, 800/13–20, 3, 8, 9
See application file for complete search history.

(56) References Cited

U.S. PATENT DOCUMENTS 4,736,866 A * 4/1988 Leder et al. ................... 800/10
5,932,780 A * 8/1999 Soreq et al. ................... 800/13

OTHER PUBLICATIONS

Verlander et al. High–Level Expression of Heterologous Protein in the Milk of Transgenic Swine Using the cDNA Encoding Human Protein C. Proc. Natl. Acad. Sci (USA). Dec. 1992, vol. 89, pp. 12003–12007.*
Kappell et al (1992) Current Opinion in Biotechnology 3, 548–553.*
Wall (1996) Theriogenology 45, 57–68.*
Houdebine (1994) Journal of Biotechnology 34, 269–287.*
Strojek and Wagner (1988) Genetic Engineering: Principles and Methods, vol. 10, Plenum Press, NY, pp 221–246.*
Mullins et al (1993) Hypertension 22, 630–633.*
Mullins et al (1996) J. Clin. Invest. 98, S37–S40.*
Bordbeck et al (1992) Mulitdisciplinary Approaches to Cholinesterase Functions, ed. Shafferman and Velan, Plenum Press, NY, 33–38).*
Liao et al (1992) J. Neurochem. 58, 1230–1238.*
Erb, C. et al. (2000) "Anticholinesterases Intensify the Stress–Induced Alternative Splicing of Acetylcholinesterase mRNA Through M1 Muscarinic Receptors", *Neuroscience Letters, Supplement 55, Abstracts of the 9th Meeting of The Israel Society for Neurosciences*: S16 (Exhibit 1).
Shoham, S. et al. (2000) "Transgenic Acetylcholinesterase Over–Expression Increases Weight Loss Response To Dietary Restriction", *Neuroscience Letters, Supplement 55, Abstracts of the 9th Meeting of The Israel Society for Neurosciences*: S16 (Exhibit 2) ; and.

Shohami, E. et al. (2000) "Antisense Prevention of Neuronal Damages Following Head Injury In Mice", *J. Mol. Med.* 78: 228–236 (Exhibit 3) .
Andres, C., Beeri, R., Friedman, A., Lev–Lehman, E., Henis, S., Timberg, R., Shami, M., Soreq, H. (1997). Acetylcholinesterase–transgenic mice display embryonic modulations in spinal cord choline acetyltransferase and neurexin I gene expression followed by late–onset neuromotor degeneration. Proc. Nat'l. Acad. Sci. USA 95, 8173–8178.
Beeri, R., Andres, C., Lev–Lehman, E., Timberg, R., Huberman, T., Shani M. and Soreq, H.. (1995). Transgenic expression of human acetylcholinesterase induces progressive cognitive deterioration in mice. Curr. Biol., 5, 1063–1071.
Beeri, R., LeNovere, N., Mervis, R., Huberman, T., Grauer, E. Changeux, J.P., and Soreq, H. (1997). Enhanced hemicholinium binding and attenuated dendrite branching in cognitively impaired ACHE–transgenic mice. J. Neurochem, 69, 2441–2451.
Maxwell, D.M., Brecht, K.M., Doctor, B.P., Wolfe, A.D. (1993). Comparison of antidote protection against soman by pyridostigmine, H1–6 and acetylcholinesterase. J. Pharmacol. Exp. Ther. I64, 1085–1089.
Raveh, L., Grauer, E., Grunwald, J., Cohen, E., Ashanai, Y. (1997). The stoichiometry of protection against soman and VX toxicity in monkeys pretreated with human butyrylcholinesterase. Toxicol. Appl. Pharmacol. I45, 43–53.
Seidman, S., Sternfeld, M., Ben Aziz–Aloya, R., Timberg, R., Kaufer–Nachum, D., Soreq, H. (1995). Synaptic and epidurmal accumulation of human acerylcholinesterase are encoded by alternative 3'–terminal exons. Mdol. Cell Biol. 15, 2993–3002.
Sternfeld, M., Ming, G–L., Song, H–J., Sela, K., Timberg, R., Poo, M–M, and Soreq, H. (1998). Acetylcholinesterase enhances neurite growth and synapse development through alternate contributions of its hydrolytic capacity, core protein and variable C–termini. J. Neurosci., 18, 1240–1249.
Wolfe, A.D., Blick, D.W., Murphy, M.R., Miller, S.A., Gentry, M.K. Hartgraves, S.L., Doctor, B.P. (1992). Use of cholinesterases as pretreatment drugs for the protection of rhesus monkeys against soman toxicity. Toxicol. Appl. Pharmacol. 117, 189–193.

* cited by examiner

*Primary Examiner*—Deborah Crouch
(74) *Attorney, Agent, or Firm*—John P. White, Esq.; Cooper & Dunham LLP

(57) ABSTRACT

The present invention relates to novel alternative forms of human acetylcholinesterase (AChE) and nucleotide sequences encoding the same. The genes encoding the novel forms of human AChE have been identified in various malignant tumor cells. In a further aspect, the invention relates to a transgenic animal assay system for evaluating efficacy of drugs against cholinergic proteins, prior to or in the course of therapeutic treatment. Transgenic animals, preferably developing tadpole of *Xenopus* or mice which express human AChE, are used. The transgenic animal assay system is also useful for evaluating the toxicity of substances which potentially block human AChE (e.g. organophosphorous compounds).

8 Claims, 45 Drawing Sheets

```
                        30                                    60
CCTCTCTCCC CTCATCTTTG CCAACCTGCC CCACCTCCTC TGCAGCTGAG CGATAACCCT 90                                   120
TGGGCCGACA GTGCCCTAAT CTCCTCCCTC CTGGCTTCTC GACCGACCCT TCACCCTTTC 150                                   180
CCTTTCTTTC TCCCAGCAGA CGCCGCCTGC CCTGCAGCCA TGAGGCCCCC GCAGTGTCTG 210                                   240
CTGCACACGC CTTCCCTGGC TTCCCCACTC CTTCTCCTCC TCCTCTGGCT CCTGGGTGGA 270                                   300
GGAGTGGGGG CTGAGGGCCG GGAGGATGCA GAGCTGCTGG TGACGGTGCG TGGGGGCCGG 330                                   360
CTGCGGGGCA TTCGCCTGAA GACCCCCGGG GGCCCTGTCT CTGCTTTCCT GGGCATCCCC 390                                   420
TTTGCGGAGC CACCCATGGG ACCCCGTCGC TTTCTGCCAC CGGAGCCCAA GCAGCCTTGG 450                                   480
TCAGGGGTGG TAGACGCTAC AACCTTCCAG AGTGTCTGCT ACCAATATGT GGACACCCTA 510                                   540
TACCCAGGTT TTGAGGGCAC CGAGATGTGG AACCCCAACC GTGAGCTGAG CGAGGACTGC 570                                   600
CTGTACCTCA ACGTGTGGAC ACCATACCCC CGGCCTACAT CCCCCACCCC TGTCCTCGTC 630                                   660
TGGATCTATG GGGGTGGCTT CTACAGTGGG GCCTCCTCCT TGGACGTGTA CGATGGCCGC 690                                   720
TTCTTGGTAC AGGCCGAGAG GACTGTGCTG GTGTCCATGA ACTACCGGGT GGGAGCCTTT 750                                   780
GGCTTCCTGG CCCTGCCGGG GAGCCGAGAG GCCCGGGCA ATGTGGGTCT CCTGGATCAG 810                                   840
AGGCTGGCCC TGCAGTGGGT GCAGGAGAAC GTGGCAGCCT TCGGGGGTGA CCCGACATCA 870                                   900
GTGACGCTGT TTGGGGAGAG CGCGGGAGCC GCCTCGGTGG CATGCACCT GCTGTCCCCG 930                                   960
CCCAGCCGGG GCCTGTTCCA CAGGGCCGTG CTGCAGAGCG GTGCCCCCAA TGGACCCTGG 990                                  1020
GCCACGGTGG GCATGGGAGA GGCCCGTCGC AGGGCCACGC AGCTGGCCCA CCTTGTGGGC
```

Fig-1a-1

```
                          1050                          1080
TGTCCTCCAG GCGGCACTGG TGGGAATGAC ACAGAGCTGG TAGCCTGCCT TCGGACACGA 1110                          1140
CCAGCGCAGG TCCTGGTGAA CCACGAATGG CACGTGCTGC CTCAAGAAAG CGTCTTCCGG 1170                          1200
TTCTCCTTCG TGCCTGTGGT AGATGGAGAC TTCCTCAGTG ACACCCCAGA GGCCCTCATC 1230                          1260
AACGCGGGAG ACTTCCACGG CCTGCAGGTG CTGGTGGGTG TGGTGAAGGA TGAGGGCTCG 1290                          1320
TATTTTCTGG TTTACGGGGC CCCAGGCTTC AGCAAAGACA ACGAGTCTCT CATCAGCCGG 1350                          1380
GCCGAGTTCC TGGCCGGGGT GCGGGTCGGG GTTCCCCAGG TAAGTGACCT GGCAGCCGAG 1410                          1440
GCTGTGGTCC TGCATTACAC AGACTGGCTG CATCCCGAGG ACCCGGCACG CCTGAGGGAG 1470                          1500
GCCCTGAGCG ATGTGGTGGG CGACCACAAT GTCGTGTGCC CCGTGGCCCA GCTGGCTGGG 1530                          1560
CGACTGGCTG CCCAGGGTGC CCGGGTCTAC GCCTACGTCT TTGAACACCG TGCTTCCACG 1590                          1620
CTCTCCTGGC CCCTGTGGAT GGGGGTGCCC CACGGCTACG AGATCGAGTT CATCTTTGGG 1650                          1680
ATCCCCCTGG ACCCCTCTCG AAACTACACG GCAGAGGAGA AAATCTTCGC CCAGCGACTG 1710                          1740
ATGCGATACT GGGCCAACTT TGCCCGCACA GGGGATCCCA ATGAGCCCCG AGACCCCAAG 1770                          1800
GCCCCACAAT GGCCCCCGTA CACGGCGGGG GCTCAGCAGT ACGTTAGTCT GGACCTGCGG 1830                          1860
CCGCTGGAGG TGCGGCGGGG GCTGCGCGCC CAGGCCTGCG CCTTCTGGAA CCGCTTCCTC 1890                          1920
CCCAAATTGC TCAGCGCCAC CGACACGCTC GACGAGGCGG AGCGCCAGTG GAAGGCCGAG 1950                          1980
TTCCACCGCT GGAGCTCCTA CATGGTGCAC TGGAAGAACC AGTTCGACCA CTACAGCAAG 2010                          2040
CAGGATCGCT GCTCAGACCT GTGACCCCGG CGGGACCCCC ATGTCCTCCG CTCCGCCCGG
```

Fig-1a-2

```
                    2070                                         2100
CCCCCTAGCT GTATATACTA TTTATTTCAG GGCTGGGCTA TAACACAGAC GAGCCCCAGA 2130                                         2160
CTCTGCCCAT CCCCACCCCA CCCCGACGTC CCCCGGGGCT CCCGGTCCTC TGGCATGTCT 2190                                         2220
TCAGGCTGAG CTCCTCCCCG CGTGCCTTCG CCCTCTGGCT GCAAATAAAC TGTTACAGGC

2250
CAAAAAAAAA AAAAAAAAAA AAAAAAAAAA AAAAAA
```

```
        CCT CTC TCC CCT CAT CTT TGC CAA CCT GCC

CCA CCT CCT CTG CAG CTG AGC GAT AAC CCT           60

TGG GCC GAC AGT GCC CTA ATC TCC TCC CTC

CTG GCT TCT CGA CCG ACC CTT CAC CCT TTC          120

CCT TTC TTT CTC CCA GCA GAC GCC GCC TGC

CCT GCA GCC |ATG| AGG CCC CCG CAG TGT CTG        180
                    | M | R   P   P   Q   C   L

CTG CAC ACG CCT TCC CTG GCT TCC CCA CTC
         L   H   T   P   S   L   A   S   P   L

CTT CTC CTC CTC CTC TGG CTC CTG GGT GGA          240
         L   L   L   L   L   W   L   L   G   G

GGA GTG GGG GCT GAG GGC CGG GAG GAT GCA
         G   V   G   A   E   G   R   E   D   A

GAG CTG CTG GTG ACG GTG CGT GGG GGC CGG          300
         E   L   L   V   T   V   R   G   G   R

CTG CGG GGC ATT CGC CTG AAG ACC CCC GGG
         L   R   G   I   R   L   K   T   P   G

GGC CCT GTC TCT GCT TTC CTG GGC ATC CCC          360
         G   P   V   S   A   F   L   G   I   P

TTT GCG GAG CCA CCC ATG GGA CCC CGT CGC
         F   A   E   P   P   M   G   P   R   R

TTT CTG CCA CCG GAG CCC AAG CAG CCT TGG          420
         F   L   P   P   E   P   K   Q   P   W

TCA GGG GTG GTA GAC GCT ACA ACC TTC CAG
         S   G   V   V   D   A   T   T   F   Q

AGT GTC TGC TAC CAA TAT GTG GAC ACC CTA          480
         S   V   C   Y   Q   Y   V   D   T   L

TAC CCA GGT TTT GAG GGC ACC GAG ATG TGG
         Y   P   G   F   E   G   T   E   M   W

AAC CCC AAC CGT GAG CTG AGC GAG GAC TGC          540
         N   P   N   R   E   L   S   E   D   C

CTG TAC CTC AAC GTG TGG ACA CCA TAC CCC
         L   Y   L   N   V   W   T   P   Y   P

CGG CCT ACA TCC CCC ACC CCT GTC CTC GTC          600
         R   P   T   S   P   T   P   V   L   V
```

Fig-1c-1

```
TGG ATC TAT GGG GGT GGC TTC TAC AGT GGG
 W   I   Y   G   G   G   F   Y   S   G

GCC TCC TCC TTG GAC GTG TAC GAT GGC CGC      660
 A   S   S   L   D   V   Y   D   G   R

TTC TTG GTA CAG GCC GAG AGG ACT GTG CTG
 F   L   V   Q   A   E   R   T   V   L

GTG TCC ATG AAC TAC CGG GTG GGA GCC TTT      720
 V   S   M   N   Y   R   V   G   A   F

GGC TTC CTG GCC CTG CCG GGG AGC CGA GAG
 G   F   L   A   L   P   G   S   R   E

GCC CCG GGC AAT GTG GGT CTC CTG GAT CAG      780
 A   P   G   N   V   G   L   L   D   Q

AGG CTG GCC CTG CAG TGG GTG CAG GAG AAC
 R   L   A   L   Q   W   V   Q   E   N

GTG GCA GCC TTC GGG GGT GAC CCG ACA TCA      840
 V   A   A   F   G   G   D   P   T   S

GTG ACG CTG TTT GGG GAG AGC GCG GGA GCC
 V   T   L   F   G   E   S   A   G   A

GCC TCG GTG GGC ATG CAC CTG CTG TCC CCG      900
 A   S   V   G   M   H   L   L   S   P

CCC AGC CGG GGC CTG TTC CAC AGG GCC GTG
 P   S   R   G   L   F   H   R   A   V

CTG CAG AGC GGT GCC CCC AAT GGA CCC TGG      960
 L   Q   S   G   A   P   N   G   P   W

GCC ACG GTG GGC ATG GGA GAG GCC CGT CGC
 A   T   V   G   M   G   E   A   R   R

AGG GCC ACG CAG CTG GCC CAC CTT GTG GGC     1020
 R   A   T   Q   L   A   H   L   V   G

TGT CCT CCA GGC GGC ACT GGT GGG AAT GAC
 C   P   P   G   G   T   G   G   N   D

ACA GAG CTG GTA GCC TGC CTT CGG ACA CGA     1080
 T   E   L   V   A   C   L   R   T   R

CCA GCG CAG GTC CTG GTG AAC CAC GAA TGG
 P   A   Q   V   L   V   N   H   E   W

CAC GTG CTG CCT CAA GAA AGC GTC TTC CGG     1140
 H   V   L   P   Q   E   S   V   F   R
```

Fig-1c-2

```
TTC TCC TTC GTG CCT GTG GTA GAT GGA GAC
 F   S   F   V   P   V   V   D   G   D

TTC CTC AGT GAC ACC CCA GAG GCC CTC ATC        1200
 F   L   S   D   T   P   E   A   L   I

AAC GCG GGA GAC TTC CAC GGC CTG CAG GTG
 N   A   G   D   F   H   G   L   Q   V

CTG GTG GGT GTG GTG AAG GAT GAG GGC TCG        1260
 L   V   G   V   V   K   D   E   G   S

TAT TTT CTG GTT TAC GGG GCC CCA GGC TTC
 Y   F   L   V   Y   G   A   P   G   F

AGC AAA GAC AAC GAG TCT CTC ATC AGC CGG        1320
 S   K   D   N   E   S   L   I   S   R

GCC GAG TTC CTG GCC GGG GTG CGG GTC GGG
 A   E   F   L   A   G   V   R   V   G

GTT CCC CAG GTA AGT GAC CTG GCA GCC GAG        1380
 V   P   Q   V   S   D   L   A   A   E

GCT GTG GTC CTG CAT TAC ACA GAC TGG CTG
 A   V   V   L   H   Y   T   D   W   L

CAT CCC GAG GAC CCG GCA CGC CTG AGG GAG        1440
 H   P   E   D   P   A   R   L   R   E

GCC CTG AGC GAT GTG GTG GGC GAC CAC AAT
 A   L   S   D   V   V   G   D   H   N

GTC GTG TGC CCC GTG GCC CAG CTG GCT GGG        1500
 V   V   C   P   V   A   Q   L   A   G

CGA CTG GCT GCC CAG GGT GCC CGG GTC TAC
 R   L   A   A   Q   G   A   R   V   Y

GCC TAC GTC TTT GAA CAC CGT GCT TCC ACG        1560
 A   Y   V   F   E   H   R   A   S   T

CTC TCC TGG CCC CTG TGG ATG GGG GTG CCC
 L   S   W   P   L   W   M   G   V   P

CAC GGC TAC GAG ATC GAG TTC ATC TTT GGG        1620
 H   G   Y   E   I   E   F   I   F   G

ATC CCC CTG GAC CCC TCT CGA AAC TAC ACG
 I   P   L   D   P   S   R   N   Y   T

GCA GAG GAG AAA ATC TTC GCC CAG CGA CTG        1680
 A   E   E   K   I   F   A   Q   R   L
```

Fig-1c-3

```
ATG CGA TAC TGG GCC AAC TTT GCC CGC ACA
 M   R   Y   W   A   N   F   A   R   T

GGG GAT CCC AAT GAG CCC CGA GAC CCC AAG        1740
 G   D   P   N   E   P   R   D   P   K

GCC CCA CAA TGG CCC CCG TAC ACG GCG GGG
 A   P   Q   W   P   P   Y   T   A   G

GCT CAG CAG TAC GTT AGT CTG GAC CTG CGG        1800
 A   Q   Q   Y   V   S   L   D   L   R

CCG CTG GAG GTG CGG CGG GGG CTG CGC GCC
 P   L   E   V   R   R   G   L   R   A

CAG GCC TGC GCC TTC TGG AAC CGC TTC CTC        1860
 Q   A   C   A   F   W   N   R   F   L

CCC AAA TTG CTC AGC GCC ACC GGT ATG CAG
 P   K   L   L   S   A   T   G   M   Q

GGG CCA GCG GGC AGC GCT GGG AGG AGG GGA        1920
 G   P   A   G   S   A   G   R   R   G

GTG GGA GCC CGC CAG TGT AAC CCC TCT CTT
 V   G   A   R   Q   C   N   P   S   L

CTC CCC CTA GCC TCG GAG GCT CCC AGC ACC        1980
 L   P   L   A   S   E   A   P   S   T

TGC CCA GGC TTC ACC CAT GGG GAG GCT GCT
 C   P   G   F   T   H   G   E   A   A

CCG AGG CCC GGC CTC CCC CTG CCC CTC CTC        2040
 P   R   P   G   L   P   L   P   L   L

CTC CTC CAC CAG CTT CTC CTC CTC TTC CTC
 L   L   H   Q   L   L   L   L   F   L

TCC CAC CTC CGG CGG CTG TGA ACA CGG CCT        2100
 S   H   L   R   R   L

CTT CCC CTA CGG CCT ACA GGG GCC CCT CCT

CTA ATG AGT GGT AGG ACC TGT GGG GAA GGG        2160

CCC CAC TCA GGG ATC TCA GAC CTA GTG CTC

CCT TCC TCC TCA AAC CGA GAG ACT CAC ACT        2220

GGA CAG GGC AGG AGG AGG GGC CGT GCC TCC

CAC CCT TCT CAG GGA CCC CCA CGC CTT TGT        2280
```

Fig-1c-4

```
TGT TTG AAT GGA AAT GGA AAA GCC AGT ATT
CTT TTA TAA AAT TAT CTT TTG GAA CCT GAG         2340
CCT GAC ATT GGG GGA AGT GGA GGC CCG AAA
ACG GGG TAG CAC CCC CAT TGG GGC TAT AAC         2400
GGT CAA CCA TTT CTG TCT CTT CTT TTT CCC
CCA ACC TCC CCC TCC TGT CCC CTC TGT TCC         2460
CGT CTT CCG GTC ATT CTT TTC TCC TCC TCT
CTC CTT CCT GCT GTC CTT CTC GGC CCC GCC         2520
TCT GCC CTC ATC CTC CCT CTC GTC TTT CGC
ACA TTC TCC TGA TCC TCT TGC CAC CGT CCC         2580
ACG TGG TCG CCT GCA TTT CTC CGT GCG TCC
TCC CTG CAC TCA TAC CCC CCC TTC AAC CCG         2640
CCC AAA TGT CCG ATC CCC GAC CTT CCT CGT
GCC GTC CTC CCC TCC CGC CTC GCT GGG CGC         2700
CCT GGC CGC AGA CAC GCT CGA CAC GCT CGA
CGA GGC GGA GCG CCA GTG GAA GGC CGA GTT         2760
CCA CCG CTG GAG CTC CTA CAT GGT GCA CTG
GAA GAA CCA GTT CGA CCA CTA CAG CAA GCA         2820
GGA TCG CTG CTC AGA CCT GTG ACC CCG GCG
GGA CCC CCA TGT CCT CCG CTC CGC CCG GCC         2880
CCC TAG CTG TAT ATA CTA TTT ATT TCA GGG
CTG GGC TAT AAC ACA GAC GAG CCC CAG ACT         2940
CTG CCC ATC CCC ACC CCA CCC CGA CGT CCC
CCG GGC TCC CCG GTC CTC TGG CAT GTC TTC         3000
AGG CTG AGC TCC TCC CCG CGT GCC TTC GCC
CTC TGG CTG CAA ATA AAC TGT TAC AGG CCA         3060
AAA AAA AAA AAA AAA AAA AAA AAA AAA AAA AAA A
```

Fig-1c-5

```
CCT CTC TCC CCT CAT CTT TGC CAA CCT GCC
CCA CCT CCT CTG CAG CTG AGC GAT AAC CCT        60
TGG GCC GAC AGT GCC CTA ATC TCC TCC CTC
CTG GCT TCT CGA CCG ACC CTT CAC CCT TTC       120
CCT TTC TTT CTC CCA GCA GAC GCC GCC TGC
CCT GCA GCC ATG AGG CCC CCG CAG TGT CTG       180
             M   R   P   P   Q   C   L
CTG CAC ACG CCT TCC CTG GCT TCC CCA CTC
 L   H   T   P   S   L   A   S   P   L
CTT CTC CTC CTC CTC TGG CTC CTG GGT GGA       240
 L   L   L   L   L   W   L   L   G   G
GGA GTG GGG GCT GAG GGC CGG GAG GAT GCA
 G   V   G   A   E   G   R   E   D   A
GAG CTG CTG GTG ACG GTG CGT GGG GGC CGG       300
 E   L   L   V   T   V   R   G   G   R
CTG CGG GGC ATT CGC CTG AAG ACC CCC GGG
 L   R   G   I   R   L   K   T   P   G
GGC CCT GTC TCT GCT TTC CTG GGC ATC CCC       360
 G   P   V   S   A   F   L   G   I   P
TTT GCG GAG CCA CCC ATG GGA CCC CGT CGC
 F   A   E   P   P   M   G   P   R   R
TTT CTG CCA CCG GAG CCC AAG CAG CCT TGG       420
 F   L   P   P   E   P   K   Q   P   W
TCA GGG GTG GTA GAC GCT ACA ACC TTC CAG
 S   G   V   V   D   A   T   T   F   Q
AGT GTC TGC TAC CAA TAT GTG GAC ACC CTA       480
 S   V   C   Y   Q   Y   V   D   T   L
TAC CCA GGT TTT GAG GGC ACC GAG ATG TGG
 Y   P   G   F   E   G   T   E   M   W
AAC CCC AAC CGT GAG CTG AGC GAG GAC TGC       540
 N   P   N   R   E   L   S   E   D   C
```

Fig-1d-1

```
CTG TAC CTC AAC GTG TGG ACA CCA TAC CCC
 L   Y   L   N   V   W   T   P   Y   P

CGG CCT ACA TCC CCC ACC CCT GTC CTC GTC         600
 R   P   T   S   P   T   P   V   L   V

TGG ATC TAT GGG GGT GGC TTC TAC AGT GGG
 W   I   Y   G   G   G   F   Y   S   G

GCC TCC TCC TTG GAC GTG TAC GAT GGC CGC         660
 A   S   S   L   D   V   Y   D   G   R

TTC TTG GTA CAG GCC GAG AGG ACT GTG CTG
 F   L   V   Q   A   E   R   T   V   L

GTG TCC ATG AAC TAC CGG GTG GGA GCC TTT         720
 V   S   M   N   Y   R   V   G   A   F

GGC TTC CTG GCC CTG CCG GGG AGC CGA GAG
 G   F   L   A   L   P   G   S   R   E

GCC CCG GGC AAT GTG GGT CTC CTG GAT CAG         780
 A   P   G   N   V   G   L   L   D   Q

AGG CTG GCC CTG CAG TGG GTG CAG GAG AAC
 R   L   A   L   Q   W   V   Q   E   N

GTG GCA GCC TTC GGG GGT GAC CCG ACA TCA         840
 V   A   A   F   G   G   D   P   T   S

GTG ACG CTG TTT GGG GAG AGC GCG GGA GCC
 V   T   L   F   G   E   S   A   G   A

GCC TCG GTG GGC ATG CAC CTG CTG TCC CCG         900
 A   S   V   G   M   H   L   L   S   P

CCC AGC CGG GGC CTG TTC CAC AGG GCC GTG
 P   S   R   G   L   F   H   R   A   V

CTG CAG AGC GGT GCC CCC AAT GGA CCC TGG         960
 L   Q   S   G   A   P   N   G   P   W

GCC ACG GTG GGC ATG GGA GAG GCC CGT CGC
 A   T   V   G   M   G   E   A   R   R

AGG GCC ACG CAG CTG GCC CAC CTT GTG GGC        1020
 R   A   T   Q   L   A   H   L   V   G

TGT CCT CCA GGC GGC ACT GGT GGG AAT GAC
 C   P   P   G   G   T   G   G   N   D
```

Fig-1d-2

```
ACA GAG CTG GTA GCC TGC CTT CGG ACA CGA        1080
 T   E   L   V   A   C   L   R   T   R

CCA GCG CAG GTC CTG GTG AAC CAC GAA TGG
 P   A   Q   V   L   V   N   H   E   W

CAC GTG CTG CCT CAA GAA AGC GTC TTC CGG        1140
 H   V   L   P   Q   E   S   V   F   R

TTC TCC TTC GTG CCT GTG GTA GAT GGA GAC
 F   S   F   V   P   V   V   D   G   D

TTC CTC AGT GAC ACC CCA GAG GCC CTC ATC        1200
 F   L   S   D   T   P   E   A   L   I

AAC GCG GGA GAC TTC CAC GGC CTG CAG GTG
 N   A   G   D   F   H   G   L   Q   V

CTG GTG GGT GTG GTG AAG GAT GAG GGC TCG        1260
 L   V   G   V   V   K   D   E   G   S

TAT TTT CTG GTT TAC GGG GCC CCA GGC TTC
 Y   F   L   V   Y   G   A   P   G   F

AGC AAA GAC AAC GAG TCT CTC ATC AGC CGG        1320
 S   K   D   N   E   S   L   I   S   R

GCC GAG TTC CTG GCC GGG GTG CGG GTC GGG
 A   E   F   L   A   G   V   R   V   G

GTT CCC CAG GTA AGT GAC CTG GCA GCC GAG        1380
 V   P   Q   V   S   D   L   A   A   E

GCT GTG GTC CTG CAT TAC ACA GAC TGG CTG
 A   V   V   L   H   Y   T   D   W   L

CAT CCC GAG GAC CCG GCA CGC CTG AGG GAG        1440
 H   P   E   D   P   A   R   L   R   E

GCC CTG AGC GAT GTG GTG GGC GAC CAC AAT
 A   L   S   D   V   V   G   D   H   N

GTC GTG TGC CCC GTG GCC CAG CTG GCT GGG        1500
 V   V   C   P   V   A   Q   L   A   G

CGA CTG GCT GCC CAG GGT GCC CGG GTC TAC
 R   L   A   A   Q   G   A   R   V   Y

GCC TAC GTC TTT GAA CAC CGT GCT TCC ACG        1560
 A   Y   V   F   E   H   R   A   S   T
```

Fig-1d-3

```
CTC TCC TGG CCC CTG TGG ATG GGG GTG CCC
 L   S   W   P   L   W   M   G   V   P

CAC GGC TAC GAG ATC GAG TTC ATC TTT GGG         1620
 H   G   Y   E   I   E   F   I   F   G

ATC CCC CTG GAC CCC TCT CGA AAC TAC ACG
 I   P   L   D   P   S   R   N   Y   T

GCA GAG GAG AAA ATC TTC GCC CAG CGA CTG         1680
 A   E   E   K   I   F   A   Q   R   L

ATG CGA TAC TGG GCC AAC TTT GCC CGC ACA
 M   R   Y   W   A   N   F   A   R   T

GGG GAT CCC AAT GAG CCC CGA GAC CCC AAG         1740
 G   D   P   N   E   P   R   D   P   K

GCC CCA CAA TGG CCC CCG TAC ACG GCG GGG
 A   P   Q   W   P   P   Y   T   A   G

GCT CAG CAG TAC GTT AGT CTG GAC CTG CGG         1800
 A   Q   Q   Y   V   S   L   D   L   R

CCG CTG GAG GTG CGG CGG GGG CTG CGC GCC
 P   L   E   V   R   R   G   L   R   A

CAG GCC TGC GCC TTC TGG AAC CGC TTC CTC         1860
 Q   A   C   A   F   W   N   R   F   L

CCC AAA TTG CTC AGC GCC ACC GCC TCG GAG
 P   K   L   L   S   A   T   A   S   E

GCT CCC AGC ACC TGC CCA GGC TTC ACC CAT         1920
 A   P   S   T   C   P   G   F   T   H

GGG GAG GCT GCT CCG AGG CCC GGC CTC CCC
 G   E   A   A   P   R   P   G   L   P

CTG CCC CTC CTC CTC CTC CAC CAG CTT CTC         1980
 L   P   L   L   L   L   H   Q   L   L

CTC CTC TTC CTC TCC CAC CTC CGG CGG CTG
 L   L   F   L   S   H   L   R   R

TGA ACA CGG CCT CTT CCC CTA CGG CCT ACA         2040

GGG GCC CCT CCT CTA ATG AGT GGT AGG ACC

TGT GGG GAA GGG CCC CAC TCA GGG ATC TCA         2100
```

Fig-1d-4

```
GAC CTA GTG CTC CCT TCC TCC TCA AAC CGA
GAG ACT CAC ACT GGA CAG GGC AGG AGG AGG         2160
GGC CGT GCC TCC CAC CCT TCT CAG GGA CCC
CCA CGC CTT TGT TGT TTG AAT GGA AAT GGA         2220
AAA GCC AGT ATT CTT TTA TAA AAT TAT CTT
TTG GAA CCT GAG CCT GAC ATT GGG GGA AGT         2280
GGA GGC CCG GAA ACG GGG TAG CAC CCC CAT
TGG GGC TAT AAC GGT CAA CCA TTT CTG TCT         2340
CTT CTT TTT CCC CCA ACC TCC CCC TCC TGT
CCC CTC TGT TCC CGT CTT CCG GTC ATT CTT         2400
TTC TCC TCC TCT CTC CTT CCT GCT GTC CTT
CTC GGC CCC GCC TCT GCC CTC ATC CTC CCT         2460
CTC GTC TTT CGC ACA TTC TCC TGA TCC TCT
TGC CAC CGT CCC ACG TGG TCG CCT GCA TTT         2520
CTC CGT GCG TCC TCC CTG CAC TCA TAC CCC
CCC TTC AAC CCG CCC AAA TGT CCG ATC CCC         2580
GAC CTT CCT CGT GCC GTC CTC CCC TCC CGC
CTC GCT GGG CGC CCT GGC CGC AGA CAC GCT         2640
CGA CAC GCT CGA CGA GGC GGA GCG CCA GTG
GAA GGC CGA GTT CCA CCG CTG GAG CTC CTA         2700
CAT GGT GCA CTG GAA GAA CCA GTT CGA CCA
CTA CAG CAA GCA GGA TCG CTG CTC AGA CCT         2760
GTG ACC CCG GCG GGA CCC CCA TGT CCT CCG
CTC CGC CCG GCC CCC TAG CTG TAT ATA CTA         2820
TTT ATT TCA GGG CTG GGC TAT AAC ACA GAC
```

Fig-1d-5

```
GAG CCC CAG ACT CTG CCC ATC CCC ACC CCA        2880
CCC CGA CGT CCC CCG GGG CTC CCG GTC CTC
TGG CAT GTC TTC AGG CTG AGC TCC TCC CCG        2940
CGT GCC TTC GCC CTC TGG CTG CAA ATA AAC
TGT TAC AGG CCA AAA AAA AAA AAA AAA AAA        3000
AAA AAA AAA AAA AAA A
```

Fig-1d-6

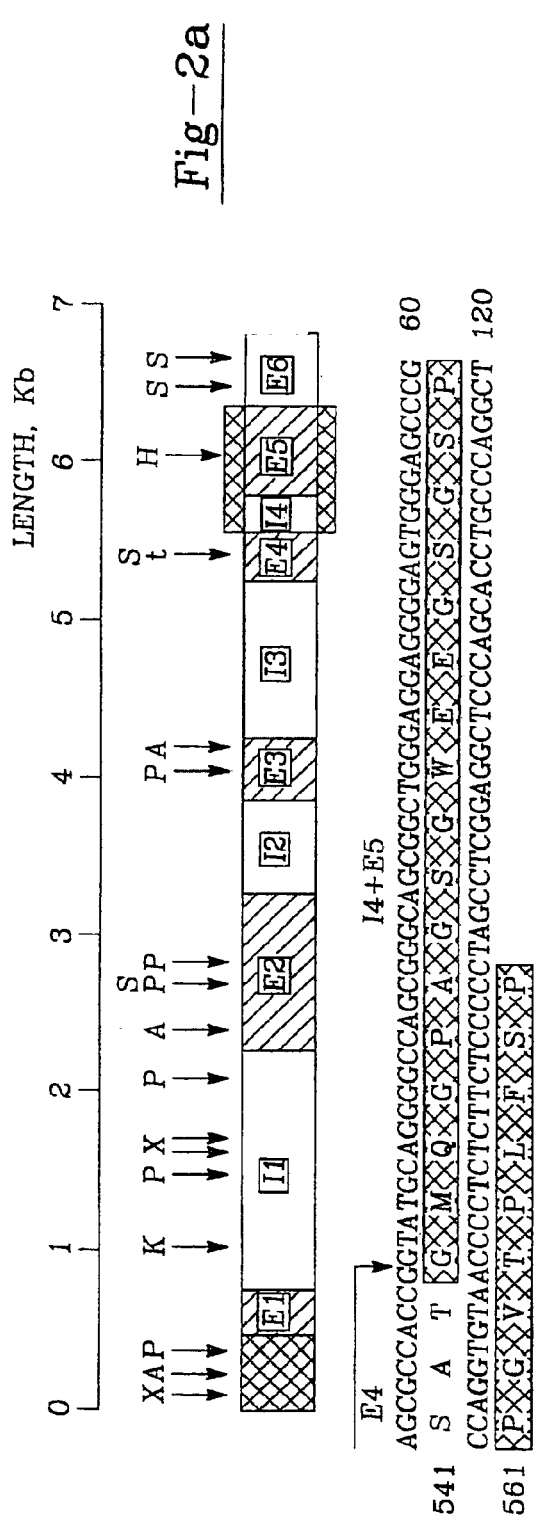

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
       (A) LENGTH: 2256 base pairs
       (B) TYPE: nucleic acid
       (C) STRANDEDNESS: single
       (D) TOPOLOGY: linear (xi) SEQUENCE DESCRIPTION: SEQ ID NO: 1:

```
CCTCTCTCCC CTCATCTTTG CCAACCTGCC CCACCTCCTC TGCAGCTGAG CGATAACCCT      60

TGGGCCGACA GTGCCCTAAT CTCCTCCCTC CTGGCTTCTC GACCGACCCT TCACCCTTTC     120

CCTTTCTTTC TCCCAGCAGA CGCCGCCTGC CCTGCAGCCA TGAGGCCCCC GCAGTGTCTG     180

CTGCACACGC CTTCCCTGGC TTCCCCACTC CTTCTCCTCC TCCTCTGGCT CCTGGGTGGA     240

GGAGTGGGGG CTGAGGGCCG GGAGGATGCA GAGCTGCTGG TGACGGTGCG TGGGGGCCGG     300

CTGCGGGGCA TTCGCCTGAA GACCCCCGGG GGCCCTGTCT CTGCTTTCCT GGGCATCCCC     360

TTTGCGGAGC CACCCATGGG ACCCCGTCGC TTTCTGCCAC CGGAGCCCAA GCAGCCTTGG     420

TCAGGGGTGG TAGACGCTAC AACCTTCCAG AGTGTCTGCT ACCAATATGT GGACACCCTA     480

TACCCAGGTT TTGAGGGCAC CGAGATGTGG AACCCCAACC GTGAGCTGAG CGAGGACTGC     540

CTGTACCTCA ACGTGTGGAC ACCATACCCC CGGCCTACAT CCCCCACCCC TGTCCTCGTC     600

TGGATCTATG GGGGTGGCTT CTACAGTGGG GCCTCCTCCT TGGACGTGTA CGATGGCCGC     660

TTCTTGGTAC AGGCCGAGAG GACTGTGCTG GTGTCCATGA ACTACCGGGT GGGAGCCTTT     720

GGCTTCCTGG CCCTGCCGGG GAGCCGAGAG GCCCCGGGCA ATGTGGGTCT CCTGGATCAG     780

AGGCTGGCCC TGCAGTGGGT GCAGGAGAAC GTGGCAGCCT TCGGGGGTGA CCCGACATCA     840

GTGACGCTGT TTGGGGAGAG CGCGGGAGCC GCCTCGGTGG GCATGCACCT GCTGTCCCCG     900

CCCAGCCGGG GCCTGTTCCA CAGGGCCGTG CTGCAGAGCG GTGCCCCCAA TGGACCCTGG     960

GCCACGGTGG GCATGGGAGA GGCCCGTCGC AGGGCCACGC AGCTGGCCCA CCTTGTGGGC    1020

TGTCCTCCAG GCGGCACTGG TGGGAATGAC ACAGAGCTGG TAGCCTGCCT TCGGACACGA    1080

CCAGCGCAGG TCCTGGTGAA CCACGAATGG CACGTGCTGC CTCAAGAAAG CGTCTTCCGG    1140

TTCTCCTTCG TGCCTGTGGT AGATGGAGAC TTCCTCAGTG ACACCCCAGA GGCCCTCATC    1200

AACGCGGGAG ACTTCCACGG CCTGCAGGTG CTGGTGGGTG TGGTGAAGGA TGAGGGCTCG    1260

TATTTTCTGG TTTACGGGGC CCCAGGCTTC AGCAAAGACA ACGAGTCTCT CATCAGCCGG    1320

GCCGAGTTCC TGGCCGGGGT GCGGGTCGGG GTTCCCCAGG TAAGTGACCT GGCAGCCGAG    1380

GCTGTGGTCC TGCATTACAC AGACTGGCTG CATCCCGAGG ACCCGGCACG CCTGAGGGAG    1440

GCCCTGAGCG ATGTGGTGGG CGACCACAAT GTCGTGTGCC CCGTGGCCCA GCTGGCTGGG    1500

CGACTGGCTG CCCAGGGTGC CCGGGTCTAC GCCTACGTCT TTGAACACCG TGCTTCCACG    1560

CTCTCCTGGC CCCTGTGGAT GGGGGTGCCC CACGGCTACG AGATCGAGTT CATCTTTGGG    1620

ATCCCCCTGG ACCCCTCTCG AAACTACACG GCAGAGGAGA AAATCTTCGC CCAGCGACTG    1680

ATGCGATACT GGGCCAACTT TGCCCGCACA GGGGATCCCA ATGAGCCCCG AGACCCCAAG    1740

GCCCCACAAT GGCCCCCGTA CACGGCGGGG GCTCAGCAGT ACGTTAGTCT GGACCTGCGG    1800

CCGCTGGAGG TGCGGCGGGG GCTGCGCGCC CAGGCCTGCG CCTTCTGGAA CCGCTTCCTC    1860
```

-continued

```
CCCAAATTGC TCAGCGCCAC CGACACGCTC GACGAGGCGG AGCGCCAGTG GAAGGCCGAG    1920

TTCCACCGCT GGAGCTCCTA CATGGTGCAC TGGAAGAACC AGTTCGACCA CTACAGCAAG    1980

CAGGATCGCT GCTCAGACCT GTGACCCCGG CGGGACCCCC ATGTCCTCCG CTCCGCCCGG    2040

CCCCCTAGCT GTATATACTA TTTATTTCAG GGCTGGGCTA TAACACAGAC GAGCCCCAGA    2100

CTCTGCCCAT CCCCACCCCA CCCCGACGTC CCCCGGGGCT CCCGGTCCTC TGGCATGTCT    2160

TCAGGCTGAG CTCCTCCCCG CGTGCCTTCG CCCTCTGGCT GCAAATAAAC TGTTACAGGC    2220

CAAAAAAAAA AAAAAAAAAA AAAAAAAAAA AAAAA                               2256
```

(2) INFORMATION FOR SEQ ID NO: 2:

(i) SEQUENCE CHARACTERISTICS:
        (A) LENGTH: 614 amino acids
        (B) TYPE: amino acid
        (C) STRANDEDNESS: single
        (D) TOPOLOGY: linear (xi) SEQUENCE DESCRIPTION: SEQ ID NO: 2:

```
Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Val Gly Ala Glu
            20                  25                  30

Gly Arg Glu Asp Ala Glu Leu Leu Val Thr Val Arg Gly Gly Arg Leu
        35                  40                  45

Arg Gly Ile Arg Leu Lys Thr Pro Gly Gly Pro Val Ser Ala Phe Leu
    50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asp Ala Thr Thr Phe
                85                  90                  95

Gln Ser Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
        115                 120                 125

Tyr Leu Asn Val Trp Thr Pro Tyr Pro Arg Pro Thr Ser Pro Thr Pro
    130                 135                 140

Val Leu Val Trp Ile Tyr Gly Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
            180                 185                 190

Pro Gly Ser Arg Glu Ala Pro Gly Asn Val Gly Leu Leu Asp Gln Arg
        195                 200                 205

Leu Ala Leu Gln Trp Val Gln Glu Asn Val Ala Ala Phe Gly Gly Asp
    210                 215                 220

Pro Thr Ser Val Thr Leu Phe Gly Glu Ser Ala Gly Ala Ala Ser Val
225                 230                 235                 240

Gly Met His Leu Leu Ser Pro Pro Ser Arg Gly Leu Phe His Arg Ala
                245                 250                 255

Val Leu Gln Ser Gly Ala Pro Asn Gly Pro Trp Ala Thr Val Gly Met
            260                 265                 270

Gly Glu Ala Arg Arg Arg Ala Thr Gln Leu Ala His Leu Val Gly Cys
        275                 280                 285
```

```
Pro Pro Gly Gly Thr Gly Gly Asn Asp Thr Glu Leu Val Ala Cys Leu
    290                 295                 300

Arg Thr Arg Pro Ala Gln Val Leu Val Asn His Glu Trp His Val Leu
305                 310                 315                 320

Pro Gln Glu Ser Val Phe Arg Phe Ser Phe Val Pro Val Val Asp Gly
                325                 330                 335

Asp Phe Leu Ser Asp Thr Pro Glu Ala Leu Ile Asn Ala Gly Asp Phe
                340                 345                 350

His Gly Leu Gln Val Leu Val Gly Val Lys Asp Glu Gly Ser Tyr
                355                 360                 365

Phe Leu Val Tyr Gly Ala Pro Gly Phe Ser Lys Asp Asn Glu Ser Leu
    370                 375                 380

Ile Ser Arg Ala Glu Phe Leu Ala Gly Val Arg Val Gly Val Pro Gln
385                 390                 395                 400

Val Ser Asp Leu Ala Ala Glu Ala Val Val Leu His Tyr Thr Asp Trp
                405                 410                 415

Leu His Pro Glu Asp Pro Ala Arg Leu Arg Glu Ala Leu Ser Asp Val
                420                 425                 430

Val Gly Asp His Asn Val Val Cys Pro Val Ala Gln Leu Ala Gly Arg
                435                 440                 445

Leu Ala Ala Gln Gly Ala Arg Val Tyr Ala Tyr Val Phe Glu His Arg
    450                 455                 460

Ala Ser Thr Leu Ser Trp Pro Leu Trp Met Gly Val Pro His Gly Tyr
465                 470                 475                 480

Glu Ile Glu Phe Ile Phe Gly Ile Pro Leu Asp Pro Ser Arg Asn Tyr
                485                 490                 495

Thr Ala Glu Glu Lys Ile Phe Ala Gln Arg Leu Met Arg Tyr Trp Ala
                500                 505                 510

Asn Phe Ala Arg Thr Gly Asp Pro Asn Glu Pro Arg Asp Pro Lys Ala
    515                 520                 525

Pro Gln Trp Pro Pro Tyr Thr Ala Gly Ala Gln Gln Tyr Val Ser Leu
    530                 535                 540

Asp Leu Arg Pro Leu Glu Val Arg Arg Gly Leu Arg Ala Gln Ala Cys
545                 550                 555                 560

Ala Phe Trp Asn Arg Phe Leu Pro Lys Leu Leu Ser Ala Thr Asp Thr
                565                 570                 575

Leu Asp Glu Ala Glu Arg Gln Trp Lys Ala Glu Phe His Arg Trp Ser
                580                 585                 590

Ser Tyr Met Val His Trp Lys Asn Gln Phe Asp His Tyr Ser Lys Gln
                595                 600                 605

Asp Arg Cys Ser Asp Leu
    610

(2) INFORMATION FOR SEQ ID NO: 3:

(i) SEQUENCE CHARACTERISTICS:
        (A) LENGTH: 3096 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 160..1959

(xi) SEQUENCE DESCRIPTION: SEQ ID NO: 3:
```

```
CCTCTCTCCC CTCATCTTTG CCAACCTGCC CCACCTCCTC TGCAGCTGAG CGATAACCCT      60

TGGGCCGACA GTGCCCTAAT CTCCTCCCTC CTGGCTTCTC GACCGACCCT TCACCCTTTC     120

CCTTTCTTTC TCCCAGCAGA CGCCGCCTGC CCTGCAGCC ATG AGG CCC CCG CAG        174
                                           Met Arg Pro Pro Gln
                                           1                5

TGT CTG CTG CAC ACG CCT TCC CTG GCT TCC CCA CTC CTT CTC CTC CTC       222
Cys Leu Leu His Thr Pro Ser Leu Ala Ser Pro Leu Leu Leu Leu Leu
            10              15              20

CTC TGG CTC CTG GGT GGA GGA GTG GGG GCT GAG GGC CGG GAG GAT GCA       270
Leu Trp Leu Leu Gly Gly Gly Val Gly Ala Glu Gly Arg Glu Asp Ala
        25              30              35

GAG CTG CTG GTG ACG GTG CGT GGG GGC CGG CTG CGG GGC ATT CGC CTG       318
Glu Leu Leu Val Thr Val Arg Gly Gly Arg Leu Arg Gly Ile Arg Leu
        40              45              50

AAG ACC CCC GGG GGC CCT GTC TCT GCT TTC CTG GGC ATC CCC TTT GCG       366
Lys Thr Pro Gly Gly Pro Val Ser Ala Phe Leu Gly Ile Pro Phe Ala
        55              60              65

GAG CCA CCC ATG GGA CCC CGT CGC TTT CTG CCA CCG GAG CCC AAG CAG       414
Glu Pro Pro Met Gly Pro Arg Arg Phe Leu Pro Pro Glu Pro Lys Gln
70              75              80              85

CCT TGG TCA GGG GTG GTA GAC GCT ACA ACC TTC CAG AGT GTC TGC TAC       462
Pro Trp Ser Gly Val Val Asp Ala Thr Thr Phe Gln Ser Val Cys Tyr
            90              95              100

CAA TAT GTG GAC ACC CTA TAC CCA GGT TTT GAG GGC ACC GAG ATG TGG       510
Gln Tyr Val Asp Thr Leu Tyr Pro Gly Phe Glu Gly Thr Glu Met Trp
            105             110             115

AAC CCC AAC CGT GAG CTG AGC GAG GAC TGC CTG TAC CTC AAC GTG TGG       558
Asn Pro Asn Arg Glu Leu Ser Glu Asp Cys Leu Tyr Leu Asn Val Trp
        120             125             130

ACA CCA TAC CCC CGG CCT ACA TCC CCC ACC CCT GTC CTC GTC TGG ATC       606
Thr Pro Tyr Pro Arg Pro Thr Ser Pro Thr Pro Val Leu Val Trp Ile
        135             140             145

TAT GGG GGT GGC TTC TAC AGT GGG GCC TCC TCC TTG GAC GTG TAC GAT       654
Tyr Gly Gly Gly Phe Tyr Ser Gly Ala Ser Ser Leu Asp Val Tyr Asp
150             155             160             165

GGC CGC TTC TTG GTA CAG GCC GAG AGG ACT GTG CTG GTG TCC ATG AAC       702
Gly Arg Phe Leu Val Gln Ala Glu Arg Thr Val Leu Val Ser Met Asn
            170             175             180

TAC CGG GTG GGA GCC TTT GGC TTC CTG GCC CTG CCG GGG AGC CGA GAG       750
Tyr Arg Val Gly Ala Phe Gly Phe Leu Ala Leu Pro Gly Ser Arg Glu
            185             190             195

GCC CCG GGC AAT GTG GGT CTC CTG GAT CAG AGG CTG GCC CTG CAG TGG       798
Ala Pro Gly Asn Val Gly Leu Leu Asp Gln Arg Leu Ala Leu Gln Trp
        200             205             210

GTG CAG GAG AAC GTG GCA GCC TTC GGG GGT GAC CCG ACA TCA GTG ACG       846
Val Gln Glu Asn Val Ala Ala Phe Gly Gly Asp Pro Thr Ser Val Thr
215             220             225

CTG TTT GGG GAG AGC GCG GGA GCC GCC TCG GTG GGC ATG CAC CTG CTG       894
Leu Phe Gly Glu Ser Ala Gly Ala Ala Ser Val Gly Met His Leu Leu
230             235             240             245

TCC CCG CCC AGC CGG GGC CTG TTC CAC AGG GCC GTG CTG CAG AGC GGT       942
Ser Pro Pro Ser Arg Gly Leu Phe His Arg Ala Val Leu Gln Ser Gly
            250             255             260

GCC CCC AAT GGA CCC TGG GCC ACG GTG GGC ATG GGA GAG GCC CGT CGC       990
Ala Pro Asn Gly Pro Trp Ala Thr Val Gly Met Gly Glu Ala Arg Arg
        265             270             275

AGG GCC ACG CAG CTG GCC CAC CTT GTG GGC TGT CCT CCA GGC GGC ACT      1038
Arg Ala Thr Gln Leu Ala His Leu Val Gly Cys Pro Pro Gly Gly Thr
            280             285             290
```

-continued

```
GGT GGG AAT GAC ACA GAG CTG GTA GCC TGC CTT CGG ACA CGA CCA GCG      1086
Gly Gly Asn Asp Thr Glu Leu Val Ala Cys Leu Arg Thr Arg Pro Ala
        295                 300                 305

CAG GTC CTG GTG AAC CAC GAA TGG CAC GTG CTG CCT CAA GAA AGC GTC      1134
Gln Val Leu Val Asn His Glu Trp His Val Leu Pro Gln Glu Ser Val
310                 315                 320                 325

TTC CGG TTC TCC TTC GTG CCT GTG GTA GAT GGA GAC TTC CTC AGT GAC      1182
Phe Arg Phe Ser Phe Val Pro Val Val Asp Gly Asp Phe Leu Ser Asp
                330                 335                 340

ACC CCA GAG GCC CTC ATC AAC GCG GGA GAC TTC CAC GGC CTG CAG GTG      1230
Thr Pro Glu Ala Leu Ile Asn Ala Gly Asp Phe His Gly Leu Gln Val
            345                 350                 355

CTG GTG GGT GTG GTG AAG GAT GAG GGC TCG TAT TTT CTG GTT TAC GGG      1278
Leu Val Gly Val Val Lys Asp Glu Gly Ser Tyr Phe Leu Val Tyr Gly
        360                 365                 370

GCC CCA GGC TTC AGC AAA GAC AAC GAG TCT CTC ATC AGC CGG GCC GAG      1326
Ala Pro Gly Phe Ser Lys Asp Asn Glu Ser Leu Ile Ser Arg Ala Glu
    375                 380                 385

TTC CTG GCC GGG GTG CGG GTC GGG GTT CCC CAG GTA AGT GAC CTG GCA      1374
Phe Leu Ala Gly Val Arg Val Gly Val Pro Gln Val Ser Asp Leu Ala
390                 395                 400                 405

GCC GAG GCT GTG GTC CTG CAT TAC ACA GAC TGG CTG CAT CCC GAG GAC      1422
Ala Glu Ala Val Val Leu His Tyr Thr Asp Trp Leu His Pro Glu Asp
                410                 415                 420

CCG GCA CGC CTG AGG GAG GCC CTG AGC GAT GTG GTG GGC GAC CAC AAT      1470
Pro Ala Arg Leu Arg Glu Ala Leu Ser Asp Val Val Gly Asp His Asn
            425                 430                 435

GTC GTG TGC CCC GTG GCC CAG CTG GCT GGG CGA CTG GCT GCC CAG GGT      1518
Val Val Cys Pro Val Ala Gln Leu Ala Gly Arg Leu Ala Ala Gln Gly
        440                 445                 450

GCC CGG GTC TAC GCC TAC GTC TTT GAA CAC CGT GCT TCC ACG CTC TCC      1566
Ala Arg Val Tyr Ala Tyr Val Phe Glu His Arg Ala Ser Thr Leu Ser
    455                 460                 465

TGG CCC CTG TGG ATG GGG GTG CCC CAC GGC TAC GAG ATC GAG TTC ATC      1614
Trp Pro Leu Trp Met Gly Val Pro His Gly Tyr Glu Ile Glu Phe Ile
470                 475                 480                 485

TTT GGG ATC CCC CTG GAC CCC TCT CGA AAC TAC ACG GCA GAG GAG AAA      1662
Phe Gly Ile Pro Leu Asp Pro Ser Arg Asn Tyr Thr Ala Glu Glu Lys
                490                 495                 500

ATC TTC GCC CAG CGA CTG ATG CGA TAC TGG GCC AAC TTT GCC CGC ACA      1710
Ile Phe Ala Gln Arg Leu Met Arg Tyr Trp Ala Asn Phe Ala Arg Thr
            505                 510                 515

GGG GAT CCC AAT GAG CCC CGA GAC CCC AAG GCC CCA CAA TGG CCC CCG      1758
Gly Asp Pro Asn Glu Pro Arg Asp Pro Lys Ala Pro Gln Trp Pro Pro
        520                 525                 530

TAC ACG GCG GGG GCT CAG CAG TAC GTT AGT CTG GAC CTG CGG CCG CTG      1806
Tyr Thr Ala Gly Ala Gln Gln Tyr Val Ser Leu Asp Leu Arg Pro Leu
    535                 540                 545

GAG GTG CGG CGG GGG CTG CGC GCC CAG GCC TGC GCC TTC TGG AAC CGC      1854
Glu Val Arg Arg Gly Leu Arg Ala Gln Ala Cys Ala Phe Trp Asn Arg
550                 555                 560                 565

TTC CTC CCC AAA TTG CTC AGC GCC ACC GGT ATG CAG GGG CCA GCG GGC      1902
Phe Leu Pro Lys Leu Leu Ser Ala Thr Gly Met Gln Gly Pro Ala Gly
                570                 575                 580

AGC GGC TGG GAG GAG GGG AGT GGG AGC CCG CCA GGT GTA ACC CCT CTC      1950
Ser Gly Trp Glu Glu Gly Ser Gly Ser Pro Pro Gly Val Thr Pro Leu
            585                 590                 595

TTC TCC CCC TAGCCTCGGA GGCTCCCAGC ACCTGCCCAG GCTTCACCCA              1999
Phe Ser Pro
```

-continued

```
         600
TGGGGAGGCT GCTCCGAGGC CCGGCCTCCC CCTGCCCCTC CTCCTCCTCC ACCAGCTTCT    2059

CCTCCTCTTC CTCTCCCACC TCCGGCGGCT GTGAACACGG CCTCTTCCCC TACGGCCTAC    2119

AGGGGCCCCT CCTCTAATGA GTGGTAGGAC CTGTGGGGAA GGGCCCCACT CAGGGATCTC    2179

AGACCTAGTG CTCCCTTCCT CCTCAAACCG AGAGACTCAC ACTGGACAGG GCAGGAGGAG    2239

GGGCCGTGCC TCCCACCCTT CTCAGGGACC CCCACGCCTT TGTTGTTTGA ATGGAAATGG    2299

AAAAGCCAGT ATTCTTTTAT AAAATTATCT TTTGGAACCT GAGCCTGACA TTGGGGAAG     2359

TGGAGGCCCG GAAACGGGGT AGCACCCCCA TTGGGGCTAT AACGGTCAAC CATTTCTGTG    2419

TCTTCTTTTT CCCCCAACCT CCCCCTCCTG TCCCCTCTGT TCCCGTCTTC CGGTCATTCT    2479

TTTCTCCTCC TCTCTCCTTC CTGCTGTCCT TCTCGGCCCC GCCTCTGCCC TCATCCTCCC    2539

TCTCGTCTTT CGCACATTCT CCTGATCCTC TTGCCACCGT CCCACGTGGT CGCCTGCATT    2599

TCTCCGTGCG TCCTCCCTGC ACTCATACCC CCCCTTCAAC CCGCCCAAAT GTCCGATCCC    2659

CGACCTTCCT CGTGCCGTCC TCCCCTCCCG CCTCGCTGGG CGCCCTGGCC GCAGACACGC    2719

TCGACACGCT CGACGAGGCG GAGCGCCAGT GGAAGGCCGA GTTCCACCGC TGGAGCTCCT    2779

ACATGGTGCA CTGGAAGAAC CAGTTCGACC ACTACAGCAA GCAGGATCGC TGCTCAGACC    2839

TGTGACCCCG GCGGGACCCC CATGTCCTCC GCTCCGCCCG GCCCCTAGC  TGTATATACT    2899

ATTTATTTCA GGGCTGGGCT ATAACACAGA CGAGCCCCAG ACTCTGCCCA TCCCCACCCC    2959

ACCCCGACGT CCCCCGGGGC TCCCGGTCCT CTGGCATGTC TTCAGGCTGA GCTCCTCCCC    3019

GCGTGCCTTC GCCCTCTGGC TGCAAATAAA CTGTTACAGG CCAAAAAAAA AAAAAAAAA    3079

AAAAAAAAAA AAAAAA                                                    3096
```

(2) INFORMATION FOR SEQ ID NO: 4:

(i) SEQUENCE CHARACTERISTICS:
        (A) LENGTH: 600 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Arg Pro Pro Gln Cys Leu Leu His Thr Pro Ser Leu Ala Ser Pro
 1               5                  10                  15

Leu Leu Leu Leu Leu Leu Trp Leu Leu Gly Gly Gly Val Gly Ala Glu
            20                  25                  30

Gly Arg Glu Asp Ala Glu Leu Leu Val Thr Val Arg Gly Gly Arg Leu
        35                  40                  45

Arg Gly Ile Arg Leu Lys Thr Pro Gly Gly Pro Val Ser Ala Phe Leu
    50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asp Ala Thr Thr Phe
                85                  90                  95

Gln Ser Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
        115                 120                 125

Tyr Leu Asn Val Trp Thr Pro Tyr Pro Arg Pro Thr Ser Pro Thr Pro
    130                 135                 140
```

-continued

```
Val Leu Val Trp Ile Tyr Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
                180                 185                 190

Pro Gly Ser Arg Glu Ala Pro Gly Asn Val Gly Leu Leu Asp Gln Arg
                195                 200                 205

Leu Ala Leu Gln Trp Val Gln Glu Asn Val Ala Ala Phe Gly Gly Asp
            210                 215                 220

Pro Thr Ser Val Thr Leu Phe Gly Glu Ser Ala Gly Ala Ala Ser Val
225                 230                 235                 240

Gly Met His Leu Leu Ser Pro Pro Ser Arg Gly Leu Phe His Arg Ala
                245                 250                 255

Val Leu Gln Ser Gly Ala Pro Asn Gly Pro Trp Ala Thr Val Gly Met
                260                 265                 270

Gly Glu Ala Arg Arg Arg Ala Thr Gln Leu Ala His Leu Val Gly Cys
                275                 280                 285

Pro Pro Gly Gly Thr Gly Gly Asn Asp Thr Glu Leu Val Ala Cys Leu
290                 295                 300

Arg Thr Arg Pro Ala Gln Val Leu Val Asn His Glu Trp His Val Leu
305                 310                 315                 320

Pro Gln Glu Ser Val Phe Arg Phe Ser Phe Val Pro Val Val Asp Gly
                325                 330                 335

Asp Phe Leu Ser Asp Thr Pro Glu Ala Leu Ile Asn Ala Gly Asp Phe
                340                 345                 350

His Gly Leu Gln Val Leu Val Gly Val Val Lys Asp Glu Gly Ser Tyr
                355                 360                 365

Phe Leu Val Tyr Gly Ala Pro Gly Phe Ser Lys Asp Asn Glu Ser Leu
                370                 375                 380

Ile Ser Arg Ala Glu Phe Leu Ala Gly Val Arg Val Gly Val Pro Gln
385                 390                 395                 400

Val Ser Asp Leu Ala Ala Glu Ala Val Val Leu His Tyr Thr Asp Trp
                405                 410                 415

Leu His Pro Glu Asp Pro Ala Arg Leu Arg Glu Ala Leu Ser Asp Val
                420                 425                 430

Val Gly Asp His Asn Val Val Cys Pro Val Ala Gln Leu Ala Gly Arg
            435                 440                 445

Leu Ala Ala Gln Gly Ala Arg Val Tyr Ala Tyr Val Phe Glu His Arg
450                 455                 460

Ala Ser Thr Leu Ser Trp Pro Leu Trp Met Gly Val Pro His Gly Tyr
465                 470                 475                 480

Glu Ile Glu Phe Ile Phe Gly Ile Pro Leu Asp Pro Ser Arg Asn Tyr
                485                 490                 495

Thr Ala Glu Glu Lys Ile Phe Ala Gln Arg Leu Met Arg Tyr Trp Ala
                500                 505                 510

Asn Phe Ala Arg Thr Gly Asp Pro Asn Glu Pro Arg Asp Pro Lys Ala
                515                 520                 525

Pro Gln Trp Pro Pro Tyr Thr Ala Gly Ala Gln Gln Tyr Val Ser Leu
            530                 535                 540

Asp Leu Arg Pro Leu Glu Val Arg Arg Gly Leu Arg Ala Gln Ala Cys
545                 550                 555                 560

Ala Phe Trp Asn Arg Phe Leu Pro Lys Leu Leu Ser Ala Thr Gly Met
```

-continued

```
                        565                 570                 575
Gln Gly Pro Ala Gly Ser Gly Trp Glu Glu Gly Ser Gly Pro Pro
        580                 585                 590

Gly Val Thr Pro Leu Phe Ser Pro
        595                 600

(2) INFORMATION FOR SEQ ID NO: 5:

(i) SEQUENCE CHARACTERISTICS:
        (A) LENGTH: 3016 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 160..2010

(xi) SEQUENCE DESCRIPTION: SEQ ID NO: 5:

CCTCTCTCCC CTCATCTTTG CCAACCTGCC CCACCTCCTC TGCAGCTGAG CGATAACCCT        60

TGGGCCGACA GTGCCCTAAT CTCCTCCCTC CTGGCTTCTC GACCGACCCT TCACCCTTTC       120

CCTTTCTTTC TCCCAGCAGA CGCCGCCTGC CCTGCAGCC ATG AGG CCC CCG CAG         174
                                            Met Arg Pro Pro Gln
                                                            605

TGT CTG CTG CAC ACG CCT TCC CTG GCT TCC CCA CTC CTT CTC CTC CTC        222
Cys Leu Leu His Thr Pro Ser Leu Ala Ser Pro Leu Leu Leu Leu Leu
                610                 615                 620

CTC TGG CTC CTG GGT GGA GGA GTG GGG GCT GAG GGC CGG GAG GAT GCA        270
Leu Trp Leu Leu Gly Gly Gly Val Gly Ala Glu Gly Arg Glu Asp Ala
                625                 630                 635

GAG CTG CTG GTG ACG GTG CGT GGG GGC CGG CTG CGG GGC ATT CGC CTG        318
Glu Leu Leu Val Thr Val Arg Gly Gly Arg Leu Arg Gly Ile Arg Leu
            640                 645                 650

AAG ACC CCC GGG GGC CCT GTC TCT GCT TTC CTG GGC ATC CCC TTT GCG        366
Lys Thr Pro Gly Gly Pro Val Ser Ala Phe Leu Gly Ile Pro Phe Ala
655                 660                 665

GAG CCA CCC ATG GGA CCC CGT CGC TTT CTG CCA CCG GAG CCC AAG CAG        414
Glu Pro Pro Met Gly Pro Arg Arg Phe Leu Pro Pro Glu Pro Lys Gln
670                 675                 680                 685

CCT TGG TCA GGG GTG GTA GAC GCT ACA ACC TTC CAG AGT GTC TGC TAC        462
Pro Trp Ser Gly Val Val Asp Ala Thr Thr Phe Gln Ser Val Cys Tyr
                690                 695                 700

CAA TAT GTG GAC ACC CTA TAC CCA GGT TTT GAG GGC ACC GAG ATG TGG        510
Gln Tyr Val Asp Thr Leu Tyr Pro Gly Phe Glu Gly Thr Glu Met Trp
                705                 710                 715

AAC CCC AAC CGT GAG CTG AGC GAG GAC TGC CTG TAC CTC AAC GTG TGG        558
Asn Pro Asn Arg Glu Leu Ser Glu Asp Cys Leu Tyr Leu Asn Val Trp
                720                 725                 730

ACA CCA TAC CCC CGG CCT ACA TCC CCC ACC CCT GTC CTC GTC TGG ATC        606
Thr Pro Tyr Pro Arg Pro Thr Ser Pro Thr Pro Val Leu Val Trp Ile
        735                 740                 745

TAT GGG GGT GGC TTC TAC AGT GGG GCC TCC TCC TTG GAC GTG TAC GAT        654
Tyr Gly Gly Gly Phe Tyr Ser Gly Ala Ser Ser Leu Asp Val Tyr Asp
750                 755                 760                 765

GGC CGC TTC TTG GTA CAG GCC GAG AGG ACT GTG CTG GTG TCC ATG AAC        702
Gly Arg Phe Leu Val Gln Ala Glu Arg Thr Val Leu Val Ser Met Asn
                770                 775                 780

TAC CGG GTG GGA GCC TTT GGC TTC CTG GCC CTG CCG GGG AGC CGA GAG        750
Tyr Arg Val Gly Ala Phe Gly Phe Leu Ala Leu Pro Gly Ser Arg Glu
                785                 790                 795
```

```
                                                           -continued
GCC CCG GGC AAT GTG GGT CTC CTG GAT CAG AGG CTG GCC CTG CAG TGG       798
Ala Pro Gly Asn Val Gly Leu Leu Asp Gln Arg Leu Ala Leu Gln Trp
            800                 805                 810

GTG CAG GAG AAC GTG GCA GCC TTC GGG GGT GAC CCG ACA TCA GTG ACG       846
Val Gln Glu Asn Val Ala Ala Phe Gly Gly Asp Pro Thr Ser Val Thr
815                 820                 825

CTG TTT GGG GAG AGC GCG GGA GCC GCC TCG GTG GGC ATG CAC CTG CTG       894
Leu Phe Gly Glu Ser Ala Gly Ala Ala Ser Val Gly Met His Leu Leu
830                 835                 840                 845

TCC CCG CCC AGC CGG GGC CTG TTC CAC AGG GCC GTG CTG CAG AGC GGT       942
Ser Pro Pro Ser Arg Gly Leu Phe His Arg Ala Val Leu Gln Ser Gly
                850                 855                 860

GCC CCC AAT GGA CCC TGG GCC ACG GTG GGC ATG GGA GAG GCC CGT CGC       990
Ala Pro Asn Gly Pro Trp Ala Thr Val Gly Met Gly Glu Ala Arg Arg
            865                 870                 875

AGG GCC ACG CAG CTG GCC CAC CTT GTG GGC TGT CCT CCA GGC GGC ACT      1038
Arg Ala Thr Gln Leu Ala His Leu Val Gly Cys Pro Pro Gly Gly Thr
        880                 885                 890

GGT GGG AAT GAC ACA GAG CTG GTA GCC TGC CTT CGG ACA CGA CCA GCG      1086
Gly Gly Asn Asp Thr Glu Leu Val Ala Cys Leu Arg Thr Arg Pro Ala
    895                 900                 905

CAG GTC CTG GTG AAC CAC GAA TGG CAC GTG CTG CCT CAA GAA AGC GTC      1134
Gln Val Leu Val Asn His Glu Trp His Val Leu Pro Gln Glu Ser Val
910                 915                 920                 925

TTC CGG TTC TCC TTC GTG CCT GTG GTA GAT GGA GAC TTC CTC AGT GAC      1182
Phe Arg Phe Ser Phe Val Pro Val Val Asp Gly Asp Phe Leu Ser Asp
                930                 935                 940

ACC CCA GAG GCC CTC ATC AAC GCG GGA GAC TTC CAC GGC CTG CAG GTG      1230
Thr Pro Glu Ala Leu Ile Asn Ala Gly Asp Phe His Gly Leu Gln Val
            945                 950                 955

CTG GTG GGT GTG GTG AAG GAT GAG GGC TCG TAT TTT CTG GTT TAC GGG      1278
Leu Val Gly Val Val Lys Asp Glu Gly Ser Tyr Phe Leu Val Tyr Gly
        960                 965                 970

GCC CCA GGC TTC AGC AAA GAC AAC GAG TCT CTC ATC AGC CGG GCC GAG      1326
Ala Pro Gly Phe Ser Lys Asp Asn Glu Ser Leu Ile Ser Arg Ala Glu
    975                 980                 985

TTC CTG GCC GGG GTG CGG GTC GGG GTT CCC CAG GTA AGT GAC CTG GCA      1374
Phe Leu Ala Gly Val Arg Val Gly Val Pro Gln Val Ser Asp Leu Ala
990                 995                 1000                1005

GCC GAG GCT GTG GTC CTG CAT TAC ACA GAC TGG CTG CAT CCC GAG GAC      1422
Ala Glu Ala Val Val Leu His Tyr Thr Asp Trp Leu His Pro Glu Asp
                1010                1015                1020

CCG GCA CGC CTG AGG GAG GCC CTG AGC GAT GTG GTG GGC GAC CAC AAT      1470
Pro Ala Arg Leu Arg Glu Ala Leu Ser Asp Val Val Gly Asp His Asn
            1025                1030                1035

GTC GTG TGC CCC GTG GCC CAG CTG GCT GGG CGA CTG GCT GCC CAG GGT      1518
Val Val Cys Pro Val Ala Gln Leu Ala Gly Arg Leu Ala Ala Gln Gly
        1040                1045                1050

GCC CGG GTC TAC GCC TAC GTC TTT GAA CAC CGT GCT TCC ACG CTC TCC      1566
Ala Arg Val Tyr Ala Tyr Val Phe Glu His Arg Ala Ser Thr Leu Ser
    1055                1060                1065

TGG CCC CTG TGG ATG GGG GTG CCC CAC GGC TAC GAG ATC GAG TTC ATC      1614
Trp Pro Leu Trp Met Gly Val Pro His Gly Tyr Glu Ile Glu Phe Ile
1070                1075                1080                1085

TTT GGG ATC CCC CTG GAC CCC TCT CGA AAC TAC ACG GCA GAG GAG AAA      1662
Phe Gly Ile Pro Leu Asp Pro Ser Arg Asn Tyr Thr Ala Glu Glu Lys
                1090                1095                1100

ATC TTC GCC CAG CGA CTG ATG CGA TAC TGG GCC AAC TTT GCC CGC ACA      1710
Ile Phe Ala Gln Arg Leu Met Arg Tyr Trp Ala Asn Phe Ala Arg Thr
            1105                1110                1115
```

```
GGG GAT CCC AAT GAG CCC CGA GAC CCC AAG GCC CCA CAA TGG CCC CCG      1758
Gly Asp Pro Asn Glu Pro Arg Asp Pro Lys Ala Pro Gln Trp Pro Pro
        1120                1125                1130

TAC ACG GCG GGG GCT CAG CAG TAC GTT AGT CTG GAC CTG CGG CCG CTG      1806
Tyr Thr Ala Gly Ala Gln Gln Tyr Val Ser Leu Asp Leu Arg Pro Leu
    1135                1140                1145

GAG GTG CGG CGG GGG CTG CGC GCC CAG GCC TGC GCC TTC TGG AAC CGC      1854
Glu Val Arg Arg Gly Leu Arg Ala Gln Ala Cys Ala Phe Trp Asn Arg
1150                1155                1160                1165

TTC CTC CCC AAA TTG CTC AGC GCC ACC GCC TCG GAG GCT CCC AGC ACC      1902
Phe Leu Pro Lys Leu Leu Ser Ala Thr Ala Ser Glu Ala Pro Ser Thr
                1170                1175                1180

TGC CCA GGC TTC ACC CAT GGG GAG GCT GCT CCG AGG CCC GGC CTC CCC      1950
Cys Pro Gly Phe Thr His Gly Glu Ala Ala Pro Arg Pro Gly Leu Pro
            1185                1190                1195

CTG CCC CTC CTC CTC CTC CAC CAG CTT CTC CTC CTC TTC CTC TCC CAC      1998
Leu Pro Leu Leu Leu Leu His Gln Leu Leu Leu Leu Phe Leu Ser His
        1200                1205                1210

CTC CGG CGG CTG TGAACACGGC CTCTTCCCCT ACGGCCTACA GGGGCCCCTC          2050
Leu Arg Arg Leu
    1215

CTCTAATGAG TGGTAGGACC TGTGGGAAG GGCCCCACTC AGGGATCTCA GACCTAGTGC    2110

TCCCTTCCTC CTCAAACCGA GAGACTCACA CTGGACAGGG CAGGAGGAGG GGCCGTGCCT    2170

CCCACCCTTC TCAGGGACCC CCACGCCTTT GTTGTTTGAA TGGAAATGGA AAAGCCAGTA    2230

TTCTTTTATA AAATTATCTT TTGGAACCTG AGCCTGACAT TGGGGGAAGT GGAGGCCCGG    2290

AAACGGGGTA GCACCCCCAT TGGGGCTATA ACGGTCAACC ATTTCTGTCT CTTCTTTTTC    2350

CCCCAACCTC CCCCTCCTGT CCCCTCTGTT CCCGTCTTCC GGTCATTCTT TTCTCCTCCT    2410

CTCTCCTTCC TGCTGTCCTT CTCGGCCCCG CCTCTGCCCT CATCCTCCCT CTCGTCTTCT    2470

GCACATTCTC CTGATCCTCT TGCCACCGTC CCACGTGGTC GCCTGCATTT CTCCGTGCGT    2530

CCTCCCTGCA CTCATACCCC CCCTTCAACC CGCCCAAATG TCCGATCCCC GACCTTCCTC    2590

GTGCCGTCCT CCCCTCCCGC CTCGCTGGGC GCCCTGGCCG CAGACACGCT CGACACGCTC    2650

GACGAGGCGG AGCGCCAGTG GAAGGCCGAG TTCCACCGCT GGAGCTCCTA CATGGTGCAC    2710

TGGAAGAACC AGTTCGACCA CTACAGCAAG CAGGATCGCT GCTCAGACCT GTGACCCCGG    2770

CGGGACCCCC ATGTCCTCCG CTCCGCCCGG CCCCCTAGCT GTATATACTA TTTATTTCAG    2830

GGCTGGGCTA TAACACAGAC GAGCCCCAGA CTCTGCCCAT CCCCACCCCA CCCCGACGTC    2890

CCCCGGGGCT CCCGGTCCTC TGGCATGTCT TCAGGCTGAG CTCCTCCCCG CGTGCCTTCG    2950

CCCTCTGGCT GCAAATAAAC TGTTACAGGC CAAAAAAAAA AAAAAAAAAA AAAAAAAAA    3010

AAAAAA                                                               3016

(2) INFORMATION FOR SEQ ID NO: 6:

(i) SEQUENCE CHARACTERISTICS:
        (A) LENGTH: 617 amino acids
        (B) TYPE: amino acid
        (D) TOPOLOGY: linear (ii) MOLECULE TYPE: protein (xi) SEQUENCE DESCRIPTION: SEQ ID NO: 6:

Met Arg Pro Pro Gln Cys Leu Leu His Thr Pro Ser Leu Ala Ser Pro
 1               5                  10                  15

Leu Leu Leu Leu Leu Leu Trp Leu Leu Gly Gly Gly Val Gly Ala Glu
```

-continued

```
                20                  25                  30
Gly Arg Glu Asp Ala Glu Leu Leu Val Thr Val Arg Gly Gly Arg Leu
            35                  40                  45

Arg Gly Ile Arg Leu Lys Thr Pro Gly Pro Val Ser Ala Phe Leu
 50                  55                  60

Gly Ile Pro Phe Ala Glu Pro Pro Met Gly Pro Arg Arg Phe Leu Pro
 65                  70                  75                  80

Pro Glu Pro Lys Gln Pro Trp Ser Gly Val Val Asp Ala Thr Thr Phe
                85                  90                  95

Gln Ser Val Cys Tyr Gln Tyr Val Asp Thr Leu Tyr Pro Gly Phe Glu
                100                 105                 110

Gly Thr Glu Met Trp Asn Pro Asn Arg Glu Leu Ser Glu Asp Cys Leu
            115                 120                 125

Tyr Leu Asn Val Trp Thr Pro Tyr Pro Arg Pro Thr Ser Pro Thr Pro
 130                 135                 140

Val Leu Val Trp Ile Tyr Gly Gly Phe Tyr Ser Gly Ala Ser Ser
 145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
            180                 185                 190

Pro Gly Ser Arg Glu Ala Pro Gly Asn Val Gly Leu Leu Asp Gln Arg
 195                 200                 205

Leu Ala Leu Gln Trp Val Gln Glu Asn Val Ala Ala Phe Gly Gly Asp
 210                 215                 220

Pro Thr Ser Val Thr Leu Phe Gly Glu Ser Ala Gly Ala Ala Ser Val
225                 230                 235                 240

Gly Met His Leu Leu Ser Pro Pro Ser Arg Gly Leu Phe His Arg Ala
                245                 250                 255

Val Leu Gln Ser Gly Ala Pro Asn Gly Pro Trp Ala Thr Val Gly Met
            260                 265                 270

Gly Glu Ala Arg Arg Arg Ala Thr Gln Leu Ala His Leu Val Gly Cys
 275                 280                 285

Pro Pro Gly Gly Thr Gly Gly Asn Asp Thr Glu Leu Val Ala Cys Leu
 290                 295                 300

Arg Thr Arg Pro Ala Gln Val Leu Val Asn His Glu Trp His Val Leu
305                 310                 315                 320

Pro Gln Glu Ser Val Phe Arg Phe Ser Phe Val Pro Val Val Asp Gly
                325                 330                 335

Asp Phe Leu Ser Asp Thr Pro Glu Ala Leu Ile Asn Ala Gly Asp Phe
            340                 345                 350

His Gly Leu Gln Val Leu Val Gly Val Val Lys Asp Glu Gly Ser Tyr
 355                 360                 365

Phe Leu Val Tyr Gly Ala Pro Gly Phe Ser Lys Asp Asn Glu Ser Leu
 370                 375                 380

Ile Ser Arg Ala Glu Phe Leu Ala Gly Val Arg Val Gly Val Pro Gln
385                 390                 395                 400

Val Ser Asp Leu Ala Ala Glu Ala Val Val Leu His Tyr Thr Asp Trp
                405                 410                 415

Leu His Pro Glu Asp Pro Ala Arg Leu Arg Glu Ala Leu Ser Asp Val
            420                 425                 430

Val Gly Asp His Asn Val Val Cys Pro Val Ala Gln Leu Ala Gly Arg
 435                 440                 445
```

```
Leu Ala Ala Gln Gly Ala Arg Val Tyr Ala Tyr Val Phe Glu His Arg
    450                 455                 460

Ala Ser Thr Leu Ser Trp Pro Leu Trp Met Gly Val Pro His Gly Tyr
465                 470                 475                 480

Glu Ile Glu Phe Ile Phe Gly Ile Pro Leu Asp Pro Ser Arg Asn Tyr
                    485                 490                 495

Thr Ala Glu Glu Lys Ile Phe Ala Gln Arg Leu Met Arg Tyr Trp Ala
                500                 505                 510

Asn Phe Ala Arg Thr Gly Asp Pro Asn Glu Pro Arg Asp Pro Lys Ala
                515                 520                 525

Pro Gln Trp Pro Pro Tyr Thr Ala Gly Ala Gln Gln Tyr Val Ser Leu
    530                 535                 540

Asp Leu Arg Pro Leu Glu Val Arg Arg Gly Leu Arg Ala Gln Ala Cys
545                 550                 555                 560

Ala Phe Trp Asn Arg Phe Leu Pro Lys Leu Leu Ser Ala Thr Ala Ser
                565                 570                 575

Glu Ala Pro Ser Thr Cys Pro Gly Phe Thr His Gly Glu Ala Ala Pro
                580                 585                 590

Arg Pro Gly Leu Pro Leu Pro Leu Leu Leu His Gln Leu Leu Leu
    595                 600                 605

Leu Phe Leu Ser His Leu Arg Arg Leu
    610                 615

(2) INFORMATION FOR SEQ ID NO: 7:

(i) SEQUENCE CHARACTERISTICS:
        (A) LENGTH: 45 amino acids
        (B) TYPE: amino acid
        (C) STRANDEDNESS: single
        (D) TOPOLOGY: linear (xi) SEQUENCE DESCRIPTION: SEQ ID NO: 7:

Leu Leu Ser Ala Thr Asp Thr Leu Asp Glu Ala Glu Arg Gln Trp Lys
1               5                   10                  15

Ala Glu Phe His Arg Trp Ser Ser Tyr Met Val His Trp Lys Asn Gln
                20                  25                  30

Phe Asp His Tyr Ser Lys Gln Asp Arg Cys Ser Asp Leu
            35                  40                  45

(2) INFORMATION FOR SEQ ID NO: 8:

(i) SEQUENCE CHARACTERISTICS:
        (A) LENGTH: 45 amino acids
        (B) TYPE: amino acid
        (C) STRANDEDNESS: single
        (D) TOPOLOGY: linear (xi) SEQUENCE DESCRIPTION: SEQ ID NO: 8:

Leu Leu Ser Ala Thr Asp Thr Leu Asp Glu Ala Glu Arg Gln Trp Lys
1               5                   10                  15

Ala Glu Phe His Arg Trp Ser Ser Tyr Met Val His Trp Lys Asn Gln
                20                  25                  30

Phe Asp His Tyr Ser Lys Gln Glu Arg Cys Ser Asp Leu
            35                  40                  45

(2) INFORMATION FOR SEQ ID NO: 9:

(i) SEQUENCE CHARACTERISTICS:
        (A) LENGTH: 48 amino acids
```

(B) TYPE: amino acid
            (C) STRANDEDNESS: single
            (D) TOPOLOGY: linear (xi) SEQUENCE DESCRIPTION: SEQ ID NO: 9:

Leu Leu Ser Ala Thr Ala Ser Glu Ala Pro Ser Thr Cys Pro Gly Phe
1               5                   10                  15

Thr His Gly Glu Ala Ala Pro Arg Pro Gly Leu Pro Leu Pro Leu Leu
                20                  25                  30

Leu Leu His Cys Leu Leu Leu Leu Phe Leu Ser His Leu Arg Arg Leu
            35                  40                  45

(2) INFORMATION FOR SEQ ID NO: 10:

(i) SEQUENCE CHARACTERISTICS:
        (A) LENGTH: 47 amino acids
        (B) TYPE: amino acid
        (C) STRANDEDNESS: single
        (D) TOPOLOGY: linear (xi) SEQUENCE DESCRIPTION: SEQ ID NO: 10:

Leu Leu Ser Ala Thr Ala Thr Glu Val Pro Cys Thr Cys Pro Ser Pro
1               5                   10                  15

Ala His Gly Glu Ala Ala Pro Arg Pro Gly Pro Ala Leu Ser Leu Ser
                20                  25                  30

Leu Leu Phe Phe Leu Phe Leu Leu His Ser Gly Leu Arg Trp Leu
            35                  40                  45

(2) INFORMATION FOR SEQ ID NO: 11:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO: 11:

Leu Leu Ser Ala Thr Gly Met Gln Gly Pro Ala Gly Ser Gly Trp Glu
1               5                   10                  15

Glu Gly Ser Gly Ser Pro Pro Gly Val Thr Pro Leu Phe Ser Pro
                20                  25                  30

(2) INFORMATION FOR SEQ ID NO: 12:

(i) SEQUENCE CHARACTERISTICS:
        (A) LENGTH: 34 amino acids
        (B) TYPE: amino acid
        (C) STRANDEDNESS: single
        (D) TOPOLOGY: linear (xi) SEQUENCE DESCRIPTION: SEQ ID NO: 12:

Leu Leu Ser Ala Thr Gly Arg Arg Gly Val Gly Lys Gln Gly Met His
1               5                   10                  15

Lys Ala Ala Arg Val Gly Arg Thr Gly Glu Arg Lys Gly Gly Lys His
                20                  25                  30

Arg Met (2) INFORMATION FOR SEQ ID NO: 13:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 13:

CGGGTCTACG CCTACGTCTT TGAACACCGT GCTTC                              35

(2) INFORMATION FOR SEQ ID NO: 14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 14:

CACAGGTCTG AGGAGCGATC CTGCTTGCTG                                    30

(2) INFORMATION FOR SEQ ID NO: 15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 15:

GGTTACACTG GCGGGCTCC                                                19

(2) INFORMATION FOR SEQ ID NO: 16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 16:

ATGGGTGAAG CCTGGGCAGG TG                                            22

(2) INFORMATION FOR SEQ ID NO: 17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 17:

GCCCAGGCTT CACCCAT                                                  17

(2) INFORMATION FOR SEQ ID NO: 18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 18:

AGACTGGGTA GATGATCAGA GACCTGAAAA CTACCG                             36

(2) INFORMATION FOR SEQ ID NO: 19:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 19:

GACAGGCCAG CTTGTGCTAT TGTTCTGAGT CTCAT                                35

(2) INFORMATION FOR SEQ ID NO: 20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 20:

ACCGTCCACC TGAACTGCTA CTGGGAGAAG                                      30

(2) INFORMATION FOR SEQ ID NO: 21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 21:

CGCTTACTAG GATCCAAGGC AAGCATGTAA                                      30

(2) INFORMATION FOR SEQ ID NO: 22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 22:

AGAAATGCAG GCGACCACGT G                                               21

(2) INFORMATION FOR SEQ ID NO: 23:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 23:

CAGGTCCAGA CTAACGTACT GCTGAGCCCC CGCCG                                35

(2) INFORMATION FOR SEQ ID NO: 24:

(i) SEQUENCE CHARACTERISTICS:
        (A) LENGTH: 374 base pairs
        (B) TYPE: nucleic acid
        (C) STRANDEDNESS: single
        (D) TOPOLOGY: linear (xi) SEQUENCE DESCRIPTION: SEQ ID NO: 24:

ACACGCTCGA CGAGGCGGAG CGCCAGTGGA AGGCCGAGTT CCACCGCTGG AGCTCCTACA      60

TGGTGCACTG GAAGAACCAG TTCGACCACT ACAGCAAGCA GGATCGCTGC TCAGACCTGT     120

GACCCCGGCG GGACCCCCAT GTCCTCCGCT CCGCCCGGCC CCCTAGCTGT ATATACTATT     180

TATTTCAGGG CTGGGCTATA ACACAGACGA GCCCCAGACT CTGCCCATCC CCACCCCACC     240

CCGACGTCCC CCGGGGCTCC CGGTCCTCTG GCATGTCTTC AGGCTGAGCT CCTCCCCGCG     300

TGCCTTCGCC CTCTGGCTGC AAATAAACTG TTACAGGCCA AAAAAAAAA AAAAAAAAA       360

AAAAAAAAAA AAAA                                                     374

(2) INFORMATION FOR SEQ ID NO: 25:

(i) SEQUENCE CHARACTERISTICS:
        (A) LENGTH: 40 amino acids
        (B) TYPE: amino acid
        (C) STRANDEDNESS: single
        (D) TOPOLOGY: linear (xi) SEQUENCE DESCRIPTION: SEQ ID NO: 25:

```
Asp Thr Leu Asp Glu Ala Glu Arg Gln Trp Lys Ala Glu Phe His Arg
1               5                   10                  15

Trp Ser Ser Tyr Met Val His Trp Lys Asn Gln Phe Asp His Tyr Ser
            20                  25                  30

Lys Gln Asp Arg Cys Ser Asp Leu
            35                  40
```

(2) INFORMATION FOR SEQ ID NO: 26:

(i) SEQUENCE CHARACTERISTICS:
        (A) LENGTH: 1215 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..78

(xi) SEQUENCE DESCRIPTION: SEQ ID NO: 26:

```
GGT ATG CAG GGG CCA GCG GGC AGC GGC TGG GAG GAG GGG AGT GGG AGC     48
Gly Met Gln Gly Pro Ala Gly Ser Gly Trp Glu Glu Gly Ser Gly Ser
        620                 625                 630

CCG CCA GGT GTA ACC CCT CTC TTC TCC CCC TAGCCTCGGA GGCTCCCAGC       98
Pro Pro Gly Val Thr Pro Leu Phe Ser Pro
        635                 640
```

ACCTGCCCAG GCTTCACCCA TGGGGAGGCT GCTCCGAGGC CCGGCCTCCC CCTGCCCCTC   158

CTCCTCCTCC ACCAGCTTCT CCTCCTCTTC CTCTCCCACC TCCGGCGGCT GTGAACACGG   218

CCTCTTCCCC TACGGCCTAC AGGGGCCCCT CCTCTAATGA GTGGTAGGAC CTGTGGGGAA   278

GGGCCCCACT CAGGGATCTC AGACCTAGTG CTCCCTTCCT CCTCAAACCG AGAGACTCAC   338

ACTGGACAGG GCAGGAGGAG GGGCCGTGCC TCCCACCCTT CTCAGGGACC CCCACGCCTT   398

TGTTGTTTGA ATGGAAATGG AAAAGCCAGT ATTCTTTTAT AAAATTATCT TTTGGAACCT   458

GAGCCTGACA TTGGGGAAG TGGAGGCCCG GAAACGGGGT AGCACCCCCA TTGGGGCTAT    518

AACGGTCAAC CATTTCTGTC TCTTCTTTTT CCCCCAACCT CCCCCTCCTG TCCCCTCTGT   578

TCCCGTCTTC CGGTCATTCT TTTCTCCTCC TCTCTCCTTC CTGCTGTCCT TCTCGGCCCC   638

GCCTCTGCCC TCATCCTCCC TCTCGTCTTT CGCACATTCT CCTGATCCTC TTGCCACCGT   698

CCCACGTGGT CGCCTGCATT TCTCCGTGCG TCCTCCCTGC ACTCATACCC CCCCTTCAAC   758

CCGCCCAAAT GTCCGATCCC CGACCTTCCT CGTGCCGTCC TCCCCTCCCG CCTCGCTGGG   818

CGCCCTGGCC GCAGACACGC TCGACACGCT CGACGAGGCG GAGCGCCAGT GGAAGGCCGA   878

GTTCCACCGC TGGAGCTCCT ACATGGTGCA CTGGAAGAAC CAGTTCGACC ACTACAGCAA   938

GCAGGATCGC TGCTCAGACC TGTGACCCCG GCGGGACCCC CATGTCCTCC GCTCCGCCCG   998

GCCCCCTAGC TGTATATACT ATTTATTTCA GGGCTGGGCT ATAACACAGA CGAGCCCCAG   1058

ACTCTGCCCA TCCCCACCCC ACCCCGACGT CCCCCGGGGC TCCCGGTCCT CTGGCATGTC   1118

```
-continued

TTCAGGCTGA GCTCCTCCCC GCGTGCCTTC GCCCTCTGGC TGCAAATAAA CTGTTACAGG    1178

CCAAAAAAAA AAAAAAAAAA AAAAAAAAAA AAAAAAA                             1215

(2) INFORMATION FOR SEQ ID NO: 27:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO: 27:

Gly Met Gln Gly Pro Ala Gly Ser Gly Trp Glu Glu Gly Ser Gly Ser
  1               5                  10                  15

Pro Pro Gly Val Thr Pro Leu Phe Ser Pro
            20                  25
```

TRANSGENIC NON-HUMAN MAMMALS PRODUCING A CHOLINESTERASE IN THEIR MILK

This application is a Continuation-In-Part of U.S. Ser. No. 08/370,156, filed Jan. 9, 1995, now U.S. Pat. No. 5,932,780 which is a Continuation-In-Part of U.S. Ser. No. 08/202,755 filed Feb. 28, 1994 now abandoned.

FIELD OF THE INVENTION

The present invention is generally in the field of cholinesterase enzymes and assays for anti-cholinesterase substances. More specifically, the present invention concerns new human acetylcholinesterase (AChE) encoding DNA sequences, which encode alternatively spliced forms of human AChE. The present invention also concerns use of these AChE sequences to provide transgenic animals which are capable of expressing human AChE, and which can be used to assay the effects of various anti-cholinesterase substances in vivo.

BACKGROUND OF THE INVENTION

Humans have two genes that encode acetylcholine-hydrolyzing enzymes, AChE and BChE (Soreq and Zakut, 1993). The AChE and BChE genes, although drastically different from each other in base composition, are thought to be derived from a common ancestral gene. AChE, mapped to chromosome 7q22 encodes the primary enzyme, acetylcholinesterase (AChE, E.C. 3.1.1.7), which terminates neurotransmission at synapses and neuromuscular junctions. BuChE, mapped to 3q26 encodes butyrylcholinesterase (BChE, E.C. 3.1.1.8), a homologous serum esterase with somewhat broader substrate specificity. BuChE acts as a scavenger of natural and man-made poisons, including organophosphate and carbamate pesticides, that are increasingly a threat to human health (Loewenstein et al., 1993). Yet, individuals with no BuChE activity (silent phenotype) in their serum are apparently healthy.

AChE acquires heterogeneous properties in different tumors distinct from those it displays in muscle and nerve, hemopoietic cells, embryonic tissue and germ cells. Monomers of the catalytic AChE subunit were observed in meningiomas and tetrameres in glioblastomas. Inhibition properties different from those of normal AChE were determined for serum AChE in various carcinomas. Moreover, tumorigenic expression of the corresponding AChE gene was found to be subject to variable control mechanisms. In differentiating neuroblastoma cells, inhibition of mevalonate synthesis, which decreases proliferation rates, increases AChE levels. In PC12 cells, in contrast, nerve growth factor induces the production of hydrophilic AChE, while embryonal, carcinoma cells and thyroid tumor cells produce this enzyme under all conditions examined.

A major hydrophilic form of AChE with the potential to be "tailed" by non-catalytic subunits is expressed in brain and muscle whereas a hydrophobic, phosphoinositide (PI)-linked form of the enzyme is found in erythrocytes. Two sublines of the human erythroleukemic K-562 cells were shown to express the PI-linked form of AChE, however, with different structural properties of the PI moiety. To reveal the molecular mechanisms underlying the heterogeneous tumorigenic expression of AChE, applicants initiated the investigation of alternative splicing in AChEmRNAs from different tumor cells.

Alternative splicing controls the generation of proteins with diverse properties from single genes through the alternate excision of intronic sequences from the nuclear precursors of the relevant mRNAs (Pre-mRNA). It is known to be cell type-, tissue- and/or developmental stage-specific and is considered as the principal mechanism controlling the site(s) and timing of expression and the properties of the resultant protein products from various genes.

Alternative exons encoding the C-terminal peptide in AChE were shown to provide the molecular origins for the amphiphilic (PI)-linked and the hydrophilic "tailed" form of AChE in Torpedo electric organ. The existence of corresponding alternative exons (Li et al., 1991) and homologous enzyme forms in mammals suggested that a similar mechanism may provide for the molecular polymorphism of human AChE. However, the only cDNAs reported to date from mammalian brain and muscle encode the hydrophilic AChE form (see Soreq et al., 1990). Nonetheless, RNA-protection and PCR analyses have demonstrated the existence of two rare alternative AChEmRNAs in mouse hemopoietic cells (Li et al., 1991).

More specifically, three alternative AChE-encoding mRNAs have been described in mammals. The dominant brain and muscle AChE found in NMJs (AChE-T) is encoded by an mRNA carrying exon E1 and the invariant coding exons E2, E3, and E4 spliced to alternative exon E6 (Li et al., 1991; Ben Aziz-Aloya et al., 1993). AChEmRNA bearing exons E1–4 and alternative exon E5 encodes the glycolipid phosphatidylinositol (GPT)-linked form of AChE characteristic of vertebrate erythrocytes (AChE-H) (Li et al., 1993; Legay et al., 1993a). An additional readthrough mRNA species retaining the intronic sequence I4 located immediately 3' to exon E4 was reported in rodent bone marrow and erythroleukemic cells (Li et al., 1993; Legay et al., 1993a) and in various tumor cells lines of human origin (Karpel et al., 1994). The tissue-specific posttranscriptional and posttranslational management of AChEmRNA and its polypeptide products raised the question of whether alternative C-terminal peptides play a role in mediating the accumulation of AChE in NMJs. It would be useful to be able to control drug distribution in vivo by targeting the neuromuscular junction or at other cites involving cholenergic receptors.

AChE is accumulated at neuromuscular junctions (Salpeter 1967) where it serves a vital function in modulating cholinergic neurotransmission (Reviewed by Soreq and Zakut, 1993). The molecular mechanisms by which AChE and other synaptic proteins are targeted to the NMJ are poorly understood. Compartmentalized transcription and translation in and around the junctional nuclei probably contribute to the NMJ localization of AChE (Jasmin et al., 1993). However, the high concentration of AChE at NMJs suggests that an additional step(s) may be required to actively direct this molecule to its ultimate synaptic destination. In that case, it is possible to postulate the existence of a unique molecular "tag" identifying AChE as NMJ-bound. Applicant has suggested the possibility that an evolutionarily conserved NMJ-targeting signal is embedded within the primary amino acid sequence of the major brain and muscle form of AChE (Ben Aziz-Aloya et al., 1993) but its exact sequence and activity when isolated was not known.

Anti-cholinesterase drugs are employed to treat a variety of frequently occurring diseases including Alzheimer's and Parkinson's diseases, glaucoma, multiple sclerosis, and myasthenia gravis (reviewed in Millard and Broomfield, In press). As a brief summary, glaucoma is a leading cause of blindness. Several different kinds of glaucoma exist, but the most common is primary open-angle glaucoma (POAG).

Because little is known conclusively about the etiology of this disease, present medical treatment is purely symptomatic. For at least thirty years, ophthalmologists have been treating advanced POAG with anti-ChE compounds. The most often-used has been echotiophate; other agents have included DFP, neostigmine, physostigmine, paraoxon and tetraethylpyrophosphate (TEPP).

Physostigmine was first reported to mitigate the autoimmune disease, myasthenia gravis (MG), and provided the basis of a diagnostic test that enabled detection of moderate forms of the disease. This work was the impetus for uncovering the cause of organophosphorus nerve agent toxicity and, sixty years later, quaternary carbamate compounds, such as neostigmine and pyridostigmine, are still used in the symptomatic treatment of MG to provide increased neuromuscular transmission and, to some extent, greater muscular strength. Edrophonium, a reversible anti-ChE, also improves MG by compensating for reduction of ACh receptors through elevation of neurotransmitter levels.

Senile demential of Alzheimer type (SDAT) is one of the most common causes of mental debilitation among the elderly. SDAT coincides with selective degeneration of basal forebrain cortical cholinergic neurons and "neurofibrillary tangles" contain both AChE and BuChE activity. Brain AChE activity apparently is reduced in SDAT. Several reports of specific reductions and increases in different brain AChE isoforms, as well as an abnormal SDAT-associated cerebrospinal fluid AChE isoelectric point variant have been reported. Because of the general destruction of normal presynaptic cholinergic fibersin SDAT, however, local changes in AChE may be quite distal to the cause of injury.

It has been suggested that a procedure to counter SDAT symptoms would be the inhibition of AChE to allow diffusion of ACh to become the rate limiting step of synaptic transmission and, hence, to conserve selectively the "functional" transmitter released. Thus, anti-ChEs would compensate for the diminished ACh released by the surviving cortical neurons. There was initial success in improving SDAT with arecoline and physostigmine but the latter was not sufficient to counteract completely the side-effects of inhibition. 1,2,3,4-tetraphydrop-9-aminoacridine (tacrine) has emerged as a candidate, but it is premature to conclude proof of efficacy and it is possible that it acts by stimulating ACh synthesis, as well as by inhibiting ChEs.

Furthermore, anti-cholinesterase poisons form a broad category of agricultural and household pesticides including organophosphorous and carbamide agents. Research and development directed toward the production of new specific, effective, low-toxicity drugs and insecticides are abundant. However, heretofore, no effective in vivo system has been developed which would allow for the rapid, effective and reliable screening of such anti-cholinesterase substances.

SUMMARY OF THE INVENTION

The present invention provides a substantially pure DNA sequence encoding acetylcholinesterase (AChE) selected from the group consisting of:
(a) genomic clones having a nucleotide sequence derived from the genomic region of a human AChE gene;
(b) cDNA clones having a nucleotide sequence derived from the sequence of the genomic clones of (a);
(c) DNA sequences capable of hybridization to the clones of (a) and (b) under moderately stringent conditions and which encode biologically active AChE; and
(d) DNA sequences which are degenerate as a result of the genetic code to the DNA sequences defined in (a), (b) and (c) and which encode biologically active AChE for use in piopharming.

The present invention also includes transgenic animals and a transgenic animal assay system. The present invention also provides the following transgenic animals:
(i) A transgenic animal carrying a recombinant DNA expression vector encoding a heterologous cholinesterase (ChE) enzyme selected from the group consisting of:
  (a) normal human AChE;
  (b) normal human BChE;
  (c) naturally-occurring variants of the AChE and BChE of (a) and (b);
  (d) synthetic variants of the AChE and BChE of (a) and (b), the synthetic variants selected from recombinantly-produced point-mutated and deletion, of one or more residues, mutations; and
  (e) normal insect ChEs, with the transgenic animal being capable of expressing substantial amounts of the ChE enzyme for studying control of production on biochemical properties of cholinesterases;
(ii) A transgenic animal of the invention as noted above which carries a recombinant expression vector encoding a human AChE or biologically active derivatives thereof selected from:
  (a) a DNA sequence which has all or part of the nucleotide sequence substantially as depicted in SEQ ID NO:1, and which encodes an amino acid sequence substantially similar or identical to all or part of the sequence of amino acid residues depicted in SEQ ID NO:2;
  (b) a DNA sequence which has all or part of the nucleotide sequences substantially as depicted in SEQ ID NO:3, and which encodes an amino acid sequence substantially similar or identical to all or part of the sequence of amino acid residues set forth in SEQ ID NO:4; and
  (c) a DNA sequence which has all or part of the nucleotide sequence substantially as depicted in SEQ ID NO:5, and which encodes an amino acid sequence substantially similar or identical to all or part of the sequence of amino acid residues set forth in SEQ ID NO:6;
(iii) A transgenic animal of the invention as noted above in which the recombinant expression vector contains a promoter controlling the transcription of the sequence encoding AChE selected from the group of eukaryotic host cell compatible promoters consisting of CMV, CMV-like, AChE and AChE-like promoters.

The present invention provides a transgenic animal assay system for studying secretion, control of production and biochemical properties of cholinesterase in mammalian milk.

The present invention also provides a method of treatment of acute traumatic injury by administering to a patient in need of such treatment a therapeutically effective amount of at least one of an antisense oligodeoxygnucleotide selected from the group consisting essentially of Seq. ID No. 1–6.

BRIEF DESCRIPTION OF THE DRAWINGS

FIG. 1A is a schematic representation of the DNA sequence of the human ACHE gene comprising the exons 2, 3, 4 and 6, as described in Example 1 (SEQ ID NO:1);

FIG. 1B is a schematic representation of the deduced amino acid sequence of human AChE, inferred from the sequence of FIG. 1A (SEQ ID NO:2);

FIG. 1C is a schematic representation of the DNA (SEQ ID NO:3) and deduced amino acid (SEQ ID NO:4) sequences of the alternatively spliced human AChE comprising the exons 2, 3, 4 and 5 as well as the translated portion of Intron 4 ("readthrough" I4-E5), as described in Example 1;

FIG. 1D is a schematic representation of the DNA (SEQ ID NO:5) and deduced amino acid sequences (SEQ ID NO:6) of the alternatively spliced human AChE comprising the exons 2, 3, 4, 5 and 6, as described in Example 1;

FIGS. 2(A, B) shows schematically the gene structure and restriction map of the human ACHE gene (A) and the DNA sequence and alternatively spliced products (SEQ ID NO:3) with respect, to the intron 4-exon 5 regions (B), as described in Example 1;

DETAILED DESCRIPTION OF THE INVENTION

Figure 3A:
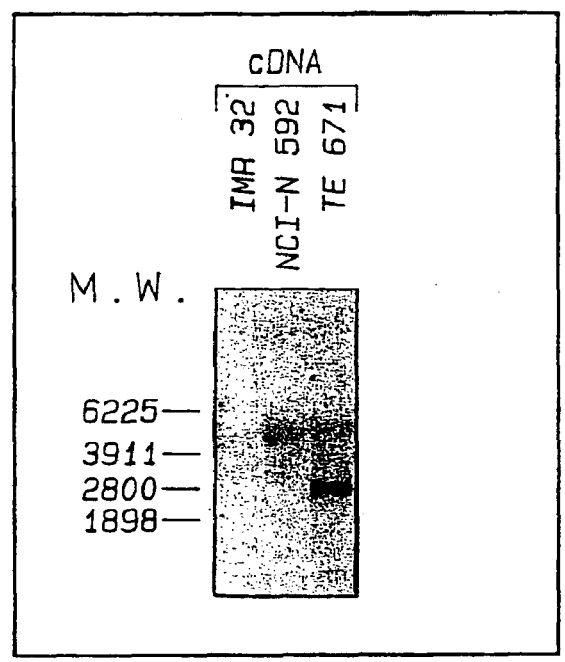
FIGS. 3(A, B) shows representations of the RNA-hybridization blots of various tumor-derived AChEmRNAs probed with ACHEcDNA (A) or a E5 (exon 5)-specific (B) probes, as described in Example 1.

The present invention is based on the surprising and unexpected findings, as detailed herein below, that it is possible to obtain transgenic animals, e.g. mice, *Xenopus* embryos, goats, cows and pigs that are capable of expressing human cholinesterases (e.g. AChE) in substantial amounts. Accordingly, these transgenic animals may be employed for the rapid and efficient screening in vivo of anti-cholinesterase substances such as organophosphates, carbamates, anti-cholinesterase drugs, etc. to determine whether such substances are:

(i) potentially harmful to normal individuals;

(ii) potentially useful as therapeutic agents in anti-cholinesterase indications; and (iii) capable of being scavenged or blocked by modified (natural or synthetic variants) human AChEs or BChEs. This would provide for testing of new AChEs or BChEs that may be used therapeutically for treating individuals exposed to dangerous levels of such substances and where their own endogenous AChEs or BChEs cannot effectively block such toxins.

Further, the present invention is also, as detailed herein below, based on the surprising and unexpected findings that the human AChE gene actually encodes three alternatively spliced products, each of which has a distinct biological activity (Example 1). In accordance with the present invention, it has also been surprisingly found that in different tumor cell lines, there is expression of two alternative AChEmRNA species, in addition to the major species expressed in brain and muscle, and suggest the presence of three distinct forms of AChE, two of which may be PI-bound to the cell surface, in several types of malignant cells.

The present invention provides a substantially pure DNA sequence encoding acetylcholinesterase (AChE) selected from the group consisting of:

(a) genomic clones having a nucleotide sequence derived from the genomic region of a human AChE gene;

(b) cDNA clones having a nucleotide sequence derived from the sequence of the genomic clones of (a);

(c) DNA sequences capable of hybridization to the clones of (a) and (b) under moderately stringent conditions and which encode biologically active AChE; and (d) DNA sequences which are degenerate as a result of the genetic code to the DNA sequences defined in (a), (b) and (c) and which encode biologically active AChE.

Preferred embodiments of the above DNA sequence of the invention are:

(i) a DNA sequence of the invention as noted above wherein the sequence encodes human AChE or biologically active derivatives thereof;

(ii) a DNA sequence of the invention as noted above which has all or part of the nucleotide sequence substantially as set forth in SEQ ID NO:1, and which encodes an amino acid sequence substantially similar or identical to all or part of the sequence of amino acid residues set forth in SEQ ID NO:2;

(iii) a DNA sequence of the invention as noted above which has all or part of the nucleotide sequences substantially as set forth in SEQ ID NO:3, and which encodes an amino acid sequence substantially similar or identical to all or part of the sequence of amino acid residues set forth in SEQ ID NO:4; and (iv) a DNA sequence of the invention as noted above which has all or part of the nucleotide sequence substantially as set forth in SEQ ID NO:5, and which encodes an amino acid sequence substantially similar or identical to all or part-of the sequence of amino acid residues also set forth SEQ ID NO:6.

The present invention also provides as a preferred embodiment recombinant expression vectors containing any of the above-mentioned DNA sequences of the invention. The recombinant vectors may be any of the well-known eukaryotic expression vectors, and their construction is by any of the standard recombinant DNA (genetic engineering) procedures, such vectors and procedures now being standard to all skilled practitioners. Further, the promoters used in the above vectors to control transcription of the AChE encoding sequences, may also be any of the well-known eukaryotic host cell-compatible promoters (e.g. animal virus, yeast, mammalian promoters). The preferred promoters are the CMV, CMV-like, human AChE and human AChE-like promoters having similar transcription factor binding sites within the promoter region sequence.

Another preferred embodiment of the invention is a eukaryotic host cell transformed by any of the above recombinant vectors of the invention, the host cell being capable of producing (expressing) AChE under suitable culture conditions. Here too, the host cells may be any of the well-known eukaryotic cultured cell lines e.g. yeast, Chinese hamster ovary, etc. The culture conditions for such host cells are the standard well elaborated ones, with standard modifications, if necessary, to ensure that when high levels of AChE are expressed, this will not lead to substantial cell death.

The present invention also provides for a purified and isolated 40-amino acid C-terminal peptide (SEQ ID No:25) encoded by exon E6 (SEQ ID No:24) and its biologically active analogs. An analog will be generally at least 70% homologous over any portion that is functionally relevant. In more preferred embodiments the homology will be at least 80% and can approach 95% homology to the sequence. The amino acid sequence of an analog may differ from that of the C-terminal peptide when at least one residue is deleted, inserted or substituted. Differences in glycosylation can provide analogs.

The present invention also includes a recombinant expression vector comprising a DNA sequence which encodes the peptide as set forth in SEQ ID No:24. Examples of forming such vectors and their use are set forth in Examples 2 and 3 herein below. Such vectors are known or can be constructed by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids, liposomes and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found as generally described in Sambrook et al., *Molecular Cloning: A Laboratory Manual*, Cold Springs Harbor Laboratory, New York (1992), in Ausubel et al., *Current Protocols in Molecular Biology*, John Wiley and Sons, Baltimore, Md. (1989), and include, for example, stable or transient transfection, lipofection, electro-poration and infection with recombinant viral vectors. Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector for introducing and expressing recombinant sequences is the adenovirus derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur. Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted and will be known to those skilled in the art. For example, if breast cancer is to be treated then a vector specific for such epithelial cells would be used. Likewise, if diseases or pathological conditions of the hematopoietic system are to be treated, then a viral vector that is specific for blood cells and their precursors, preferably for the specific type of hematopoietic cell, would be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject or microinjection into eggs. Injection of the viral vectors into a spinal fluid can also be used as a mode of administration, especially in the case of neuro-degenerative diseases. Following injection, the viral vectors will circulate until they recognize host cells with the appropriate target specificity for infection.

An alternate mode of administration can be direct inoculation locally at the site of the disease or pathological condition or by inoculation into the vascular system supplying the specific organ with nutrients. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes can also be used to introduce the non-viral vectors described above into recipient cells within the inoculated area. Such transfection vehicles are known by one skilled within the art.

The present invention also provides a method of either targeting or excluding specific molecules or compounds from the neuromuscular junction or synapses as more precisely set forth in Example 7 herein below. In a preferred embodiment, cholinergic junctions are targeted. To target proteins or other molecules to the neuromuscular junction or synapses, the method includes the steps of coupling a 40-amino acid C-terminal peptide (SEQ ID No:24) and its biologically active analogs to a compound and administering the coupled peptide-compound. For example, anticholinesterases such as mestinon can be delivered directly to the neuromuscular junction in Myasthenia gravis. AChE can be delivered in organophosphate exposure.

For exclusion, the present invention provides a readthrough AChEmRNA with a sequence as set forth in SEQ ID NO:26 derived from AChE-I4/I5 and the peptide product (SEQ ID No:27) encoded by the AChEmRNA as set forth in SEQ ID No:26. The method of excluding compounds from the neuromuscular junction or synapses includes the steps of coupling a peptide as set forth in SEQ ID No:27 to a protein and administering the coupled protein.

ACHEmRNA bearing the alternative 3' exon E6 induced specific accumulation of nascent human AChE in muscle and neuromuscular junctions of transiently transgenic *Xenopus laevis* embryos as shown in Example 7. Replacement of E6 with an in-frame pseudo-intronic sequence of similar size directed production of a soluble enzyme species that was not incorporated into muscle or NMJs, but was amassed in epidermal cells and excreted into the external culture medium. These observations suggest that the 40-amino acid C-terminal peptide (SEQ ID No:24) characteristic of the brain and muscle AChE subtype plays an indispensable role in the NMJ localization of human AChE.

The findings of the present invention indicate that exon E6 and/or its encoded peptide participate in forming a recognition signal(s) through which such putative cellular elements might mediate accumulation and subcellular localization of AChE. However, search of the GCG data bank did not reveal significant homologies between the E6-encoded peptide and any protein except the related acetylcholine-hydrolyzing enzyme butyryl-cholinesterase. It is interesting to note that this enzyme, which shares high homology (56%) with AChE in the corresponding C-terminal domain, also accumulated in NMJs of microinjected *Xenopus* embryos. Thus, applicants' findings suggest that exon E6 defines a conserved motif for muscle accumulation and trafficking of cholinesterases.

The findings of the present invention also indicate that there is induction of neuropathological changes mediated by the non-catalytic properties of AChE and by its variable C-terminus. More specifically, both catalytically active and inactive AChE induce the degeneration of cortical pyramidal cells after administration of phencyclidine (PCP), an N-methyl-D-aspartate (NMDA) receptor blocker, whereas the extrasynaptic I4-AChE variant was far less effective.

Furthermore, the findings of the present invention indicate a corkscrew phenotype in AChE transgenic mice. This phenotype is induced in degenerating cortical pyramidal cells after the administration of phencyclidin, thus exposing pyramidal cells to excessive cholinergic excitation. Accordingly, these findings demonstrate the induction of neurological changes which are mediated by the non-catalytic properties of AChE and further affected by its variable C-terminal.

An mRNA representing the I4 readthrough transcript was reported in mouse tissues, but considered absent in human cells (Li et al., 1993). This difference was attributed to an inherent property of the human ACHE nucleotide sequence (Li et al., 1993). Nonetheless, applicants have recently observed, using RT-PCR and I4-specific primers, mRNA carrying the retained I4 sequence, in addition to E5 and E6, in several tumor cell lines of human origin (Karpel et al., 1994).

The present invention also provides a method of using antisense therapeutics for the prevention of neuronal damage following head trauma. More specifically, this method includes utilizing antisense therapeutics for the prevention of AChER overproductions thus limiting the detrimental consequences of various traumas to the nervous system. As shown in Example 8, adult mice were subjected to closed head injury and treated either with PBS or a protected antisense oligonucleotide targeted AChE mRNA into the site of injury. Fourteen days after the injury, the mice were sacrificed and analyzed. The mice treated with antisense oligonucleotide targeted to AChE mRNA showed suppression of the AChER mRNA in the neurons. Further, upon staining the Golgi of the dendrites, the effect of the antisense oligonucleotide targeted to AChE mRNA there was significantly less staining. Therefore, fewer neurons were lost as a result of this treatment. Accordingly, similar antisense therapeutics can be utilized in treating acute traumatic injury by preventing AChER overproduction and therefore limiting the consequences of traumatic injury to the nervous system.

The targeted compound is administered and dosed in accordance with good medical practice, taking into account the clinical condition of the individual patient, the site and method of administration, scheduling of administration, and other factors known to medical practitioners. The "effective amount" for purposes herein is thus determined by such considerations as are known in the art. In general, the amount must be effective to achieve improvement including but not limited to improved survival rate, more rapid recovery, or improvement or elimination of symptoms and other indicators as are selected as appropriate measures by those skilled in the art.

In the method of the present invention, the targeted compound can be administered in various ways. It should be noted that the targeted compound can be administered as the compound or as pharmaceutically acceptable salt and can be administered alone or in combination with pharmaceutically acceptable carriers. The compounds can be administered orally, subcutaneously or parenterally including intravenous, intraarterial, intramuscular, intra-peritoneally, and intranasal administration. Implants of the compounds are also useful. The patient being treated is a warm-blooded animal and, in particular, mammals including man.

It is noted that humans are treated generally longer than the mice exemplified herein which treatment has a length proportional to the length of the disease process and drug effectiveness. The doses may be single doses or multiple doses over a period of several days.

When administering the targeting compound parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any carrier, vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the targeting compound can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as polymer matrices, liposomes, and microspheres. An implant suitable for use in the present invention can take the form of a pellet which slowly dissolves after being implanted or a biocompatible delivery module well known to those skilled in the art. Such well known dosage forms and modules are designed such that the active ingredients are slowly released over a period of several days to several weeks.

A pharmacological formulation of the targeting compound utilized in the present invention can be administered orally to the patient. Conventional methods such as administering the compounds in tablets, suspensions, solutions, emulsions, capsules, powders, syrups and the like are usable. Known techniques which deliver orally or intravenously and retain the biological activity are preferred.

For delivery within the CNS, pharmacological formulations that cross the blood-brain barrier can be administered (Betz et al., 1994) or direct injection into the spinal fluid. Such formulations can take advantage of methods now available to produce chimeric peptides in which the present invention is coupled to a brain transport vector allowing transportation across the barrier. (Pardridge, et al., 1992; Pardridge, 1992; Pardridge, et al., 1993).

The present invention also provides transgenic animals and a transgenic animal assay system. The present invention provides the following transgenic animals:

(i) A transgenic animal carrying a recombinant DNA expression vector encoding a heterologous cholinesterase (ChE) enzyme selected from the group consisting of:

(a) normal human AChE;
(b) normal human BChE;
(c) naturally-occurring variants of the AChE and BChE of (a) and (b);
(d) synthetic variants of the AChE and BChE of (a) and (b), the synthetic variants selected from recombinantly-produced point-mutated and deletion, of one or more residues, mutations; and
(e) normal insect ChEs, with the transgenic animal being capable of expressing substantial amounts of the ChE enzyme;

(ii) A transgenic animal of the invention as noted above which carries a recombinant expression vector encoding a human AChE or biologically active derivatives thereof selected from:

(a) a DNA sequence which has all or part of the nucleotide sequence substantially as depicted in SEQ ID NO:1, and which encodes an amino acid sequence substantially similar or identical to all or part of the sequence of amino acid residues depicted in SEQ ID NO:2;
(b) a DNA sequence which has all or part of the nucleotide sequences substantially as depicted in SEQ ID NO:3, and which encodes an amino acid sequence substantially similar or identical to all or part of the sequence of amino acid residues set forth in SEQ ID NO:4; and
(c) a DNA sequence which has all or part of the nucleotide sequence substantially as depicted in SEQ ID NO:5, and which encodes an amino acid sequence substantially similar or identical to all or part of the sequence of amino acid residues set forth in SEQ ID NO:6;

(iii) A transgenic animal of the invention as noted above in which the recombinant expression vector contains a promoter controlling the transcription of the sequence encoding AChE selected from the group of eukaryotic host cell compatible promoters consisting of CMV, CMV-like, ACHE and ACHE-like promoters.

The transgenic animal assay system of the present invention provides for determining the anti-cholinesterase activity of substances selected from the group consisting of: organophosphates, carbamates, anti-cholinesterase drugs, plant glycoalkaloids and snake venoms, and comprises a transgenic animal of the invention as noted above. The preferred transgenic animals are *Xenopus* embryos and mammals, such as mice, cows, goats, pigs and sheep.

In this transgenic assay system, any of the above animals can be used. For example, mammals and *Xenopus* are advantageous. Mammals are advantageous since they are physically closer to humans. Owing to their large size and resilience, *Xenopus* eggs are easily manipulated and have proven amenable to a variety of experimental manipulations, including heterologous gene expression through microinjection protocols. Fertilized eggs develop rapidly to yield a tailbud embryo with a functional neuromuscular system within 48 hours. By day 3 post-fertilization (PF), reflexive swimming is observed, and continued embryonic development gives rise to a free-swimming tadpole 4–5 days PF. Two-three day old *Xenopus* embryos can already be exposed to the anti-cholinesterase substances to be tested. Thus, the rapid development of the neuromuscular system in *Xenopus* makes it an excellent in vivo model for the study of vertebrate myogenesis and synaptogenesis.

Applicants have previously cloned a DNA sequence encoding human AChE and used it to express catalytically active AChE in microinjected *Xenopus* oocytes (Soreq et al., 1990) and cultures human cells (Velan et al., 1991a). Placed downstream of either the native human AChE gene promoter or the cytomegalovirus (CMV) enhancer-promoter and introduced into fertilized *Xenopus* eggs, this DNA led to overexpression of AChE in NMJs of two-day old embryos (Ben Aziz-Aloya et al., 1993).

In contrast to the above mentioned, the present invention concerns the cloning and expression in transgenic animals of constructs encoding the various alternatively spliced recombinant human AChE (rHAChE) of the invention, and also the cloning and expression of AChE in animals in the transgenic assay system of the invention. Moreover, the persistence of the overexpressed rHAChE enzyme in neuromuscular junctions (NMJs) has also been shown, in accordance with the present invention, to persist to at least day 3 of embryonic development.

The present inventors have also recently cloned the natural variants of the BChE gene into *Xenopus* and have prepared site-directed mutants of this gene, also cloned into *Xenopus* (see Neville et al., 1992). Thus, a very wide range of DNA constructs encoding natural and synthetic (e.g. site-directed mutants, truncated e.g. active fragments, alternatively spliced) human AChEs and BChEs can be prepared by the methods set forth hereinbelow (and in Neville et al., 1992), and used to prepare transgenic *Xenopus* embryos and mice as set forth herein below. These transgenic animals may then be used for screening anti-cholinesterase substances, to determine:

(i) the toxicity of such substances if such are intended, for example, for use as pesticides;

(ii) the effectivity and specificity of anti-cholinesterase drugs intended for treatment of various diseases; and (iii) whether various natural or synthetic AChEs or BChEs (or active fragments thereof) may be more useful than others as agents for treating individuals exposed to toxic levels of anti-cholinesterase substances.

Moreover, the present inventors (see Ben Aziz-Aloya et al., 1993) have also recently analyzed the human ACHE promoter in detail and have discovered a large number of transcription control sites within this promoter region. Accordingly, by use of this promoter in DNA constructs encoding the above AChEs, it is possible in the transgenic animals, also to determine whether substances can affect AChE expression at the level of transcription, i.e. whether the observed inhibition is via inhibition of the enzyme itself or the production of the enzyme.

Furthermore, it is also possible in the same way to analyze substances, i.e. various transcription-initiation factors, which can induce AChE production by increasing the levels of transcription, i.e. substances which bind to the promoter and cause increased transcription of the ACHE gene. Such substances will therefore be useful as agents for treating individuals exposed to dangerous levels of anti-cholinesterase substances.

In the transgenic assay systems, the *Xenopus* embryo system. (see Example 2) is advantageous with respect to the time course of the assay procedure, i.e. it is experimentally easy to handle *Xenopus* oocytes, fertilize them, microinject them with DNA constructs and obtain relatively large numbers of transgenic embryos, which develop rapidly to yield a functional neuromuscular system within 48 hours, at which stage they may be used to screen the substances as noted above. Further, as noted in Example 2 (and in Ben Aziz-Aloya et al., 1993) DNA constructs encoding human AChE with either the CMV or human promoter are effective in causing overexpression of AChE in *Xenopus*.

The transgenic mice system is advantageous in that it provides an in vivo model system which is closer to humans physiologically.

In view of this, it is also envisioned that the transgenic systems may be used in parallel or one after the other, for example, for rapid screening of a large number of substances, the transgenic *Xenopus* system may be employed, those substances of greater interest than being tested on the corresponding transgenic mice.

As regards assay procedures to be used in the various transgenic systems, these are as described for the transgenic animals (Examples 2, 3, 6 and 7). In addition, assays for enzymatic hydrolysis of butyrylthiocoline (BuTCh) or acetylcholine (ACh) by BChE and AChE respectively have been detailed in Loewenstein et al., 1993.

In the transgenic assay system, the assay is performed in *Xenopus* in the following way: The transgenic embryos are allowed to grow and are then exposed to the prospective substance in the incubating medium in a dose and time dependent manner. The rate of mortality of the embryos and in vivo inhibition of the expressed human AChE would indicate the anti-cholinesterase activity of the substance. Post-mortem analysis of the drug-treated transgenic embryos may reveal correlation between the mortality rate and inhibition of the enzyme in target tissue; or whether the enzyme (i.e. naturally occurring or synthetic form) expressed in the embryos constitutes an in vivo target for the tested substance and whether adding protein (i.e. AChE, BChE) would afford protection against the substance and at what levels of the substance such added protein would be necessary.

The present invention also provides a transgenic animal assay system in mice which provides a model system for testing for, and treatments of, cholinergic deficits in mammals as set forth in Example 6 such as cognitive functioning in Alzheimer's patients, thermoregulation, amyotrophic lateral sclerosis.

The assay system of the present invention allows the exploration of the formation and functioning of cholinergic brain synapses. Imbalanced cholinergic signaling is associated with a number of neuronal disorders, including Alzheimer's and Parkinson's (Wurtman, 1992). This imbalance includes deficits in acetylcholine (Coyle et al, 1983), reduced levels of cholinergic receptors and modified numbers and size of synapses in patient's brains (Newhouse et al, 1994). Examples 2–5 herein below provide evidence that the transgenic assay system, and in particular, the transgenic mouse of the present invention provides a model with these parameters which can be used for screening treatments for diseases with imbalanced cholinergic signaling. To confirm this and further extend the validity of the model, the effects of DFP, the muscarinic agonist oxotremorine, nicotine and the serotonergic agonist 8-OH-DPAT, were studied in the model. Further, the spatial learning ability and memory of the transgenic mice were also tested as well as their response to tacrine, as tacrine is the first drug approved by the FDA for use in Alzheimers disease.

Example 6 sets forth the results of these studies and confirms the validity of the transgenic assay system. The transgenic mice displayed relative resistance to the hypothermic effects of DFP, the muscarinic agonist oxotremorine, nicotine and the serotonergic agonist 8-OH-DPAT indicating that the overexpressed enzyme conferred physiological changes in drug responses and that additional key protein(s) involved in such responses were modulated. In water maze tests the transgenic mice displayed inpairments in spatial learning and memory. Thus these AChE overexpressing mice provide a mammalian model where both physical and cognitive cholinergic responses are amenable for testing.

The present invention also provides a transgenic animal assay system in mice which provides a model system for studying the secretion, control of production and biochemical properties of cholinesterases in mammalian milk. Additionally, this animal model provides further opportunities for improvements in biopharming.

More specifically, the present invention provides a transgenic mammal, which is capable of expressing substantial amounts of the human ChE enzyme This concept, which is commonly known as "biopharming" allows a substantial amount of the desired enzyme to be produced in a relativey short period of time using the host animal as a "factory". That is, the host animal is genetically altered to be able to produce increased quantities of a product. As shown in Example 10, transgenic mammals are able to produce large quantities of human ChE in their mammary glands. The human ChE which is expressed in the mammary glands of the transgenic animal, is excreted in the milk. Thus, lactating transgenic female mammals can be used to produce human ChE, particularly human AChE, by milking the mammals and isolating the enzyme from the milk by techniques known to the skilled biotechnologist.

Further, the ChE that has been isolated from the milk, which was produced elucidated the same results as the naturally occurring product. Three different isoforms of AChE were studied using constructs (Seq. ID No. 28). Additional, the AChE activity patterns indicate that the AChE is thermostable at mammalian temperatures, thus indicating the feasibility of producing AChE in transgenic mammals.

EXAMPLES

The present invention will now be described in more detail in the following non-limiting examples and the accompanying figures.

General Procedures and Materials (a) Cell lines, tumor biopsies and tissue sources. The NT2/D1 teratocarcinoma cells were grown as in Andrews, 1988. The H9 T lymphocytoma, IMR32 neuroblastoma, 293 embryonal kidney cells, and TE671 medulloblastoma cells were received from the American Type Culture Collection and grown according to the provided instructions. NCI-N-592 small cell lung carcinoma cells were grown as detailed elsewhere (Sher et al., 1990). The hemopoietic cell lines K-562 HL60 and DAMI (Greenberg, et al., 1988) were gratefully received from E. Kedar (Hebrew University of Jerusalem, Israel), Y. Yarden (Weizmann Institute of Science, Rehovot, Israel) and A. Eldor (Hebrew University of Jerusalem, Israel), respectively. Tumor biopsies from serous ovarian adenocarcinoma, moucinous cyst adenoma, papillary adenocarcinoma and benign myoma were removed at surgery in the Department of Obstetrics and Gynecology at the Edith Wolfson Medical Center and were pathologically characterized according to established procedures. Control tissues from fetal and adult individuals were obtained as previously detailed (Zakut et al., 1990).

(b) in vitro fertilization and microinjections. DNA microinjections into Xenopus laevis oocytes and fertilized eggs were essentially as previously described (Ben Aziz-Aloya et al., 1993). Fertilized eggs were dejellied with 2% cysteine, and injected within the first 2 cleavage cycles in medium containing 5% ficoll in 0.3×MMR. Several hours after microinjection, embryos were transferred into 0.3×MMR and cultured overnight at 17–19° C. One-day old embryos were transferred to either 0.1×MMR or aged tap water and cultured for an additional 1–3 days.

(c) Activity Assays. Embryos were harvested in groups of 3–5 apparently normal individuals and stored frozen until used. Homogenates were prepared in a high salt/detergent buffer (0.01M Tris, 0.1M NaCl, 1% Triton X-100, 1 mM EGTA (pH 7.4); 150 µl/embryo) and assayed for enzymatic activity as detailed elsewhere (Neville et al., 1992). For subcellular fractionations, groups of 3 embryos were homogenized in LS buffer (0.02M Tris-HCl (pH 7.5), 0.01M MgCl$_2$, 0.05M NaCl; 100 µl/embryo) and centrifuged at 100,000 rpm for 10 minutes in a Beckman TL100 tabletop ultracentrifuge. The supernatant was collected and considered the low salt-soluble fraction. The pellet was resuspended in LSD buffer (0.01M phosphate buffer (pH 7.4), 1% Triton X-100), incubated on ice for 1 hour and centrifuged as above for 5 minutes to generate the detergent soluble fraction. The remaining pellet was resuspended in HS buffer (0.01M phosphate buffer (pH 7.4), 1.0M NaCl, 1 mM EGTA) to release the high salt-soluble AChE fraction.

Other methods not expressly disclosed can be found as generally described in Sambrook et al.; *Molecular Cloning: A Laboratory Manual*, Cold Springs Harbor Laboratory, New York (1992), in Ausubel et al., *Current Protocols in Molecular Biology*, John Wiley and Sons, Baltimore, Md. (1989).

Example 1

Analysis of the Acetylcholinesterase Gene Sequence, the mRNAs Transcribed Therefrom and the Translation Products of the mRNAs (a) cDNA and genomic clones and DNA sequencing. The genomic GNAChE clone and the HAChE recombinant transcription construct were as described (Soreq, et al., 1990). Deletion of 94 bp from HAChE at position 1616–1710 by BamHI excision and religation created the control plasmid HdAChE for the quantitative RNA-PCR experiments.

Double and single stranded DNA was sequenced as detailed previously (Soreq, et al., 1990), except that annealing of AChE-specific sequencing primers was initiated at 72° C. to circumvent the high G,C-rich content of the analyzed sequences. Also, the sequencing primers were closely spaced and reading of the sequence included comparison of sequence data from both directions and with variable distances from the primers employed.

(b) PCR primers and the RNA-PCR procedure. The following PCR primers were employed:
1) E3/1522(+) 5'-CGGGTCTACGCCTACGTCTTTGAACACCGTGCTTC-3' (SEQ ID NO:13)
2) E6/2003(−) 5'-CACAGGTCTGAGCAGCGATCCTGCTTGCTG-3' (SEQ ID NO:14)
3) 14/1939(−) 5'-GGTTACACTGGCGGGCTCC-3' (SEQ ID NO:15)
4) E5/1917(−) 5'-ATGGGTGAAGCCTGGGCAGGTG-3' (SEQ ID NO:16)
5) E5/1900(+) 5'-GCCCAGGCTTCACCCAT-3' (SEQ ID NO:17)
6) 1281(+) 5'-AGACTGGGTAGATGATCAGAGACCTGAAAACTACCG-3' (SEQ ID NO:18)
7) 1635(−) 5'-GACAGGCCAGCTTGTGCTATTGTTCTGAGTCTCAT-3' (SEQ ID NO:19)
8) 1565(+) 5'-ACCGTCCACCTGAACTGCTACTGGGAGAAG-3' (SEQ ID NO:20)
9) 1887(−) 5'-CGCTTACTAGGATCCAAGGCAAGCATGTAA-3' (SEQ ID NO:21)

10) E5/2519(-) 5'-AGAAATGCAGGCGACCACGTG-3' (SEQ ID NO:22)

For the positions of primers No. 1–5 and 10 along the AChE gene see FIG. 3. Butyrylcholinesterase (BCHE, primers Nos. 6, 7) and CHED primers (primers Nos. 8, 9) were numbered according to previously published sequence data (Prody et al., 1987; Lapidot-Lifson et al., 1992, respectively).

For RNA-PCR analyses, total RNA was extracted by the guanidinium thiocyanate method as described (Soreq et al., 1990). Random hexamer primers (Boehringer, Mannheim, Germany) were employed for cDNA preparation from 0.1 $\mu$g RNA of each sample using the MMLV reverse transcriptase (r.t.) (Gibco, BRL, Bethesda, Md.), essentially as described elsewhere (Lapidot-Lifson et al., 1992). PCR amplification in the 9600 Thermal Controller (Perkin-Elmer/Cetus, Norwalk, Conn.) (39 cycles) was performed using the noted primer pairs as follows: Denaturation 94° C., 1 minute (first step 2 minute), annealing 65° C., 1 minute and synthesis 72° C., 1 minute (last cycle 5 minutes). Amplification products (20%) were electrophoresed (7 Volts.cm, 60 minutes) on 1.6% agarose (IBI, CT) gel containing ethidium bromide (0.5 $\mu$g/ml, Sigma) with TAE (40 mM Tris-acetate, 2 mM EDTA) as electrophoresis buffer, and were photographed under 320 nm illumination. Control reactions, without r.t., remained negative, proving the absence of contaminating DNA sequences corresponding to the relevant mRNA sequences.

Figure 1B-1:
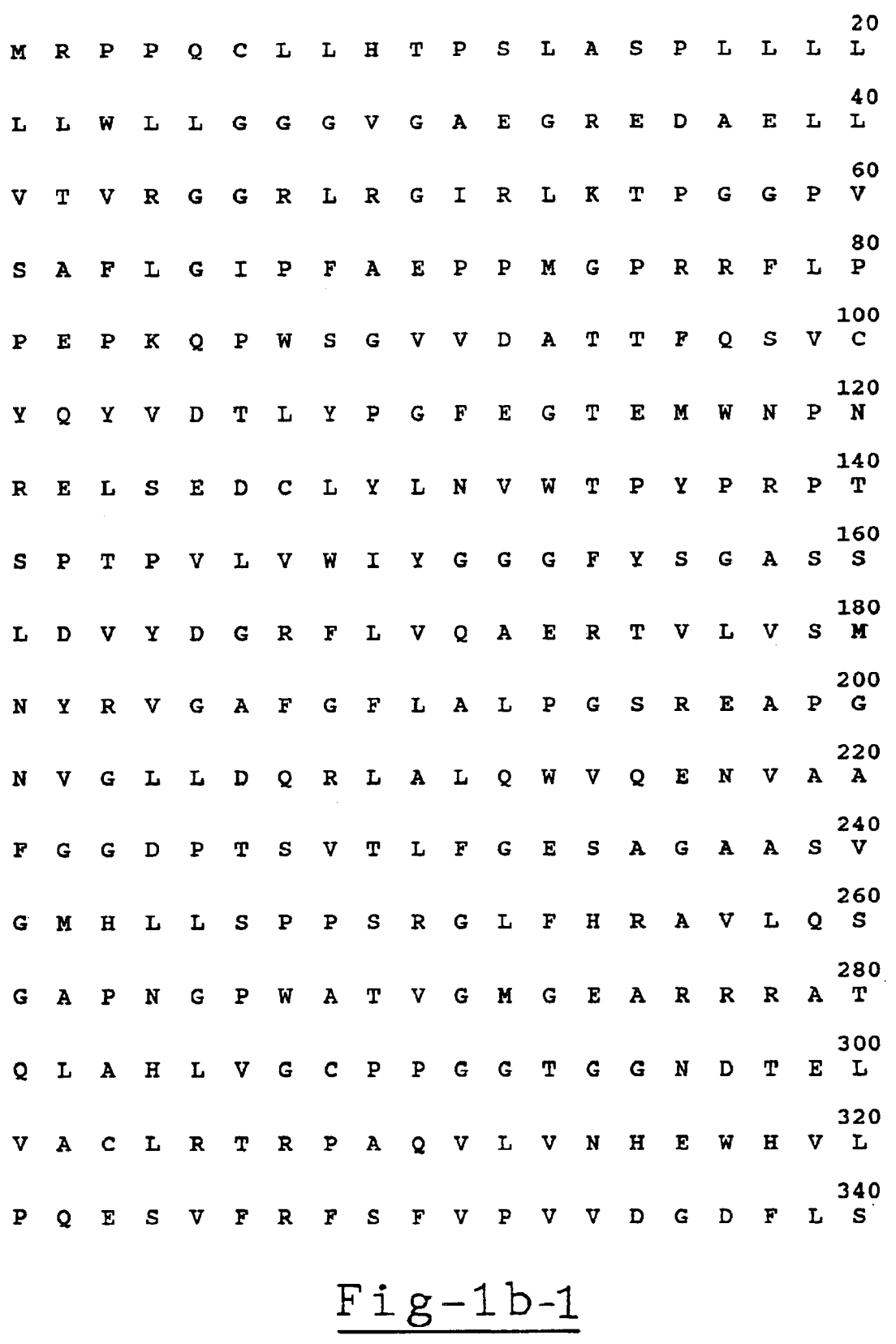

(c) Sequence Analysis. In FIG. 1(A–D) there is shown the DNA sequence (SEQ ID NO:1) (A), the deduced (from the sequence in A) amino acid sequence (SEQ ID NO:2) (B), the DNA and amino acid sequence (SEQ ID NOS:3–4) (C) of the so-called "readthrough" region or domain consisting of intron 4-exon 5 (I4-E5) contained in the sequence of A, and the exon 5 (E5) sequence (SEQ ID NOS:5–6) (D), of the cloned human AChE gene. In FIGS. 2(A, B) there is shown, schematically, the structure of the human AChE gene (A) and the sequence of the I4-E5 domain. As is depicted in FIG. 2A, the human AChE gene includes a promoter region (black), six exons, designated in this scheme E1–E6 and four introns, I1–I4 the sizes of which are noted on the length scale in kilobase (Kb) where the first sequenced nucleotide equals -0-. Lengths of introns and characteristic restriction sites (S-SacI, X-XhoI, A-AccI, K-KpnI, P-PvuII, SP-SpjI, ST-StuI, H-HincII) within the human genomic AChE clone, called clone GNAChE (Soreq et al., 1990) were determined as detailed elsewhere (Ben Aziz-Aloya et al., 1993). The I4-E5 domain is framed black. With respect to the I4-E5 domain, FIG. 2B (and FIG. 1C) shows the nucleotide sequence of this domain, in which, in FIG. 2B (SEQ ID NO:3), the nucleotides are numbered on the right hand side. Analysis of this region using the MAP program (University of Wisconsin) revealed a continuous open reading frame (ORF) connecting the E4-I4-E5 region. The predicted polypeptide diverts from the common AChE sequences at amino acid residue 544, the numbering of the amino acids being on the left hand side of the sequence and being in respect to the entire AChE protein sequence. The I4 translated peptide (white letters on black background) and the cleavable C-terminal peptide (amino acids nos. 584–612, shaded) are presented. E4 and E6 splice sites are marked by arrows. Starred amino acid residues (*DTL) are translated from the E6 domain.

Thus, as shown in FIGS. 1(A–D) (SEQ ID Nos:1–6) and FIGS. 2(A, B), the sequencing of the cloned human AChE gene revealed a 829 base pairs (bp) long domain (I4-E5) which operates as an intron between exons 4 and 6 (for nomenclature see Massoulie et al., 1992) and is spliced out in the AChEmRNA form expressed in brain and muscle (Soreq et al., 1990). Sequence analysis demonstrated the presence of the consensus splicing motifs GA (at position 11) and GT (at position 87) with a preceding pyrimidine stretch. This implied that nucleotides 11–87 in this region constitute an intron, designated I4, whereas the remaining sequence (nucleotides 88–839) represents an additional exon, designated E5. The human I4 intron constitutes an open reading frame (ORF) continuous with that of both E4 and E5 (FIG. 2A). The ORF in E5 was found to encode a polypeptide with a potential for cleavage (FIG. 2B) and subsequent linkage of a phosphoinositide moiety (for cleavage sites and phosphoinositide linkages see Low, 1987), yet shares no homology with the Torpedo 3H alternative exon located at a similar position (Gibney and Taylor, 1990). The nucleotide sequence in the short ORF region from E5 was identical to that in a previous report (Li et al., 1991) except for a single nucleotide difference at position 159 (from G to C) implying a single amino acid substitution (Pro instead of Arg) in the 18th amino acid residue of the E5 peptide. This difference reflects natural polymorphism (Bartels et al., 1993). The remaining 530 bp of E5, were fully sequenced and found non-translatable (FIG. 2B). When the I4+E5 domain was introduced into the HAChE plasmid (Ben Aziz-Aloya et al., 1993) instead of the E6 region, catalytically active enzyme was produced in microinjected *Xenopus* oocytes (data not shown), demonstrating that the product of these alternative transcripts is fully functional.

(d) RNA blot hybridizations. Poly(A)+mRNA from the above noted tissue and cell sources was prepared using poly (dT) Dynabeads (BRL, Gaithersburg, Md.) according to the producer's instructions. Electrophoresis (10 $\mu$g/lane), blotting and hybridization with [32P]-labelled AChEcDNA or PCR-amplified probes was as described (Gnatt et al., 1990). Exposure of labeled blots to X-ray film was for 5–10 days with CAWO intensifying screens. The results of the RNA blot hybridizations are shown in FIG. 3(A, B). The quantification of AChEmRNA levels and the results thereof are set forth in (e) below.

Figure 3B:
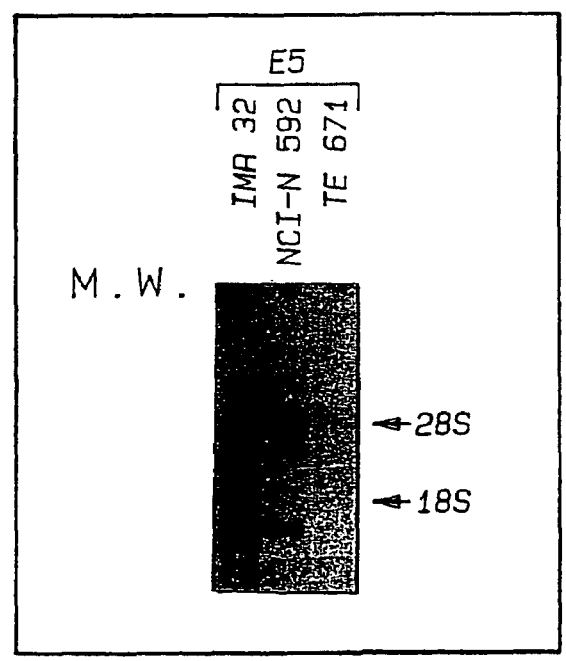

In FIG. 3A there is depicted the tumor AChEmRNA detected with the AChEcDNA probe. In this figure are shown the Poly(A)+mRNA samples (5–10 $\mu$g/lane) that were prepared from cultured IMR32, NCI-N-592 or TE671 cells. Hybridization was with a [32P]-labeled brain AChEcDNA probe (Soreq et al., 1990), produced by enzymatic digestion from plasmid DNA, electroeluted from gel and column purified. Washing was for 1 hr in 0.30M NaCl, 0.022M sodium citrate, 0.5% sodium dodecyl sulfate (NaDodSO4) at 65° C. Electrophoretic migration of 28S and 18S ribosomal RNA and known size markers (Boehringer, Mannheim) is shown on the left hand side of the figure. In FIG. 3B there is depicted the selective detection of tumor AChEmRNA transcripts which include the E5 domain (exon). In this figure are shown the same poly (A)+mRNA samples subjected to the same blot hybridization as in FIG. 3A, but the probe used was a PCR-amplified E5-specific probe prepared with the above noted primers Nos. 5 and 10 using the genomic clone GNAChE as a template. The probe was gel-eluted and random-prime labeled as detailed previously (see Soreq et al., 1990).

Thus, as shown in FIGS. 3(A, B), tumorigenic expression and 3' splice options in the coding domain were first examined by RNA blot hybridization, in search for full-length AChEmRNA transcripts. Hybridization with the brain AChEcDNA probe revealed a single 2.5 kb band for poly (A)+AChEmRNA from TE671 medulloblastoma (FIG. 3A)

and fetal and adult brain (not shown). A faint 28S band, apparently non-specific labeling of ribosomal RNA, was found in both TE671 and NCI-N-592 cells. There was no labeling in IMR32 RNA, indicating low levels of intact AChEmRNA transcripts (FIG. 3A). Signals obtained with 10 μg poly(A)+RNA from all of these sources were lower than those observed for 1 ng of in vitro transcribed AChEmRNA (not shown), demonstrating that AChEmRNA constitutes less that 1:106 of total RNA and in agreement with library screening studies (Soreq et al., 1990).

RNA blot hybridization was further performed with a selective probe from the E5 genomic domain (FIG. 3B). This probe did not label brain AChEmRNA, demonstrating specificity (not shown). In the NCI-N-592 carcinoma cells, it labeled a band of 3.4–3.5 kb as well as the 5.1 kb 28S ribosomal RNA (FIG. 3B). A non-specific band of ca. 1.5 kb, far shorter than the coding sequence of AChEmRNA, was also labeled in both NCI-N-592 and IMR32 cells. No labeling in the TE671 lane suggested low level of the intact E5-containing transcript or its total absence (FIG. 3B). Thus, the RNA blot hybridization data indicated the variably efficient tumorigenic expression of at least two alternative AChEmRNA species, the previously characterized brain and muscle transcript and a larger one, which includes the E5 domain.

To further analyze expression levels and exon-intron boundaries in the alternative tumor AChEmRNA transcripts, the highly sensitive method of PCR amplification was employed. To this end, PCR primers from the E3, I4, E5 and E6 domains were used with reverse-transcribed cDNA preparations from various cells and tissues (see FIGS. 4(A–E)).

In FIGS. 4(A–E) there is shown the exon-intron organization and alternative options for tumorigenic expression in the human AChE gene. In FIG. 4A there is depicted the splicing patterns: Splicing in the AChE gene (shown schematically) is displayed by dashed triangles. Splicing of introns I1, I2 and I3 generates, in all tissues examined, the core domain of the coding sequence from exons E2–4. Alternative splicing occurs in the I4, E5 region and includes 3 options: E4–E6, E4–E5, E6 and E4, I4, E5, E6.

Figure 4A:
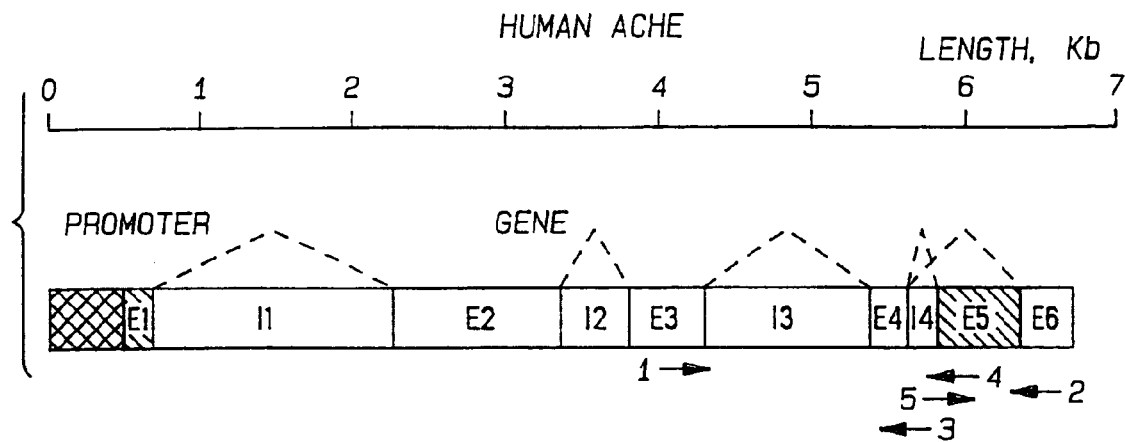
FIGS. 4(A–E) shows schematic depictions of the human AChE gene, the PCR primers used for sequencing and analysis, the PCR products and the differently spliced mRNA products, as described in Example 1.
Figure 4B:
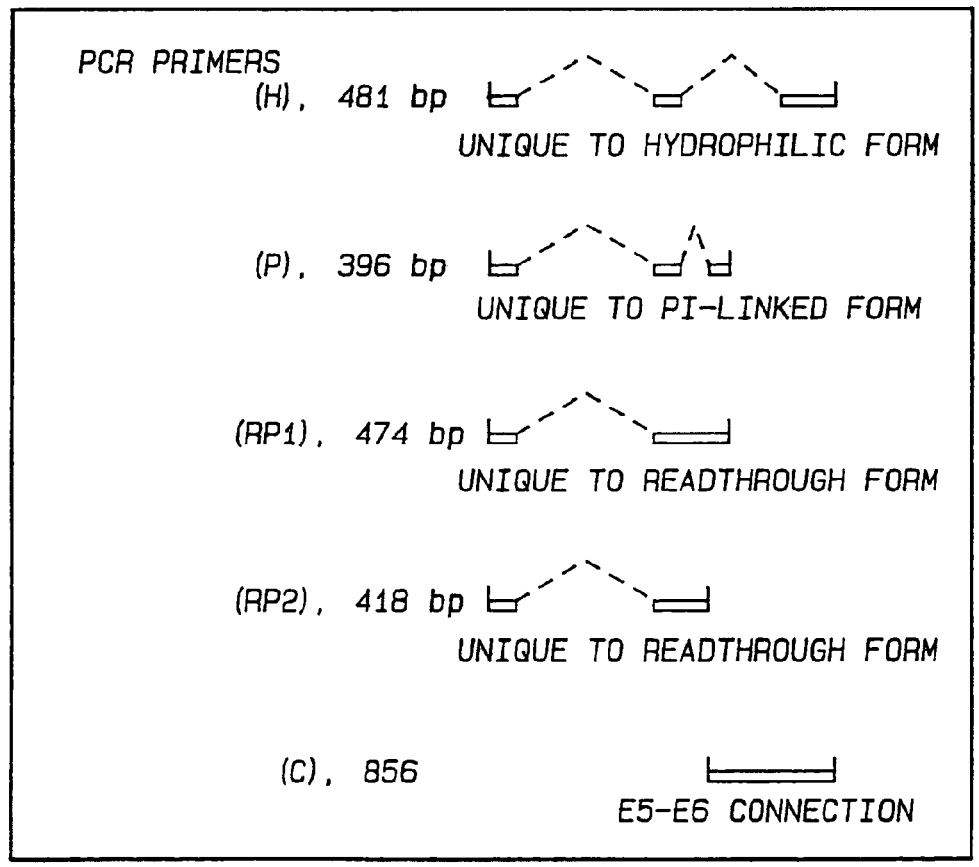

In FIG. 4B there is depicted the PCR primer pairs and the selective RNA-PCR products: PCR primers are numbered as set forth herein above. The primer pair 1,2 could potentially create several alternative products, but practically it only amplified AChEmRNA sequences including the E3, E4 and E6 regions, characteristic of the hydrophilic (H) form (Soreq et al., 1990), with the potential for tailing (Massoulie et al., 1992). This was probably due to unfavorable competition with the relatively more abundant major AChEmRNA species. The primer pair 1,4 detected expression of the putative mRNA subtypes including the E5 exon which encodes PI-linked AChE (P) or the I4/E5 "readthrough" form of AChEmRNA (Li et al., 1991) encoding a longer PI-linked AChE (RPI). The primer pair 1,3 was unique to the readthrough (RP2) form, and the primer pair 2,5 amplified all AChE cDNAs where the E5 exon in the AChE gene is continued by E6 (C).

Figure 4C:
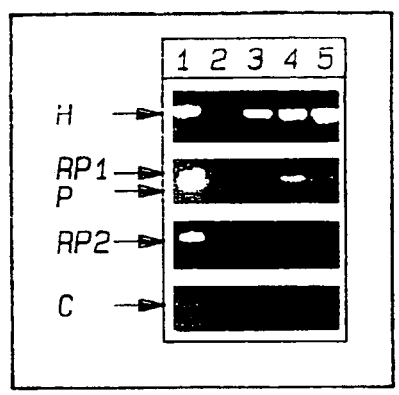

In FIG. 4C, there is shown the results of the RNA-PCR analysis of tumor cell lines: Cell lines were Nt2/D1 teratocarcinoma (lane 1), H9 T lymphoma (lane 2), 293 embryonal kidney cells (lane 3), NCI-N-592 small cell lung carcinoma (lane 4) and Te 671 medulloblastoma (lane 5). RNA-PCR experiments were performed with 100 ng samples of total RNA and the noted primer pairs. Arrows indicate PCR products reflecting the various AChEmRNA transcripts designated as in FIG. 4B.

Figure 4D:
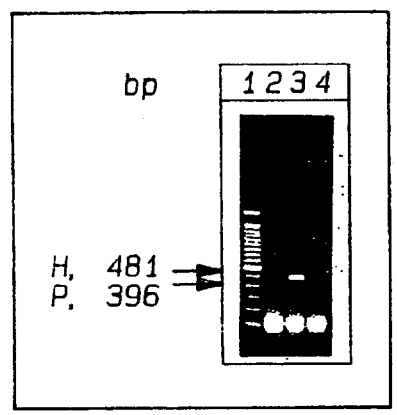

In FIG. 4D there is shown the results depicting the co-expression of common and alternative AChEmRNAs in K562 erythroleukemia cells: Total RNA from K562 cells was subjected to RNA-PCR amplification using the primer pairs 1,4 (lane 2,4) or 1,2 (lane 3). Lane 4 reaction was performed without reverse transcriptase, to exclude presence of genomic DNA contaminations. Molecular weight markers (Boehringer, Mannheim) were electrophoresed in parallel (lane 1). Arrows indicate PCR products and their sizes.

Figure 4E:
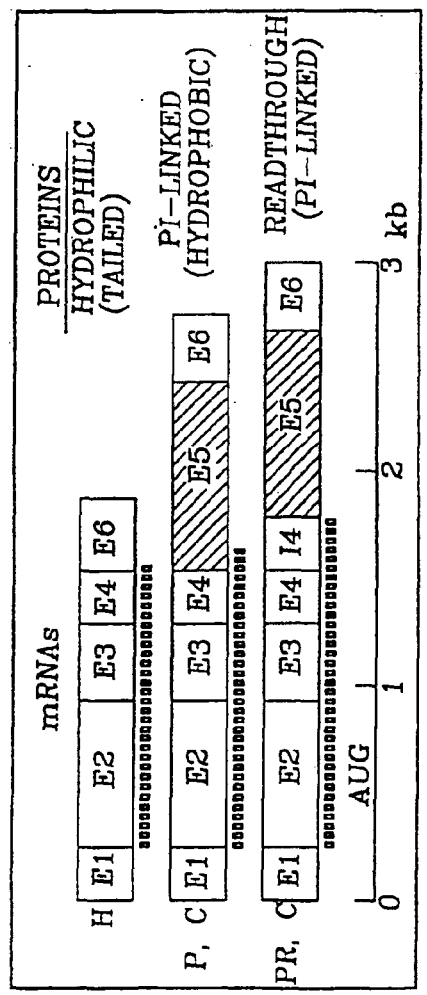

In FIG. 4E there is shown the predicted AChEmRNAs and the proteins translated therefrom: The 3 alternative AChEmRNA transcripts and their putative protein products are schematically displayed. Open reading frames initiated by the AUG codon are marked by a dotted underline, all according to the bottom scale in Kilobase. The resultant protein products would either be hydrophilic (H) and capable of being tailed by non-catalytic subunits, or hydrophobic and amenable to linkage by phosphoinositide moieties (P or PR). In both latter cases, direct connection between E5 and E6 is predicted (C).

Thus, the above noted experiments reconfirmed the presence of a single AChEmRNA species from which the I4, E5 domain was spliced out in brain and muscle, yet revealed two additional splicing patterns in AChEmRNA from tumor cells. PCR primers designed to detect E5 demonstrated the presence of an AChEmRNA species including this exon in NT2/D1 teratocarcinoma, 293 transformed embryonal kidney cells, NCI-N-592 small cell lung carcinoma, TE671 medulloblastoma, DAMI promegakaryoblastic cells and K562 erythroleukemic cells. In all cell types except small cell lung and teratocarcinoma, the PCR band reflecting the alternatively spliced AChEmRNA was considerably less intense than that representing the brain species, which may reflect low abundance of this mRNA in the tumor cells. Interestingly, it was further observed that the unspliced I4-E5 "readthrough" transcript reported in murine bone marrow cells (Li et al., 1991) was also present in all cell lines expressing the E5 alternative exon. PCR reactions detecting the E5–E6 connection were positive in all cell lines expressing E5 and were relatively intense in teratocarcinoma. Thus, three AChEmRNA species were predicted (FIG. 4E).

Since splicing requires precise matching of the terminal nucleotides within each domain, folding energy values were examined (The FOLD Program, University of Wisconsin). These should display considerable differences if they determine specific splicing events. However, the observed values of Gibbs free energy for the E3 and E5 exons were indistinguishable (185 and 180 Kcal/mol, respectively), predicting no preference for E5 splicing over other patterns. The above mentioned results and observations as well as the results and observations mentioned herein below in (e) and (f) are summarized in Table I.

(e) Quantification of AChEmRNA levels. RNA-PCR amplification was performed in 100 μl reactions as detailed above, except that 10 μl aliquots were sampled out every 3rd cycle from cycle 21 on. Following agarose gel electrophoresis and photography, the intensity of fluorescence in the DNA bands at each time point was densitometrically determined (Lapidot-Lifson et al., 1989) and percent of maximum intensity was calculated in each kinetic follow-up. HdAChEmRNA (105–107 copies), in vitro transcribed as described (Soreq et al., 1990) and purified by double DNaseI digestion, was subjected to similar procedure and served for calibration.

Figure 5A:
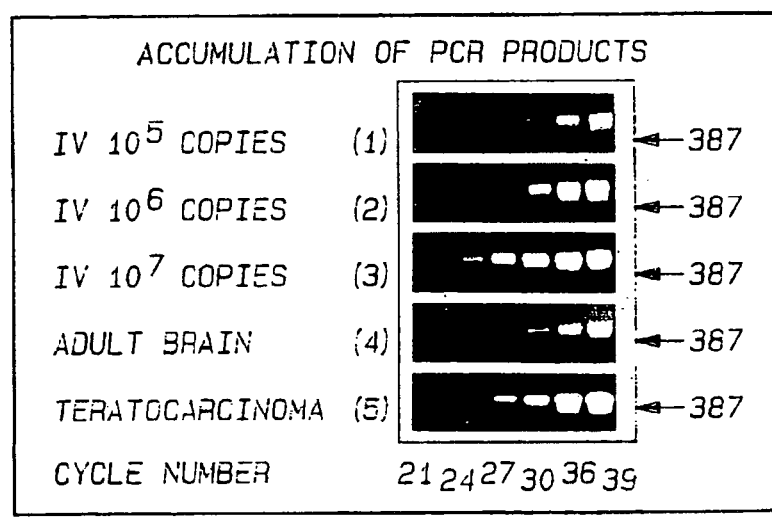
FIGS. 5(A, B) shows schematically the results of the quantification of AChEmRNA levels in teratocarcinoma cells and adult brain; RNA-PCR products (A), and photo-densitometric measurement (B), as described in Example 1.
Figure 5B:
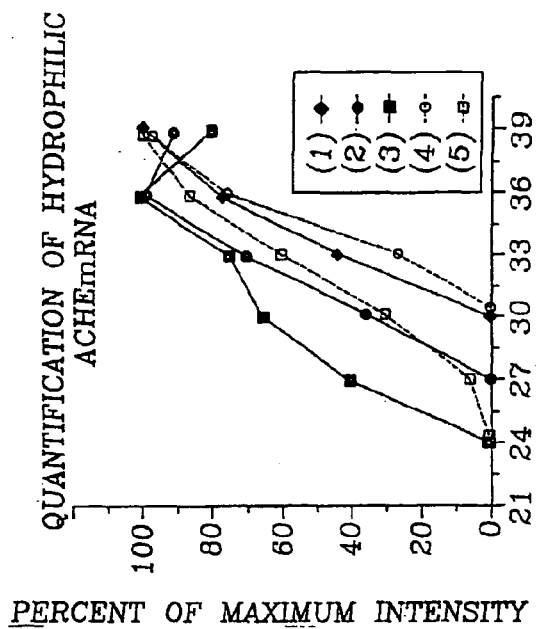

More particularly, to evaluate the level of AChEmRNA within the analyzed cells, RNA extracted from these cell types was subjected to reverse transcription coupled with kinetic follow-up of PCR amplification (RNA-PCR). For this purpose, applicants used PCR primers Nos. 1 and 2 (SEQ ID Nos:13–14), which detected only the AChEmRNA species containing E3, E4, E6 and gave rise to a 481 bp PCR fragment. For calibration, applicants used measured amounts of HdAChERNA in vitro transcribed from the HdAChE deletion construct of human AChEcDNA. In FIG. 5(A, B) there is shown the results of the quantification of AChEmRNA levels in teratocarcinoma cells and adult brain. In FIG. 5A there is shown the RNA-PCR products: RNA samples (100 ng) extracted from adult human cortex or NT2/D1 teratocarcinoma cells were subjected to reverse transcriptase and PCR amplification as noted above. In vitro transcribed (IV) shorter PCR product, was derived using the same primers from measured amounts of the deleted HdAChEmRNA. Length of PCR products in base pairs (bp) is noted. In FIG. 5B there is shown the photodensitometric measurement: Staining intensity for individual PCR products was quantified as noted above. Maximal intensity within each experiment was taken as 100%. Relative intensity of the PCR products was plotted as a function of the number of PCR cycles at which samples were withdrawn.

Thus, the above results indicate that the deleted AChERNA molecules, when subjected to RNA-PCR amplification using the same set of AChE primers, produced a 387 base pairs (bp) PCR fragment, easily distinguishable from the natural one (FIG. 5A). Densitometric analysis of the electrophoretically separated fragments, stained with ethidium bromide, revealed that the timing of appearance of fluorescent PCR products depended on the number of AChEmRNA copies employed. This was also the case when similar amounts of the native and the deleted fragments were amplified together. AChEmRNA products from 100 ng samples of teratocarcinoma RNA were reproducibly detected earlier than those from similar amounts of adult brain RNA (FIGS. 5A, B), demonstrating concentrations 10-fold higher than those in brain (107 as compared with 106 molecules/μg RNA, respectively). Based on average yields of 1 μg RNA/mg wet weight tissue, and assuming ca. 1×106 cells/mg tissue, this implies 10 and 1 AChEmRNA molecules/cell, on the average, or 20 and 2 pM concentration of this mRNA in teratocarcinoma cells and adult brain, respectively.

(f) AChE gene expression in various tumor cell lines. As mentioned above, RNA-PCR was employed to quantify AChEmRNAs in tumor cell lines of different tissue origins, primary tumor biopsies and normal tissues (Table I). The major brain species of AChEmRNA was detected in all of the cell lines examined, with the exception of the H9 T-cell lymphoma and the lymphocytic HL-60 cells (not shown) and in line with a previous report of BCHE but not AChE expression in a lymphocyte cell line (Rubinstein et al., 1984). Six out of the 9 tumor cell lines examined further expressed the alternative E5 exon with different efficiencies. The product representing the readthrough (I4-E5) species was particularly bright in at least one of these cell types and was clearly observed in 4 more lines. All of the AChEmRNA preparations containing E5 also exhibited a direct connection to E6 (Table I and unshown data) However, applicants cannot exclude the possibility that part of the AChEmRNA transcripts in these preparations lacked the E6 domain.

In contrast with the expression of E5-containing transcripts in tumor cell lines, applicants could not detect any AChEmRNA other than the major brain transcript in primary tumor biopsies, including 3 types of malignant ovarian adenocarcinomas and benign myoma (Table I), nor did applicants find it in 5 different samples from malignant brain tumors. In RNA preparations from fetal and adult brain and from adipose tissue, applicants could only detect the major AChEmRNA species. RNA-PCR amplification of mRNAs encoding the AChE-homologous enzyme BChE (Prody et al., 1987) and the cell division controller CHED (Lapidot-Lifson et al., 1992) served to verify the integrity of the examined RNA preparations (see Table I).

(g) Variable translation Products. As mentioned herein above, open reading frames in the I4 and E5 domains imply potential changes in the AChE protein products of the alternative transcripts. Because of the non-translated part of E5, the open reading frame in E6 will not be translated in E5-containing transcripts. Therefore, applicant's data predict that in several tumor cells three different C-terminal peptides may stem from the E6, E5 or I4/E5 domains in the AChE gene. The inferred AChE forms divert from each other at the amino acid (a.a.) position 544 (Soreq et al., 1990; Ben Aziz-Aloya et al., 1993), and the peptide translated from the I4/E5 region and presented in FIG. 2B is absent in the 583 a.a. long hydrophilic "tailed" brain AChE form, encoded by exons 2, 3, 4 and 6. The predicted phosphoinositide-linked AChEs produced from the E5-containing transcripts should be 583 and 557 a.a. long, with their 40 and 14 C-terminal amino acids translated from the open reading frames in the alternative I4+E5 or E5 domains, respectively. Yet 29 more residues, also translated from the E5 exon, constitute a hydrophobic cleavable peptide common to both AChE forms produced from E5 containing transcripts. When subsequent to the HG dipeptide, such hydrophobic domains are characteristic of precursors to PI-linked proteins (see Massoulie et al., 1992). Applicants Xenopus microinjection experiments revealed that at least 2 of these 3 AChE protein forms should be produced in various tumor cells.

Figure 6:
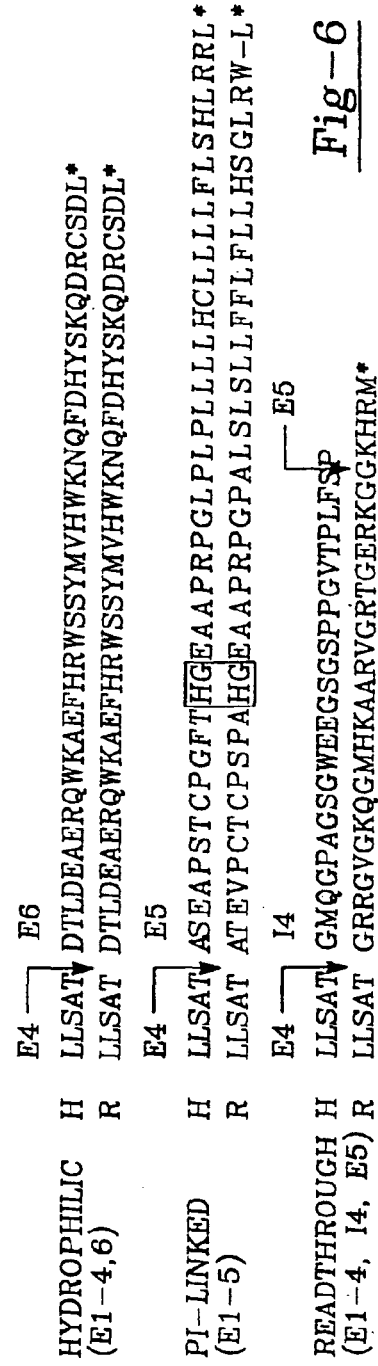
FIG. 6 shows schematically the alignment of the variable translation products (SEQ ID NOS:7–12) inferred from the alternative ACHEDNA sequences in human and rat, as described in Example 1.

In FIG. 6 there is shown, schematically, the alignment of the variable translation products inferred from the alternative AChEDNA sequences in human and rat. Amino acid sequences were deduced from the DNA sequence data as noted above, for the alternative human AChE forms and as published (Legay et al., 1993a,b) for the counterpart rat AChE forms. In FIG. 6 the exon borders are delineated. The HG residues required for PI linkage are boxed. The Proline residue which represents a natural polymorphism in the human sequence (Bartels et al., 1993) is dotted. Note the conspicuous homologies between the E6 and E5 C-terminal peptides (SEQ ID NOS:7–8) in human and rat and the absence of such homology for the I4-inferred readthrough peptide (SEQ ID NOS:9–10). Nonsense, termination codons are noted by stars. Interestingly, the C-terminal peptides of the hydrophilic AChE form are virtually identical in rat and human (SEQ ID NOS:5–6), with the exception of a minor alteration of one amino acid residue (replacement of aspartate 57B in the human enzyme by glutamate in rat). The human E5-inferred translation product presents a more limited 53% identity with the rat one, whereas the homology within the I4-inferred products was found to be negligible (8%, FIG. 6).

In view of the results and observations set forth herein above in Example 1, it may thus be concluded that the present findings reflect a surprising complexity of alternative splicing patterns of AChEmRNA transcripts in tumor cell lines from heterogeneous tissue origins. Furthermore, these variable AChEmRNA species may encode 3 different AChE polypeptides, with potentially distinct properties, one of which is unique to humans.

The dominant species of AChEmRNA expressed in tumor cells includes exons E2, E3, E4 and E6. It encodes the globular hydrophilic AChE form (Soreq et al., 1990), which may remain soluble (see Massoulie et al., 1992), interact with the collagen-like subunit characteristic of asymmetric AChE at the neuromuscular junction (Krejci et al., 1991) or associate with a lipid-containing structural subunit in brain (Inestrosa et al., 1987). The fourth intron, which follows the fourth exon, is variable in size within tumor cell lines. According to the dominant splicing pattern, this intron is 829 bp long, and its splicing connects the E4 and the E6 exons. Alternatively, the 3'-terminal. 751 residues from this intron, or the entire 829 residues, are expressed and may directly be continued by the E6 exon. This leads to the production of the E5 or the I4/E5-containing AChEmRNAs. RNA-PCR amplification was, not surprisingly, more sensitive than blot hybridization for detecting the alternative mRNA transcripts.

The above findings predict the production of two forms of membrane-associated AChE from the alternative AChEmRNAs in different human tumor cells, in addition to the hydrophilic form. Interestingly, the two hydrophobic peptides translated from these alternative AChEmRNAs contain a free cysteine residue at the C-terminus, which implies that they both may be disulfide-linked to a second AChE monomer, to create the dimers characteristic of vertebrate erythrocytes (Toutant et al., 1990). That the alternative transcripts found in tumor cells are the molecular origin(s) for PI-linked AChE is indicated from reports that K-562 cells are similar to various vertebrate erythrocytes (Roberts et al., 1991) in their production of PI-linked AChE. It should be noted that in both the mouse and rat AChE genes, the I4 domain includes a termination codon (Li et al., 1991; Legay et al., 1993b). The inferred "readthrough" enzyme in human may hence be distinguished from the rodent ones both in its length (583 residues) and in its capacity for PI-linkage. Yet, expression of AChEmRNA does not necessarily imply production of its protein, as is indicated from the absence of AChE activity in 293 cells (Velan et al., 1991).

Different choices of splicing options for AChEmRNA may be physiologically important: Thus, C-terminally mutated variants of the closely related human enzyme BChE display distinct differences in their inhibitor interactions as compared with the normal enzyme (Neville et al., 1992). This, in turn, suggests that altered C-terminus may modify the biochemical properties of cholinesterases. AChE forms with apparently modified biochemical properties were, indeed, found associated with various tumor types (Zakut et al., 1991; reviewed in Soreq et al., 1991) and in the demented brain of Alzheimer's disease patients (Navaratam et al., 1991). It is therefore possible that alternative splicing could contribute to these modifications and to the distinct properties of embryonic AChE (see review, Soreq and Zakut, 1993).

Further, cholinesterase gene amplifications (see Soreq and Zakut, 1993) have been correlated with a variety of tumors including those of the nervous, reproductive and hemopoietic systems. However, the tumor amplified AChE gene tended to be incomplete (see Zakut et al., 1992) and therefore unlikely to drive effective transcription. Hence, it is not surprising that AChEmRNA levels in the tumor cells were higher, yet within the same range as in normal developing tissues. The presence of an E-box motif in the recently cloned AChE promoter (Ben Aziz-Aloya et al., 1993) suggests an alternative route for a more limited tumorigenic induction of AChE, by the enhancement of transcription through c-Myc (Blackwell et al., 1991). Intensive transcription may thus explain the presently described alternative splicing patterns. This can occur by default, perhaps due to the tumorigenic lack of sufficient amounts of the specific protein factor(s) controlling the common splicing pattern of AChEmRNA in brain. That transcription is particularly intensive in the tumor cell lines is evident from the high levels of AChE, BChE and CHED transcripts in them.

Interestingly, the above findings demonstrate three alternative pathways for AChE transcripts in tumor cell lines, yet not in primary tumor tissues. This may reflect mechanism(s) related with the mode of cell growth and which distinguish cultured cells from the in vivo situation. It should be noted in this respect that the AChE promoter includes an Egr-1 motif, predicting serum induction (Ben Aziz-Aloya et al., 1993). Absence of angiogenic limitations under culture conditions can therefore upregulate AChEmRNA transcription. Also, the predicted PI-linked AChE forms may induce tumorigenic processes. The growth-regulatory role reported for AChE in murine erythroleukemic Friend cells (Paoletti et al., 1992) and observed recently by in vivo antisense inhibition of AChE gene expression (Lev-Lehman et al., 1993) is in line with this latter prediction. The pattern of AChE biosynthesis at multiple stages of the biosynthetic pathway presents an intricate model for the complex modulation of tumor-specific gene expression.

Example 2

Figure 7A:
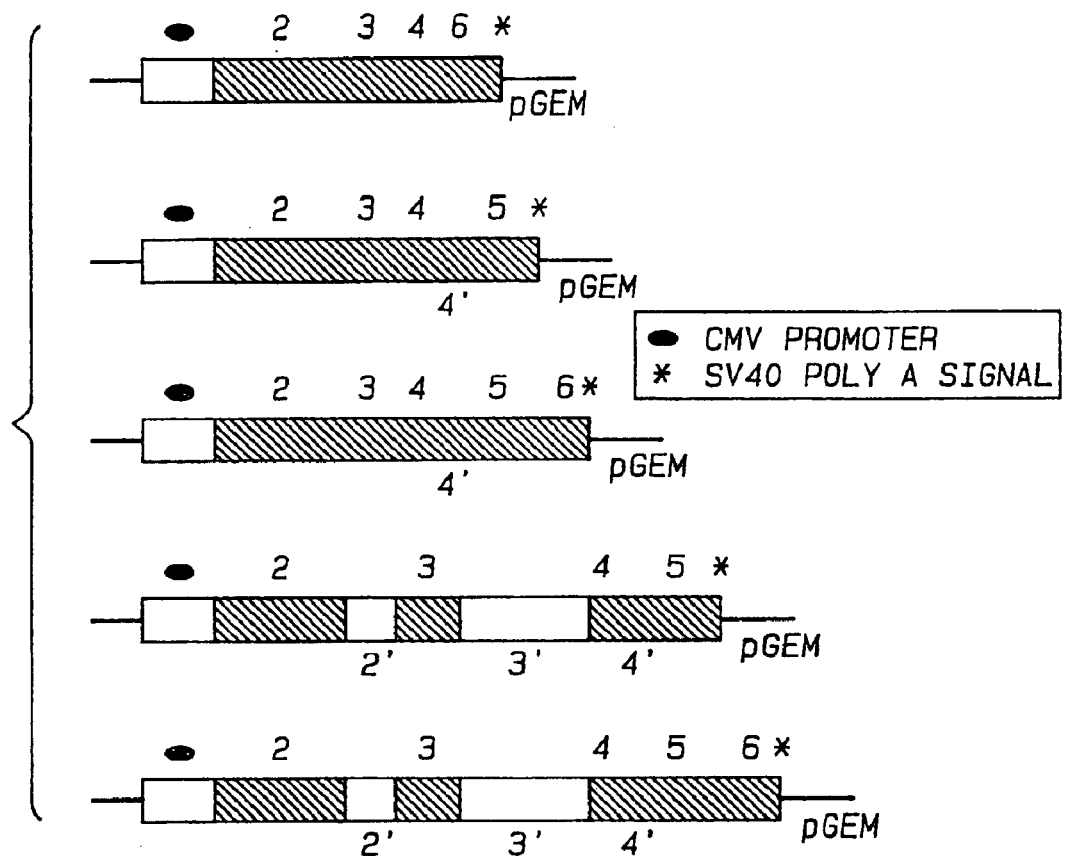
FIGS. 7(A–B) shows schematically the various constructs: CMVACHE, E2–E5, E2–E5 trimmed plasmid, E2–E6, and E2–E6 trimmed plasmid, as described in Example 2.
Figure 7B:
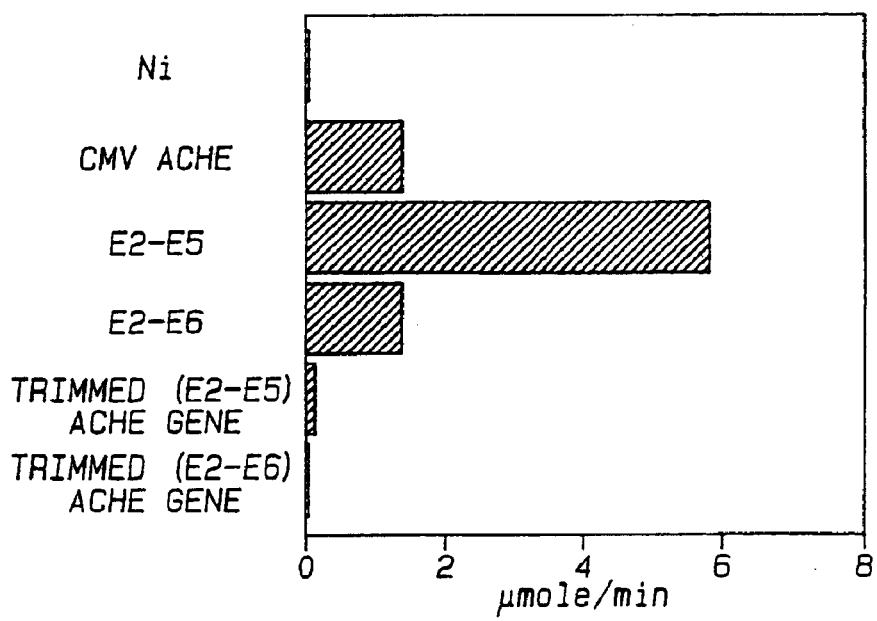

Expression of Human Acetylcholinesterase (HAChE) in *Xenopus laevis* embryos (a) Expression vectors. A number of vectors were constructed, by standard genetic engineering procedures, and contain different regions of the human ACHE gene (see Example 1). The construct that was analyzed most thoroughly was the one encoding the brain and muscle form of AChE, namely, the one encoding exons 2, 3, 4 and 6 (SEQ ID NO:1) of the AChE gene, this construct (also called CMVAChE or CMVACHE) being described previously in Velan et al., 1991. All of the constructs are pGEM derivatives and have the AChE coding regions under the control of the cytomegalovirus (CMV) immediate-early gene enhancer promoter sequence and an SV40 polyadenylation site. In FIG. 7 there is shown schematically the various constructs:

(i) CMVACHE, a construct containing the cDNA encoding human brain AChE (exons 2, 3, 4 and 6), the CMV promoter and SV40 polyadenylation site, which was constructed using the pGEM expression vector (see Velan et al., 1991). This vector was used to construct the other constructs ((ii)–(v), herein below).

(ii) E2–E5, a vector constructed by insertion of the genomic DNA fragment, isolated from the genomic ACHE clone (GNACHE, Soreq et al., 1990), into the Not I (E4) and HpaI (ACHECMV cloning site) sites of the CMVACHE vector. This vector contains the exons 2, 3 and 4 (E2, E3, E4) as well as the intron 4 (I4) and exon 5 (E5). The 5' end of exon 4 has the NotI site used for cloning and the E5 region extends to the HindII site which is downstream from the E5 stop codon (see sequence in Example 1 above) (Karpell et al. 1993).

(iii) E2–E5 trimmed plasmid, a construct made by insertion of a genomic DNA fragment (from GNACHE, as noted above) containing, in 5'-3' order, 5' E2 (with an SphI site), I2, E3, I3, E4, I4 and E5 (extending to the HindII site at the 3' end), into the SphI (E2) and HpaI (cloning site on vector) sites of CMVACHE.

(iv) E2–E6, a plasmid constructed by insertion of the 3' end of the ACHE gene containing E4 (with NotI site), I4, E5 and E6 (with a SalI site) into the NotI (E4) and SalI (cloning site on vector, one of the multiple cloning sites) sites of the CMVACHE. This vector also contains, at the 5' end, the E2 and E3 regions.

(v) E2–E6 trimmed plasmid, a construct made by insertion of a fragment containing E2 (with a SphI site), I2, E3, I3, E4, I4, E5 and E6 (with SalI site) into the SphI and SalI sites of the CMVACHE vector.

The above E2–E5 construct (ii) can potentially encode the two alternative PI-linked forms (Example 1). The E2–E6 construct (iv) contains both the common and the alternative regions and can potentially encode all 3 forms of AChE (brain form and two PI-linked forms). The two trimmed constructs (iii) and (v) differ from their counterparts (E2–E5 and E2–E6) by containing, in addition, the I2 and I3 introns.

It should be noted that other constructs have been made, for example, as described in Ben Aziz-Aloya et al., 1993, in which the ACHE promoter was used (instead of the CMV promoter), but these have lower levels of AChE expression.

Each of the above constructs was microinjected into and expressed in *Xenopus* oocytes. Subsequently, the acetylthiocholine (ATCh) hydrolyzing activity of each of the different expressed human AChE forms was determined, the results of which are presented, graphically, in FIG. 7B. The ATCh hydrolyzing activity is presented in $\mu$mole ATCh hydrolyzed per minute for 1/3 oocyte/sample. Other assays of the human AChE expressed in *Xenopus* are described herein below in more detail, including a similar ATCh hydrolyzing assay. From the results shown in FIG. 7B it is apparent that the most active form was the one encoded by the E2–E5 construct. The other forms encoded by constructs that do not contain the I2 and I3 introns, namely, the CMVACHE and E2–E6 encoded forms, also showed significant ATCh hydrolyzing activity (see also results described below with reference to FIGS. 8(A–D)). However, the two forms encoded by the trimmed E2–E5 and E2–E6 vectors showed little or no activity.

(b) Biochemical and cytochemical analyses of AChE expressed in *Xenopus* embryos. The following is a brief summary of a number of the analytical procedures which were performed. Where relevant, more specific details are provided in the subsequent sections concerning the experimental results as set forth herein below.

(i) Protein blot analyses. Following the above mentioned (General Procedures) microinjection procedure, recombinant human AChE (rHAChE) was purified from approximately 180 "Day 1" CMVACHE-injected embryos by affinity chromatography using a modified procedure for the purification of native human AChE (Gennari and Brodbeck, 1985). Briefly, AChE from embryos homogenized in LSD buffer was bound to Sepharose beads carrying N-(1-aminohexyl)-3-dimethylethylaminobenzoic amide by shaking overnight at room temperature. Elution was with 0.02M edrophonium chloride (Tensilon, Hoffman-LaRoche, Switzerland). Embryonic *Xenopus* AChE was similarly purified from 1 week old tadpoles, but had to be eluted by boiling in 0.1% SDS. Denaturing SDS polyacrylamide gel electrophoresis and blotting were essentially as described elsewhere (Liao et al., 1992) using a pool of monoclonal antibodies (mabs; 132-1, 2, 3; 6 $\mu$g/ml each) raised against denatured human brain AChE (Brodbeck and Liao, 1992).

(ii) Sucrose gradient analysis of AChE subunit assembly. Freshly prepared, high salt/detergent extracts from 1–2 embryos or 5–10 oocytes were applied to 12 ml 5–20% linear sucrose density gradients and centrifuged overnight at 4° C. Fractions were collected into 96-well microliter plates and assayed for total ACHE activity as previously described (Soreq et al., 1989). To distinguish between rHAChE and endogenous *Xenopus* AChE in gradient fractions, 100 $\mu$l aliquots were transferred to a Maxisorp immunoplate (Nunc, Denmark) coated with a monoclonal antibody (mAb 101-1) recognizing human but not frog AChE, and diluted 1:1 with double distilled water. Following overnight incubation, the plates were washed 3 times with PBS containing 0.05% Tween 20 and each well assayed for catalytically active AChE.

(iii) Cytochemical AChE staining and Electron Microscopy. Embryos were fixed, cytochemically stained for AChE, and prepared for electron microscopy as previously described (Ben Aziz-Aloya et al., 1993). Cytochemical staining (Karnovsky, 1964) was carried out in acetate buffer (pH 6.1) for 15–20 minutes at 4° C. within 3 days of fixation.

Figure 8A:
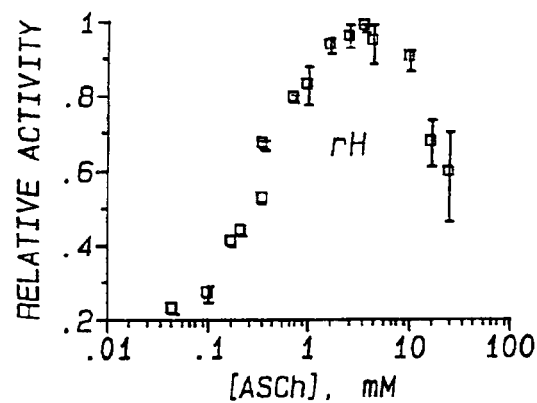
FIGS. 8(A–D) shows graphically the results depicting the expression of catalytically active recombinant human AChE (rHAChE) in Xenopus oocytes, as described in Example 2.
Figure 8B:
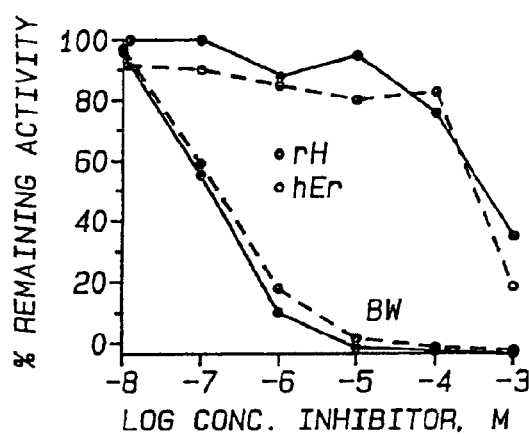
Figure 8C:
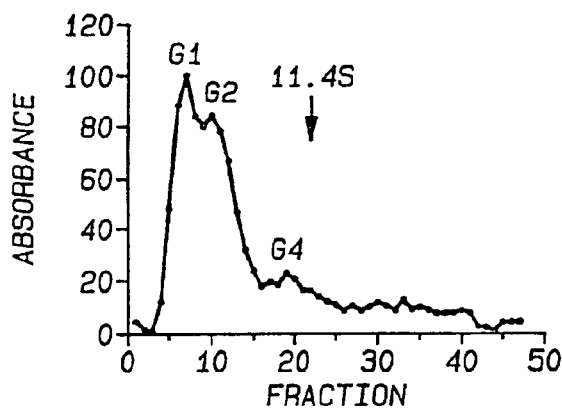
Figure 8D:
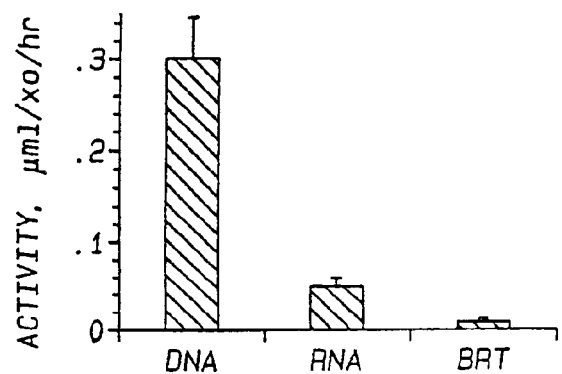

(c) Activity of human AChE expressed in *Xenopus*. In FIGS. 8(A–D) there is shown the results depicting the expression of catalytically active recombinant human AChE (rHAChE) in *Xenopus* oocytes. In FIG. 8A there is shown the results of the inhibition of rHAChE (rH in figure) by excess substrate. In these experiments mature *Xenopus* oocytes were injected with 5 ng of in vitro transcribed AChEmRNA (Soreq et al., 1990) and incubated overnight at 17° C. Homogenates corresponding to 1/3 oocyte were assayed for AChE activity in the presence of various concentrations of acetylthiocholine (ATCh) substrate (average of 3 experiments±SEM). In FIG. 8B there is shown the sensitivity of rHAChE (rH in figure, closed circles) to selective inhibitors. In these experiments oocyte homogenates were preincubated for 30 minutes in assay buffer containing the AChE-specific, reversible inhibitor, 1,5 bis (4-allyldimethyl-ammoniumphenyl)-pentan-3-one dibromide (BW284C 51, BW) or the butyrylcholinesterase-specific inhibitor tetraisopropyl pyrophosphoramide (iso-OMPA, IO) at the indicated concentrations and assayed for remaining activity following addition of 2 mM ATCh (average of duplicate assays from 2 independent microinjection experiments). AChE extracted from human erythrocytes (hEr, open circles) served as control. In FIG. 8C there is shown the oligomeric assembly of the rHAChE. In these experiments, homogenates from AChEmRNA-injected oocytes were subjected to sucrose density centrifugation as described in (b) above (average of 3 experiments). Note that in addition to the free monomer (3, 2 S, G1), the oocyte appears to generate dimers (5.6 S, G2) and to a lesser extent tetrameres (10.2 S, G4) of human AChE. Endogenous oocyte AChE activity is undetectable under these conditions. Arrow marks position of bovine liver catalase (11.4 S), used as a size marker. In FIG. 8D there is shown the expression of AChEDNA in *Xenopus*. In these experiments, oocytes were injected with 5 ng synthetic AChEmRNA or AChEcDNA under control of the cytomegalovirus promoter-enhancer element (CMVAChE; see (a) above and Velan et al., 1991a) and incubated for 1 (RNA) to 3 (DNA) days. Oocytes injected with incubation medium (BRT) or uninjected oocytes served as control. Activity is expressed as $\mu$moles substrate hydrolyzed per hour per oocyte±SEM for 3 independent microinjection experiments.

Thus, from the results presented in FIGS. 8A–D it is apparent that when microinjected into mature *Xenopus laevis* oocytes, 5 ng in vitro transcribed AChEmRNA directed the production of catalytically active AChE displaying substrate and inhibitor interactions characteristic of the native human enzyme (FIGS. 8A, B). The apparent Km calculated for rHAChE towards acetylthiocholine was 0.3 mM, essentially identical to that displayed by rHAChE expressed in cell lines (Velan et al., 1991a) and native human erythrocyte AChE (data not shown). In sucrose density centrifugation rHAChE sedimented primarily as monomers and dimers, although a discernible peak apparently representing globular tetrametric AChE was also observed (FIG. 8C). When plasmid DNA carrying AChEcDNA downstream of the cytomegalovirus promoter-enhancer element (CMVAChE) was microinjected into oocytes, active AChE in yields 10–20 fold higher than that observed following RNA injections was obtained (FIG. 8D), demonstrating efficient transcription from this promoter in Xenopus.

Figure 9:
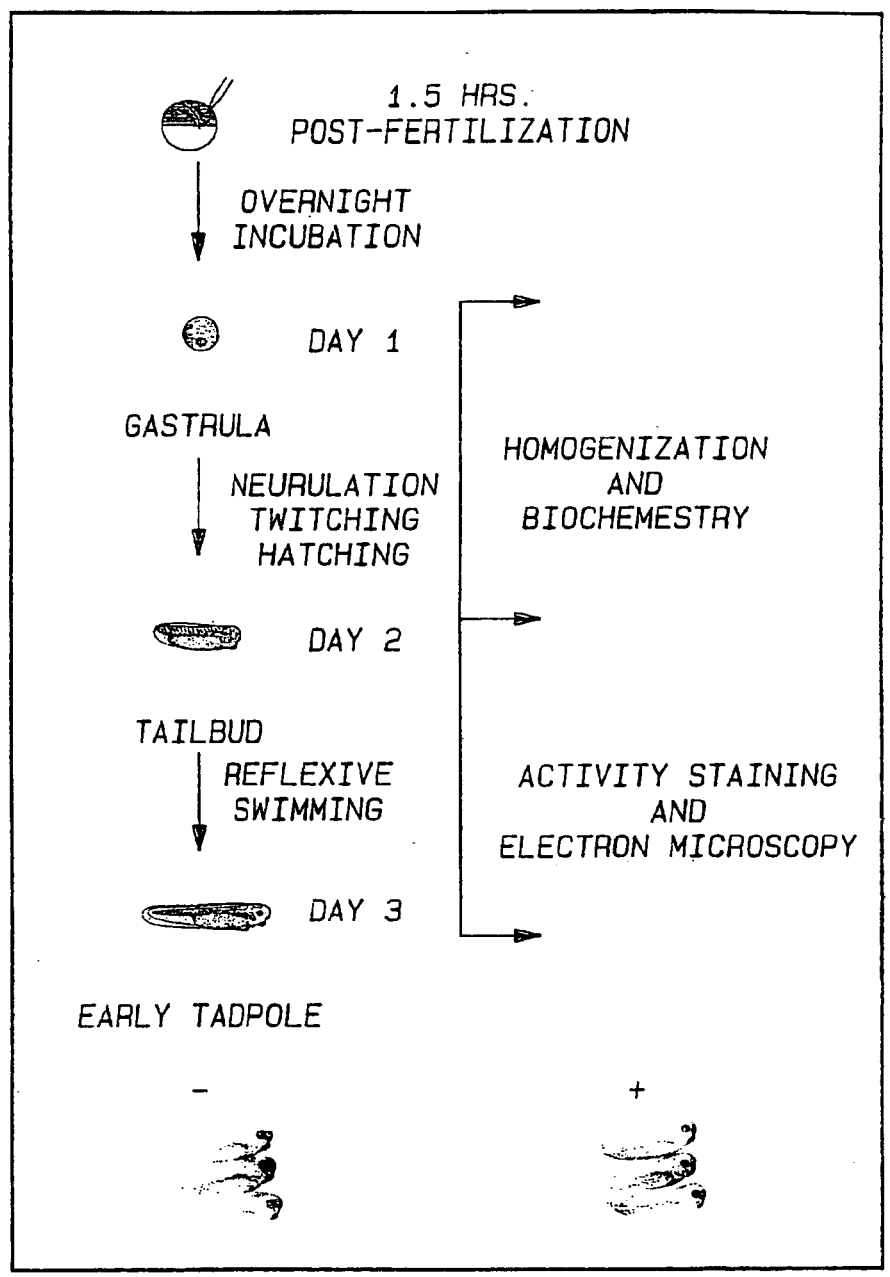
FIG. 9 shows a schematic representation of a microinjection experiment depicting the principal developmental stages and analytical approaches used together with photographs displaying the normal gross development of unstained microinjected embryos (+) compared with control uninjected embryos (−) 3 days post-fertilization, as described in Example 2.
Figure 10B:
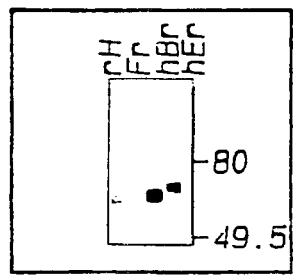
FIGS. 10(A, B) shows schematically (A) the results depicting the expression of human AChE (rHAChE) in CMVACHE-injected Xenopus embryos and electorphoretically (B), which expression results in the maintenance of biochemically distinct heterologous human AChE in the embryos for at least 4 days, as described in Example 2.
Figure 10A:
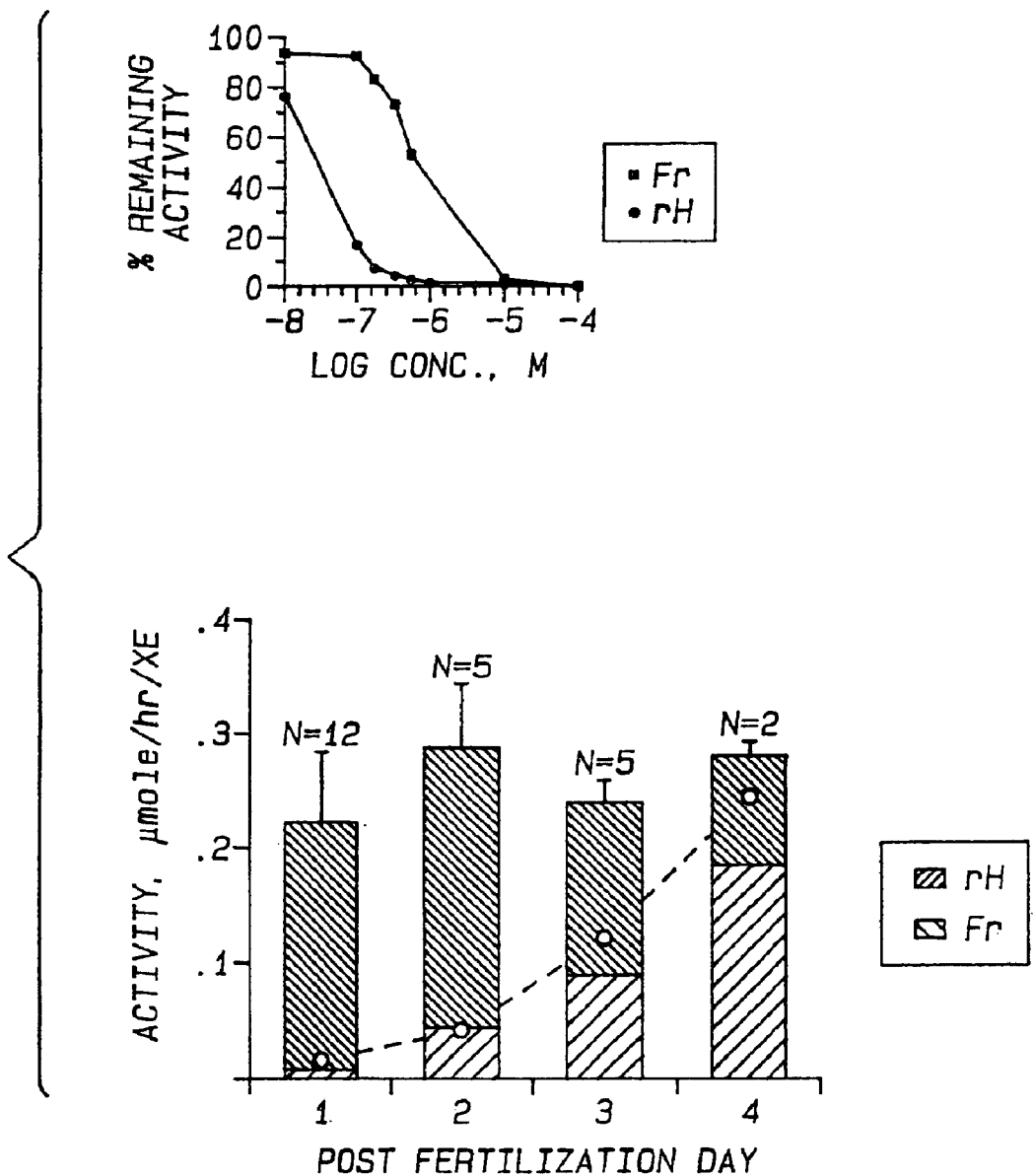
Figure 11A:
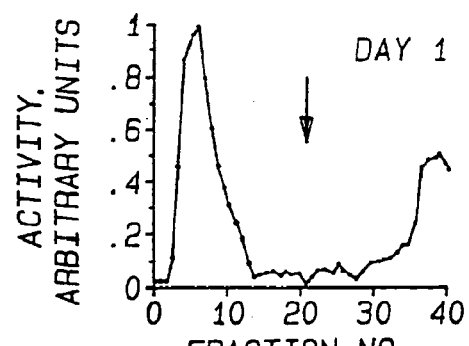
FIG. 11 shows graphically the results depicting the assembly of rHAChE in Xenopus embryos, namely, the rHAChE in microinjected embryos remains monomeric, as described in Example 2.
Figure 11B:
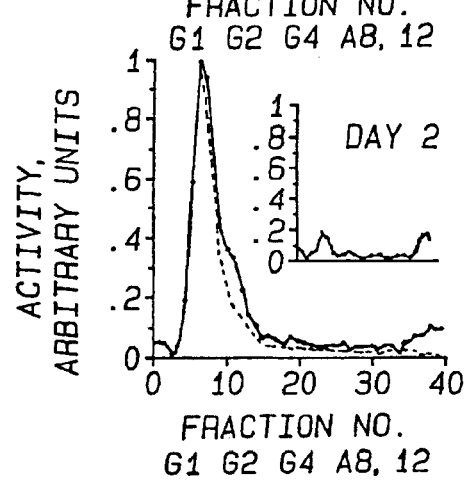
Figure 11C:
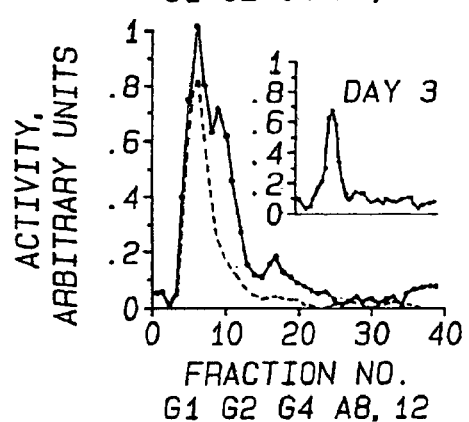
Figure 11D:
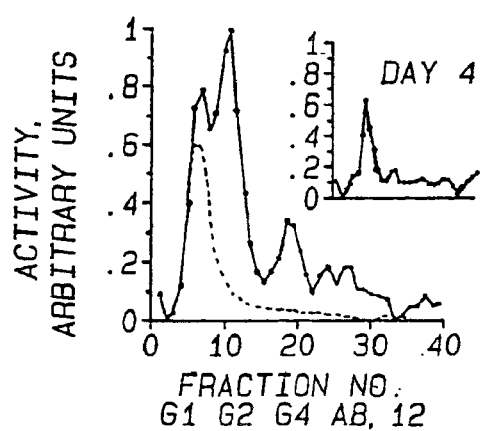
Figure 12A:
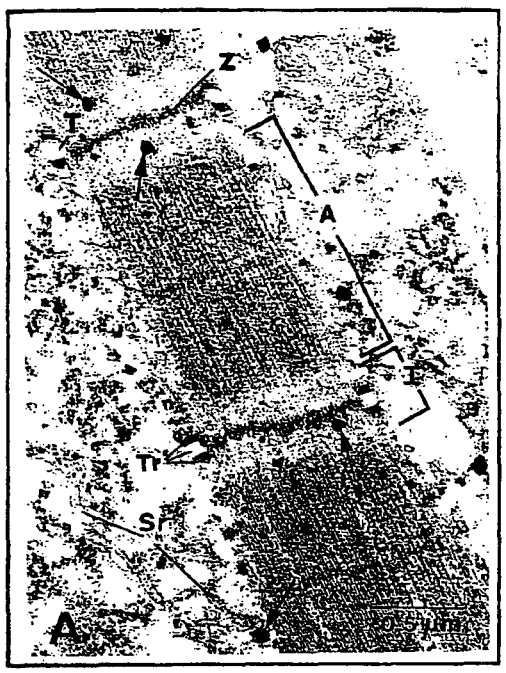
FIGS. 12(A–D) shows the results (electron micrographs) depicting the disposition of rHAChE in myotomes from two day old microinjected Xenopus embryos, as described in Example 2.
Figure 12B:
Figure 12C:
Figure 12D:

(d) The effect of expression of human AChE on the normal development of Xenopus embryos. In FIG. 9 there is shown a schematic representation of a microinjection experiment depicting the principal developmental stages and analytical approaches used together with photographs displaying the normal gross development of unstained microinjected embryos (+) compared with control uninjected embryos (−) 3 days post-fertilization. In vitro fertilized eggs of Xenopus laevis were injected with 1 ng of CMVAChE and cultured for 1–4 days as described herein above. In FIG. 10(A, B) there is shown the results depicting the expression of human AChE (rHAChE) in CMVACHE-injected Xenopus embryos, which expression results in the maintenance of biochemically distinct heterologous human AChE in the embryos for at least 4 days. In FIG. 10A there is shown the overexpression of rHAChE in developing embryos. In these experiments, high salt/detergent extracts of CMVAChE-injected and uninjected embryos were prepared and assayed for AChE activity in the presence and absence of the selective inhibitor ecothiophate (3.3×10−7 M, inset, for description of inset see herein below). Endogenous AChE activity was calculated according to an algorithm assuming 90% inhibition of rHAChE and 20% inhibition of frog AChE at this concentration of inhibitor. Bar graph represents the total AChE activity measured per microinjected embryo at various time points following microinjection and the calculated activities attributable to rHAChE (dark shading) and endogenous frog AChE (light shading). The total AChE activity measured in uninjected control embryos at the same time points is indicated by white circles. Data represents average of 4–6 embryos from the indicated number (N) of independent microinjection experiments±SEM. INSET: Selective inhibition of recombinant human AChE by ecothiophate. Homogenates representing endogenous frog (Fr) or recombinant human (rH) AChE were assayed for activity following 40 minutes preincubation with the indicated concentrations of ecothiophate. Average of 3 experiments. In FIG. 10B there is shown the immunochemical discrimination between rHAChE and embryonic Xenopus AChE. In these experiments affinity purified AChE from CMVAChE-injected Xenopus embryos (rH), control uninjected embryos (Fr), human brain (hBr) and erythrocytes (hEr) was subjected to dehaturing gel electrophoresis and protein blot analysis as described herein above in (b). Each lane represents approximately 20 ng protein, except rH which contained only 6 ng. Note the complete absence of immunore-activity with embryonic Xenopus AChE although silver staining of a parallel gel demonstrated detectable protein at the corresponding position (not shown). The faint upper bands (140–160 Kd) in the lanes displaying native human AChEs represent dimeric forms resulting from incomplete reduction of the intersubunit disulfide bonds (see Liao et al., 1992). Prestained molecular weight markers indicated on the right were from Bio-Rad, USA.

Thus, from FIGS. 9 and 10 it is apparent that when microinjected into cleaving Xenopus embryos, CMVAChE directed the biosynthesis of rHAChE at levels similar to those observed in DNA-injected oocytes. Yet, the gross morphology and development of CMVAChE-injected embryos appeared completely normal (FIG. 9). Moreover, gross motor function of microinjected embryos, as evaluated by twitching and hatching on day 2, reflexive swimming on day 3, and free swimming on later days, was unimpaired compared to normal, uninjected controls. Microinjected tadpoles survived up to four weeks, showing no overt developmental handicaps (not shown). Following overnight incubation, at which time embryos had reached the late gastrula stage, endogenous AChE levels were negligible and rHAChE activity represented a 50 to 100-fold excess over normal (FIG. 10A). From day 2 post-fertilization, detectable endogenous AChE activities increased steadily. Using the irreversible AChE inhibitor ecothiophate (Neville et al., 1992) to distinguish between endogenous frog AChE and rHAChE (FIG. 10A, inset), applicants observed the persistence of receding levels of rHAChE for at least 4 days post-fertilization. For the first 3 days rHAChE accounted for >50% of the total measured AChE activity in microinjected embryos and resulted in a state of general overexpression compared to uninjected controls. By day 6 PF, no heterologous enzyme could be detected in homogenates (not shown). At all time points examined, the level of frog AChE in CMVAChE-injected tadpoles appeared less than that observed in uninjected embryos, suggesting that feedback regulation may be involved in modulating AChE biosynthesis in these transiently transgenic embryos.

In immunoblot analysis following denaturing gel electrophoresis, rHAChE was observed to comigrate with native human brain AChE, yielding a clearly visible doublet band at around 68 Kd (FIG. 10B). rHAChE was selectively recognized by a pool of monoclonal antibodies raised against denatured human brain AChE, and no cross-immunoreactivity with embryonic Xenopus AChE was observed (FIG. 10B). The doublet band observed may reflect differences in glycosylation (Kronman et al., 1992). Sequential extractions with low salt, detergent, and high salt buffers revealed that approximately 35% of rHAChE synthesized in transiently transgenic embryos was associated with membranes, requiring detergent for solubilization (see Table II below). Whereas up to 33% of the endogenous enzyme in day 3 uninjected tadpoles appeared in the high-salt extractable fraction, salt-soluble rHAChE remained primarily in the low-salt fraction at all days examined (Table II). Enzyme-antigen immunoassay (EAIA) utilizing a species-specific monoclonal antibody (mAb 101-1) was employed to differentiate between human and frog enzyme in the fractions.

As mentioned above, fertilized Xenopus eggs were microinjected with 1 ng CMVAChE DNA, cultured for 1–3 days and subjected to homogenization and subcellular fractionation. rHAChE in each fraction (rH) was detected by Enzyme Antigen Immunoassay (Liao et al., 1992) using a specific mAb (101-1) raised against human brain AChE. Endogenous AChE activity in uninjected tadpoles (Fr) was determined by the standard calorimetric assay described herein above (general procedures). Percent enzyme activity in each fraction (average±SEM) is shown for 3–5 groups of 3 embryos from a single microinjection experiment. LS—Low salt soluble; DS—Detergent soluble; HSS—High salt soluble.

(e) Assembly of rHAChE in Xenopus embryos. In FIG. 11 there is shown the results depicting the assembly of rHAChE in Xenopus embryos, namely, the rHAChE in microinjected embryos remains monomeric. In these experiments, high salt/detergent extracts representing 2 embryos were subjected to sucrose density centrifugation as described herein above in (b), and EAIA. FIG. 11 represents total AChE (solid line) and immunoreactive rHAChE (dotted line) from CMVAChE-injected embryos 1 to 4 days post-fertilization. rHAChE appeared exclusively as a peak representing monomeric AChE (approximately 3.2 S) at all time points. Arrow marks position of bovine liver catalase (11.4 S). INSETS: AChE molecular forms in control uninjected embryos scaled to the total activity levels observed in DNA-injected embryos (see FIG. 9). Peak analysis demonstrated that the distribution of oligomeric forms was identical to that observed in CMVAChE-injected embryos. Note that monomeric AChE is essentially undetectable in control embryos. G1, G2, and G4 indicate the expected positions of the globular monomer, diner, and tetramer in the gradient; A8 and 12—positions of "tailed" asymmetric forms. Fraction 0 represents the top of the gradient.

Thus, the above experiments which were performed to examine the possibility that heterologous human AChE could undergo homomeric oligomeric assembly or interact with either catalytic or non-catalytic subunits of Xenopus AChE to produce hybrid oligomers, showed that at all time points examined, rHAChE appeared exclusively as non-assembled monomers sedimenting at approximately 3.2 S, despite the concomitant accumulation of various multimeric forms of the endogenous frog enzyme (FIG. 11). When oligomeric AChE purified from CMVAChE-transfected cell cultures (Velan et al., 1991b) or from human brain (Liao et al., 1992) was preincubated with extracts of day 3 uninjected embryos and similarly analyzed, monomers, dimers, and tetrameres were detected, and the distribution of oligomeric forms observed was identical to control samples. Thus, mAb 101-1 detects all the globular configurations of rHAChE, and proteolytic activity does not appear to degrade stable oligomeric AChE in embryo extracts. Endogenous Xenopus AChE appeared primarily as a dimer on day 2 PF with globular tetrameric and asymmetric tailed forms appearing and increasing from day 3 onwards (FIG. 11, insets). Superimposition of the gradients from control and CMVAChE-injected embryos demonstrated that the normal developmental progression of Xenopus AChE oligomeric assembly was conserved in CMVAChE-injected embryos despite the high excess of rHAChE monomers (FIG. 11, and data not shown).

(f) Subcellular disposition of rHAChE in myotomes of CMVAChE-injected embryos. In FIG. 12 there is shown the results (electron micrographs) depicting the disposition of rHAChE in myotomes from two day old microinjected Xenopus embryos. In these experiments, fertilized Xenopus eggs were microinjected with 1 ng CMVAChE, incubated for 2 days at 17° C., fixed, stained, and prepared for electron microscopy as described herein above (general procedures). Uninjected embryos from the same fertilization served as controls and were similarly treated. Arrows mark accumulations of reaction product indicating sites of catalytically active AChE. Each of the electron micrographs in FIG. 12 shows: A) Uninjected control myotome in longitudinal section following activity staining for AChE; B) Myotome section from CMVAChE-injected embryo; C) Uninjected control myotome in transverse section; and D) Transverse section from CMVAChE-injected embryo. Note the increased intensity of staining in sections from injected embryos vs. uninjected controls within the same subcellular compartments, especially within the sarcoplasmic reticulum (SR). A—A band; I—I band; Z—Z disc; Tr—triad; Sr—sarcoplasmic reticulum; T—T tubulus; g—glycogen particles; Size bar represents 0.5 μm.

It should be noted that the whole-mount cytochemical staining of CMVAChE-injected embryos (results not shown) indicated an accumulation of AChE in myotomes 2 days post-fertilization (PF). Thus the above and below described ultrastructural analysis with the electron microscope was carried out on 2 and 3 day old embryos, the embryos being CMVAChE-injected and normal, uninjected controls.

In FIG. 13 there is shown the results (electron micrographs) depicting the overexpression of AChE in myotomes of CMVAChE-injected embryos which persists to day 3. PF. In these experiments the analyses were as mentioned above in respect of those whose results are shown in FIG. 12, except that embryos were analyzed after 3 days incubation. Note the developmental increases in myotomal AChE in both control uninjected (micrographs A, C) and CMVAChE-injected (micrographs B, D), especially within the Sr and T-tubules. Size bar represents 0.5 μm.

Thus, the above ultrastructural analysis shows that clearly discernible myofibers are presents 2 days PF in both injected and uninjected embryos (FIG. 12). By day 3 PF, both groups displayed significant increases in their numbers of myofibrillar elements and in maturation of the sarcoplasmic reticulum (SR; FIG. 13). To examine the subcellular localization of nascent AChE in transgenic and control embryos, applicants employed cytochemical activity staining (Karnovsky, 1964). In both the experimental and control groups, crystalline deposits of electron dense reaction product were observed primarily in association with myofibrils, amidst the myofilaments and within the SR (FIGS. 12 and 13). Various organelles, including the nuclear membrane, free and bound polyribosomes, golgi, and sometimes mitochondria were also observed to be stained (FIGS. 12 and 13 and data not shown).

Figure 13A:
FIGS. 13(A–D) shows the results (electron micrographs) depicting the overexpression of AChE in myotomes of CMVAChE-injected embryos which persists to day 3 PF, as described in Example 2.
Figure 13B:
Figure 13C:
Figure 13D:

At day 2 PF, staining in CMVAChE-injected embryos was conspicuously more pronounced than that observed in uninjected controls, both in the quantity and intensity of reaction product (FIG. 12). However, variability was observed between tissue blocks, probably reflecting mosaic expression of the injected DNA and/or variability in the efficiency of expression between embryos (not shown). In longitudinal sections from CMVAChE-injected embryos, staining appeared to be concentrated at the I band of myofibers, particularly around the triad marking the intersection of the SR and T-tubule systems. In contrast, the sparse staining observed in control sections appeared randomly distributed. By day 3 PF, the general staining intensity in both groups had significantly increased, while observable differences between the groups were less dramatic. Cross sections revealed especially prominent staining within the SR (FIG. 13 A, B). Strong staining was now observed at both the A and I bands, and for the first time, within the T-tubules (FIG. 13C, D). Overall, day 2 CMVAChE-injected myotomes resembled day 3 uninjected control myotomes in staining incidence and intensity (FIGS. 12A, C and 13B, D).

(g) Ultrastructural consequences of overexpressed AChE in Xenopus neuromuscular junctions (NMJs). Applicants have previously demonstrated up to 10-fold overexpression of catalytically active AChE in NMJs of CMVAChE-injected embryos 2 days PF (Ben Aziz-Aloya et al., 1993). To examine the persistence of this state and its implications for synaptic ultrastructure, a series of experiments were carried out, the results of which applicants presented in FIG. 14 and Table III (below). In the experiments, the results (electron micrographs) of which are shown in FIG. 14, fertilized Xenopus eggs were cultured for 3 days, fixed, stained for AChE catalytic activity and examined by transmission electron microscopy as described herein above. Two cytochemically stained synapses are presented from uninjected control (micrographs A–B) and CMVAChE-injected (micrographs D–E) embryos. Note the particularly high density staining in areas directly opposite nerve terminal zones enriched in neurotransmitter vesicles (V). Micrographs C, F illustrate representative unstained NMJs from a control and a CMVAChE-injected embryo, respectively. The synapse presented in micrograph B represents the highest degree of staining observed in a control section. mf—myofibril; v—pre-synaptic neurotransmitter vesicles; Arrows—post-synaptic folds.

Eight representative synapses from CMVAChE-injected or control uninjected embryos were assessed for post-synaptic membrane length in $\mu$m (PSL), the sum total length covered by reaction product in $\mu$m (SL), the fraction of nerve-muscle contact distance displaying reaction product (SL/PSL), and the total stained area in $\mu$m2 (SA). Average values (Av.)±Standard Deviation (SD) are presented. Measurements were performed on EM photographs using a hand-held mapping device.

Figure 14A:
FIGS. 14(A–F) shows the results (electron micrographs) of fertilized Xenopus eggs cultured for 3 days, fixed, stained for AChE catalytic activity and examined by transmission electron microscopy, as described in Example 2.
Figure 14B:

The above ultrastructural analysis revealed the following: In the injected group, 72% of the post-synaptic membrane length (SL/PSL/Table III) was stained, on average, for active AChE. In contrast, only 22% of the post-synaptic length was stained in controls. Moreover, the total area covered by reaction product was approximately 4-fold greater in NMJs from CMVAChE-injected embryos than those from controls (SA, Table III). In addition, the staining observed in NMJs from injected embryos was considerably more intense than that displayed by control NMJs, forming large black accumulations of reaction product as opposed to the lighter, more diffuse staining observed in controls (FIGS. 14A–B, D–E).

Figure 14C:
Figure 14D:
Figure 14E:
Figure 14F:
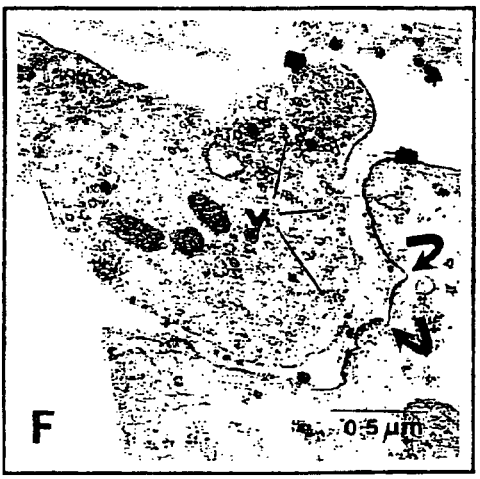

Ultrastructural features of NMJs from injected and uninjected embryos were best discerned in unstained synapses. NMJs from control embryos generally appeared smooth and relatively undeveloped, with up to 2 secondary folds of the post-synaptic membrane, and a single nerve-muscle contact (FIG. 14C). In contrast, NMJs from CMVAChE-injected embryos displayed an average of 3 secondary folds and 1–3 discrete contacts between pre- and post-synaptic membranes (FIG. 14F). Furthermore, the average post-synaptic membrane length in NMJs from CMVAChE-injected embryos was 30% larger and considerably less variable than that measured in control embryos (SL, Table III). Yet, the distance across the synaptic cleft was both larger and more variable in injected embryos than in controls (129 72 $\mu$m vs. 94±23 $\mu$m; N=14). NMJs overexpressing rHAChE thus appeared more developed in their structural buildup than controls.

Thus, from the findings and observations set forth in Example 2 above the following conclusions can be made: The efficacy of the CMV promoter in DNA-microinjected *Xenopus* oocytes was demonstrated by the observation that 5–10 fold higher levels of heterologous enzyme (AChE), encoded by an expression vector under CMV promoter control, were expressed as compared to levels induced by microinjection of in vitro transcribed mRNA. Although no direct interactions between rHAChE and endogenous *Xenopus* AChE catalytic or structural subunits were observed, calculations of *Xenopus* AChE levels in microinjected embryos indicated that some feedback regulation may be operative in repressing endogenous AChE biosynthesis under conditions of overexpression. Ectopic gene expression/overexpression often results in gross morphogenic aberrations (Sokol et al., 1991). Yet, applicants found that *Xenopus* embryos can tolerate large excesses of catalytically active heterologous (human) AChE without suffering gross morphological or developmental abnormalities. This observation is especially interesting in light of evidence implicating AChE with the early embryonic development of non-cholinergic tissues (Drews, 1975) and with developmental processes such as gastrulation and cell migration (Drews, 1975; Fitzpatrick and Stent, 1981), nerve outgrowth and differentiation (Layer, 1991) and proliferation and differentiation of hematopoietic cells (Lapidot-Lifson et al., 1989, 1992; Patinkin et al., 1990). As neither the overall rate of development nor general morphology of CMVAChE-injected embryos was altered by 50 to 100-fold excesses of the active enzyme at the gastrula stage, our findings do not support a role for recombinant human (rHAChE) in modulating cell growth, proliferation, or movement in very early *Xenopus* embryogenesis. However, since these biological activities may be unassociated with acetylcholine hydrolysis, they may demonstrate species-specificity and remain undetected in our system.

The characteristic subcellular segregation of overexpressed rHAChE in muscle may reflect either tissue-specific biosynthesis or posttranslational processing of nascent enzyme present in myotomal progenitor cells at the onset of myogenesis. The high levels of rHAChE present in gastrula stage embryos may argue for the latter possibility. In that case, the cytochemical data indicate the existence of an intrinsic, evolutionarily conserved property directing the subcellular trafficking of AChE in muscle, and thus explain the accumulation of rHAChE in NMJs of AChEDNA-injected embryos. Furthermore, these results may imply that cotranslational processes are not required for the correct compartmentalization of AChE in muscle cells.

The general state of myotomal overexpression induced by microinjection of CMVAChE persisted at least 3 days. The area covered by reaction product in cytochemically stained NMJs from day 3, CMVAChE-injected embryos was 4–5 fold greater than observed in controls. This figure represents a 2-fold lower excess than that measured in day 2 NMJs (Ben Aziz-Aloya et al., 1993) yet is slightly greater than the ratio of recombinant human to frog AChE as determined in homogenates at day 3 (FIG. 10A). This apparent reduction in the level of synaptic overexpression from day 2 to day 3 PF may reflect the overall decline in total rHAChE activity observed during this period. However, since this calculation does not consider the higher density staining observed in NMJs from CMVAChE-injected embryos, it represents an underestimate of the actual synaptic AChE content. Therefore, our data indicate enhanced stability of rHAChE at the NMJ compared to the total pool, a conclusion consistent with the observation that extra-cellular matrix-associated AChE persists in situ long after denervation of adult frog skeletal muscle (Anglister and McMahan, 1985).

Mammalian cells cotransfected with cDNAs encoding catalytic and non-catalytic AChE subunits (Krejci et al., 1991) produce multimeric globular and asymmetric AChEs, indicating that spatial coexistence may normally be the only requirement for multimeric assembly. Human cell lines transfected with various CMVAChE constructs similarly express and secrete homo-oligomers (Velan et al., 1991a; Kronman et al., 1992). In the present case, rHAChE displayed oligomeric assembly in microinjected *Xenopus* oocytes, but not in developing embryos where only monomeric rHAChE was detected. Nonetheless, rHAChE was found to accumulate in its natural subcellular compartments and was correctly transported to the NMJ of transiently transfected tadpoles.

In humans, ultrastructural and physiological alterations of the neuromuscular junction have been associated with congenital AChE and AChR deficiencies (Jennekens et al., 1992) and may be associated with changes in the balance between these two molecules at the synapse. In one of these syndromes, patients presented, in addition to AChE/AChR deficits, NMJs displaying decreased miniature end plate potentials, reduced post-synaptic membrane lengths, and severely impaired post-synaptic secondary folding. These observations are in contrast to those observed in our NMJs overexpressing AChE.

Example 3

Figure 15:
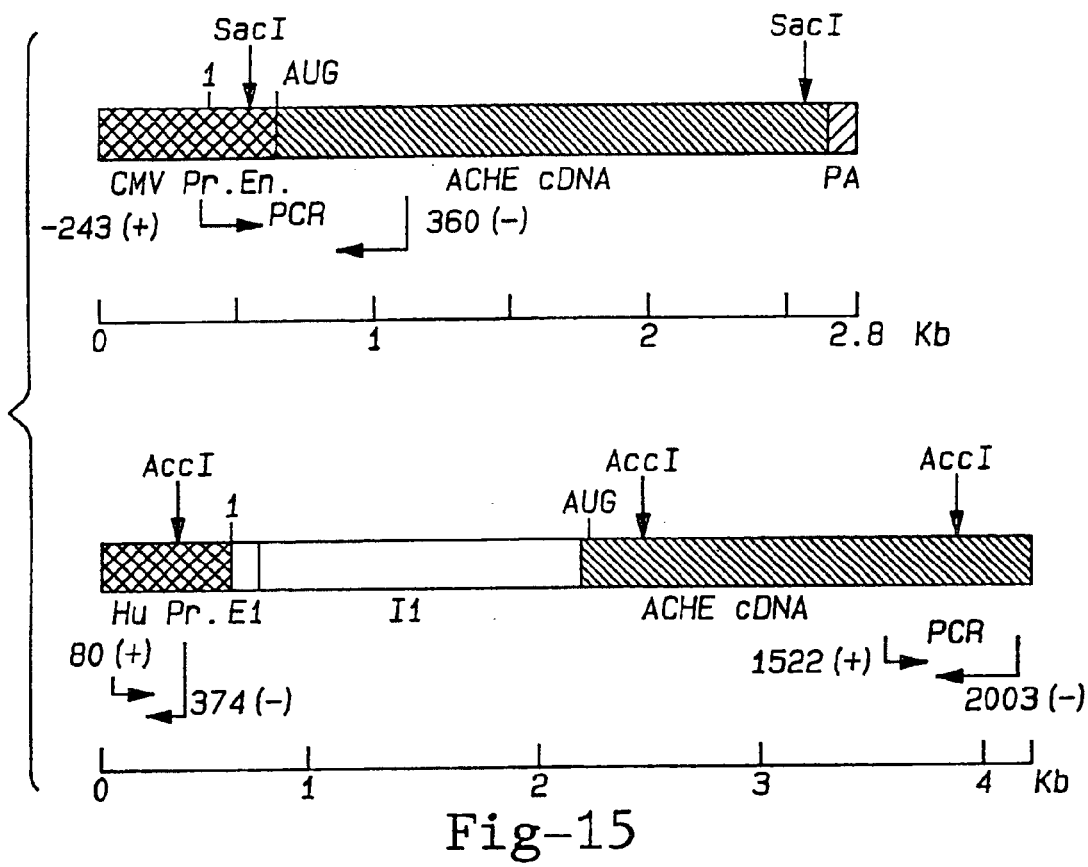
FIG. 15 presents two DNA constructs, CMV-ACHE and HpACHE, used to prepare transgenic mice, as described in Example 3.

Establishment of Stably Transgenic Mouse Lines Expressing the Human AChE Gene (a) Establishment of transgenic mouse pedigrees. Two DNA constructs were employed: one with the pan-active cytomegalo-virus (CMV) promoter (Velan et al., 1991) and AChEcDNA (see Example 2 above) and the other with 600 bp from the authentic human ACHE promoter followed by the first intron from the AChE gene HpACHE (Ben Aziz-Aloya et al., 1993) to improve its regulation in the transgenic mice, and the AChEcDNA sequence encoding this enzyme. Both transgenes included the full coding sequence for human AChE (Soreq et al., 1990) and were shown to be expressible in *Xenopus* oocytes and embryos, with the CMV promoter being 20-fold more efficient than HpACHE in promoting AChE production (Ben Aziz Aloya et al., 1993, Seidman et al., 1994). FIG. 15 presents these two DNA constructs, their composition and the positions on them of PCR primers employed to detect their presence in the transgenic mice (for details concerning the sequence of the ACHE gene in the above constructs see Example 1 above). The transgenic mice were prepared by standard procedures of transformation to obtain transgenic animals, as set forth, for example, in (Shani, 1985).

Injecting over 70 eggs resulted in one pedigree carrying the transgene with the CMV promoter (HpACHE) and three others with variable copy numbers of the construct carrying the human ACHE promoter. Three independent pedigrees of transgenic mice carrying the human AChE promoter-reporter construct were established. Further experiments were carried in the descendent generations of mice from these pedigrees, all of which presented grossly normal development and behavior.

Figure 16:
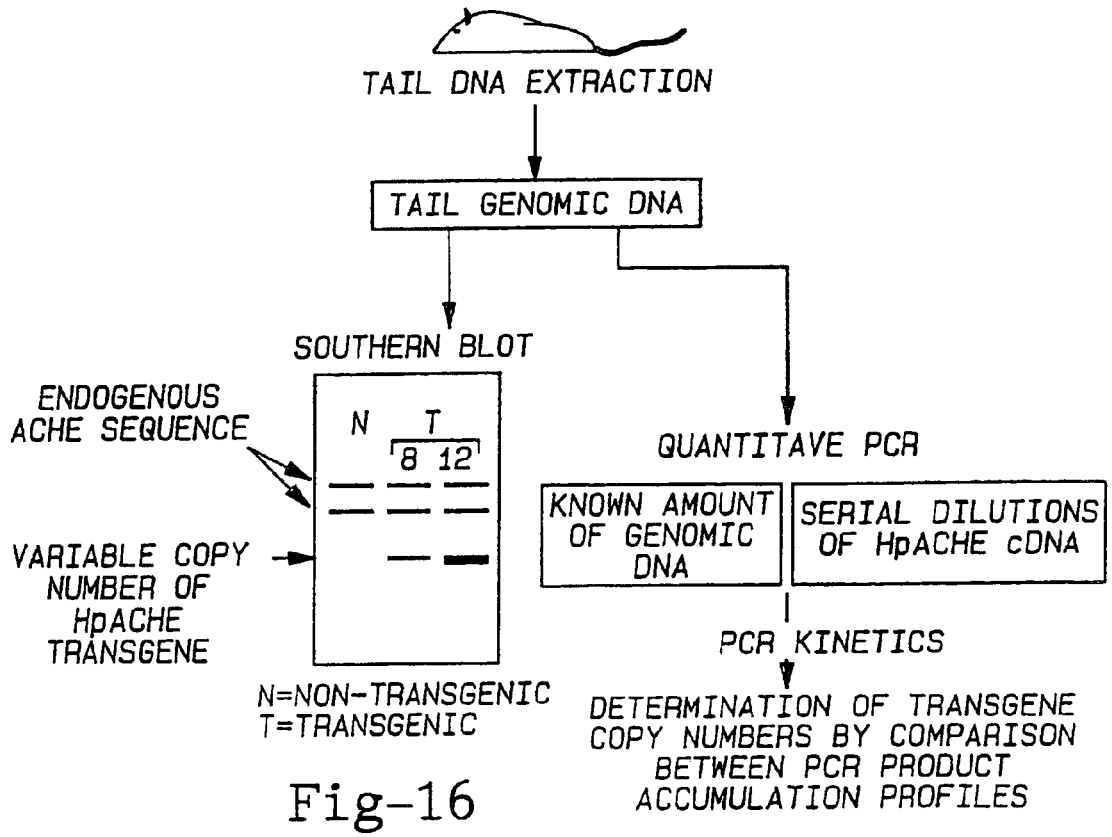
FIG. 16 shows a schematic representation of transformation procedures to prepare transgenic mice and representation of blot hybridization results obtained from transgenic mice, as described in Example 3.
Figure 17:
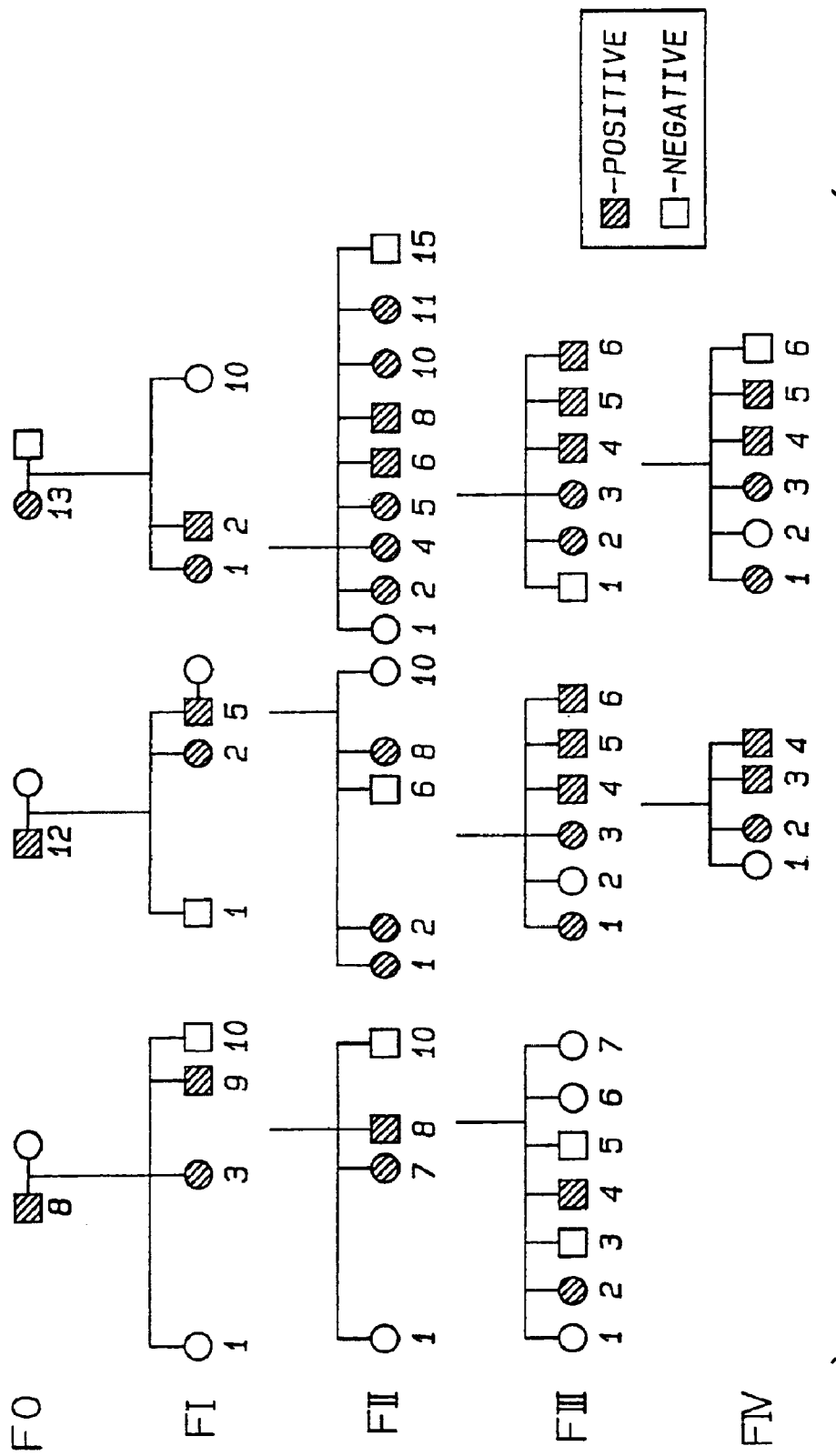
FIG. 17 is a schematic presentation of transgenic mice family pedigrees; the closed squares and circles indicating positive, i.e. transgenic animals and the open squares and circles indicating negative, as described in Example 3.

(b) Determination of copy numbers. Tail DNA restriction analysis and blot hybridization were employed to differentiate between the human ACHE transgene and its murine counterpart. Kinetic follow-up of PCR amplification (Example 1 and Lev-Lehman et al., 1993) was used to quantify copy numbers of the transgene. For calibration, known amounts of the human gene were subjected to a similar procedure. Furthermore, positive mice were identified by informative PCR amplifications of tail DNA and copy numbers were evaluated by a kinetic follow-up of the PCR reactions, as confirmed by DNA blot hybridizations (see schematic representation of the procedure and the blot hybridization results in FIG. 16). The various procedures employed were standard ones for quantitative PCR and PCR kinetics determinations (see also Example 1 above and Lev-Lehman et al., 1993). FIG. 17 presents these family pedigrees. DNA blot hybridization revealed expected restriction patterns in two pedigrees with one and two copies/genome (pedigrees 8, 13 respectively) and rearrangement in another pedigree (8) with 12 copies/genome.

Thus, the above noted HpAChE construct, having the human AChE gene promoter was successfully employed to obtain transgenic mice in which the human AChE is expressed. The HpAChE pedigrees shown in FIG. 17 were obtained as follows: Three different founders (Fo, transgene presence verified as detailed above) were mated with wild type mice to create the FI generation. Mating of FI mice, with wild type mice gave rise to the FII generation. FIII mice were generated by mating of FII×FII mice. Note the increase in the fraction of positive transgenic mice (closed squares and circles, negative mice, i.e. non-transgenic being those shown by open squares and circles in FIG. 17) within pedigrees 12, 13, but not 8, from Fo to FIV and the gradual decrease in litter size, indicating selection disadvantage of the transgene at the germ line and/or early embrybgenesis levels.

However, it should be noted that in three separate DNA construct preparations and microinjection procedures, applicants could not get any transgenic mice carrying and expressing the. CMV-AChE construct, although this construct was efficiently expressed in *Xenopus* oocytes and embryos (Example 2 above). In view of the strength of this promoter (CMV), as compared with the HpAChE one (Ben Aziz-Aloya et al., 1993), this indicates that high levels of AChE expression may be lethal in embryonic stages and/or in the process of fertilization in mammals. Accordingly, for the preparation of transgenic mammals (e.g. mice, rat, etc.), the preferred vector is the one with the human AChE promoter, e.g. the HpAChE vector.

(c) Phenotypic observations in transgenic mice carrying the HpAChE construct. Three primary sites for AChE expression are brain and neuromuscular junctions (NMJ), where the enzyme product of this gene controls termination of neurotransmission (Soreq and Zakut, 1990), and hematopoietic cells, in which a growth-regulatory role was proposed for AChE (Paoletti et al., 1992). In search for the biological role(s) of the transgene product, applicant therefore examined these three sites for expression of the transgene and phenotypic alterations.

(i) Brain. Brain general morphology was apparently normal in the examined transgenic mice, and subtle differences, if they exist, may be detected following analysis by immunohistochemical staining. Species-specific RNA-PCR examination of total brain RNA using human AChE specific primers revealed human-specific PCR products in two transgenic brains from family No. 13 but not in two control brain RNA samples and not in one brain from family No. 8 and one from family No. 12. Thus human AChEmRNA is expressed in adult brain of the transgenic mice. To examine whether active enzyme was produced from the transgene, homogenates from whole brains were incubated in multiwell plates covered previously with monoclonal anti-AChE antibodies selective for the human enzyme. Following washes, acetylthiocholine hydrolysing activities were measured in duplicates by the Ellman spectrophotometric procedure, as detailed above (Example 2). Recombinant human AChE, produced in bacteria from the same DNA, using standard procedures, served as a control. Table IV demonstrates that duplicate brain homogenates from transgenic, but not control mice displayed binding of active enzyme to this mAb (see Example 2 for details regarding the mAb employed).

Figure 18:
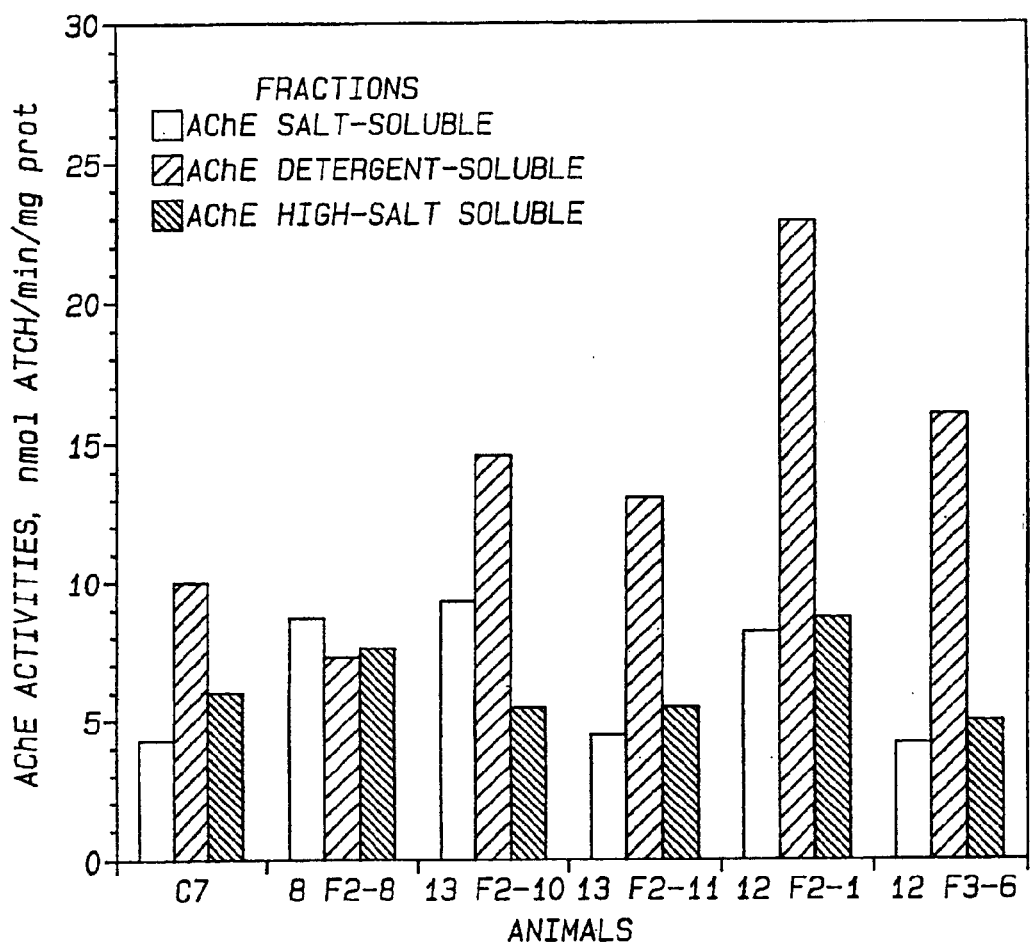
FIG. 18 shows the results depicting the overexpression of AChE in the detergent-soluble fraction of muscle homogenates from the HpAChE-transgenic mice, as described in Example 3.

(ii) Muscle. Specific activity of AChE was determined following subcellular fractionation of homogenates of transgenic and control muscles, using the Elman spectrophotometric procedure in the presence of the specific BCHE inhibitor ISO-OMPA (see also Example 2 with respect to experimental details). In FIG. 18 there is shown the results depicting the overexpression of AChE in the detergent-soluble fraction of muscle homogenates from the HpAChE-transgenic mice. Muscle extractions and detergent and salt fractionations were performed as detailed above (Example 2). Note the increase in amphiphylic, but not membrane-associated or soluble AChE in correlation with the transgene copy number. The different fractions are denoted by differently colored bars, the key to which appears on the right hand side of FIG. 18. Thus, from FIG. 18 it is apparent that higher activity is observed in the transgenic samples (especially in the detergent soluble fraction) in correlation with the transgene copy number (8<13<12). Immunoassays revealed no human AChE enzyme bound to the plate.

Figure 19:
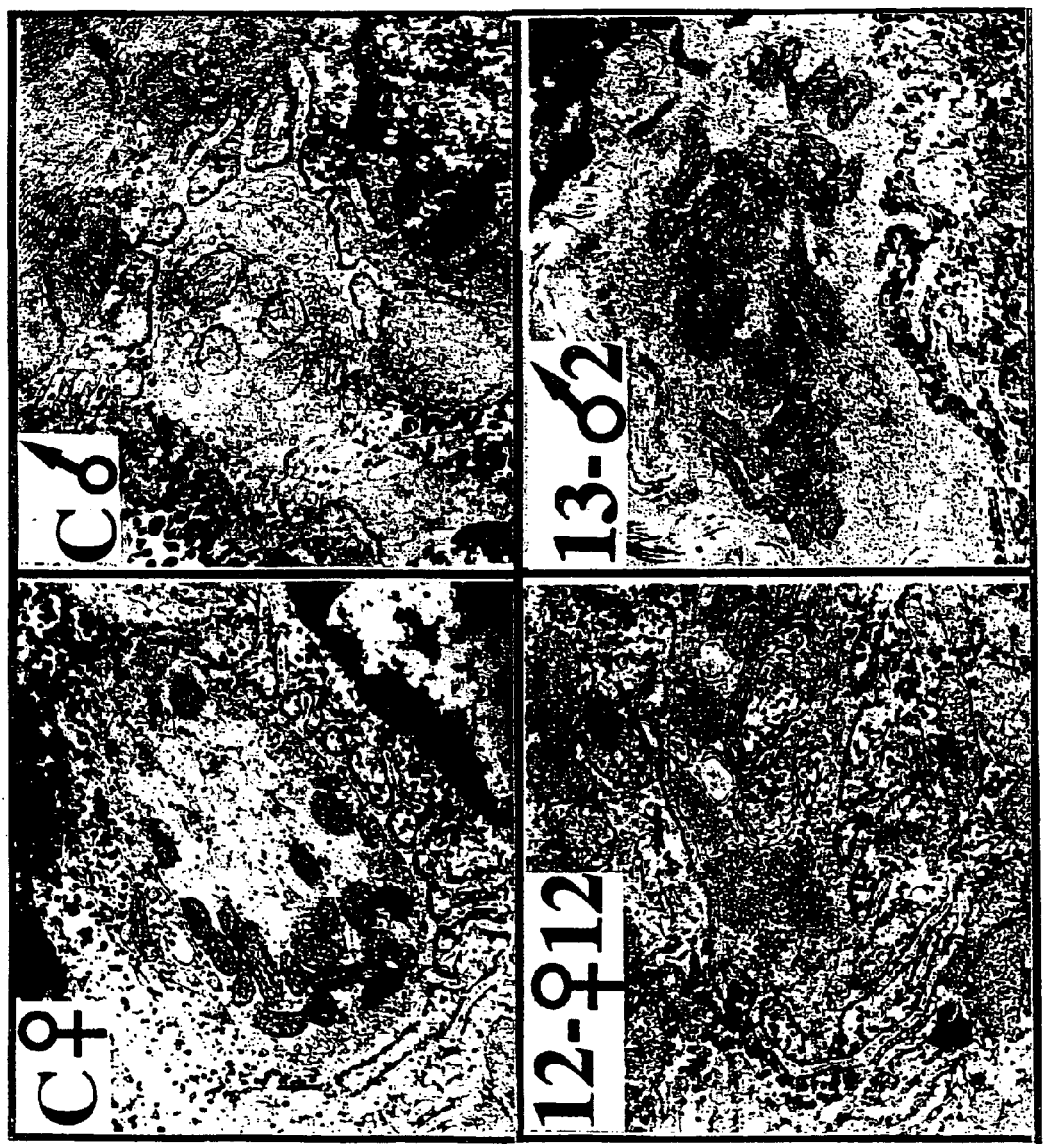
FIG. 19 shows electron micrographs from tongue synapses from the two transgenic mice (12-12, female and 13-2, male) described above (FIG. 17) that were analyzed by E.M. cytochemistry in comparison with parallel synapses from age and sex-matched controls, as described in Example 3.

(iii) Neuromuscular Junctions. Neuromuscular junctions (NMJ) in three HpAChE transgenic mice were examined for their structural buildup and AChE expression. To this end, applicants performed electron microscopy studies of tongue synapses (tongue muscle NMJ structures) following cytochemical staining for AChE activity. In FIG. 19 there is shown electron micrographs from tongue synapses from the two transgenic mice (12-12, female and 13-2, male) described in (b) above (FIG. 17) that were analyzed by E.M. cytochemistry (Example 2 above and Ben Aziz-Aloya et al., 1993) in comparison with parallel synapses from age and sex-matched controls (c, female and c, male). Note longer, curled post-synaptic folds with conspicuous enzyme staining and denser vesicles in the transgenic mice. Thus, from FIG. 19 it is apparent that NMJ structures from the transgenic mice displayed excessively long and curled post-synaptic folds which were closely spaced and filled with reaction product. Moreover, there was high density of membrane vesicles in the nerve terminals, all as compared with parallel NMJ from control mice. This demonstrated active participation of the AChE gene in synaptic development, in agreement with our observations of such involvement, in the developing NMJ of *Xenopus* embryos (Example 2 above). The observed NMJ alterations further indicated adjustment of the hierarchic control of cholinergic signaling in the transgenic NMJ. Such hierarchic control could, by feedback regulation, adjust the amount of key synapse proteins to enable correct neurotransmission even under conditions of overexpressed transgenic AChE. The reciprocate indication which stems from these observations is that underexpression of the AChE gene (i.e., in cases of prolonged exposure to inhibitors) may cause defects in NMJ development.

Figure 20:
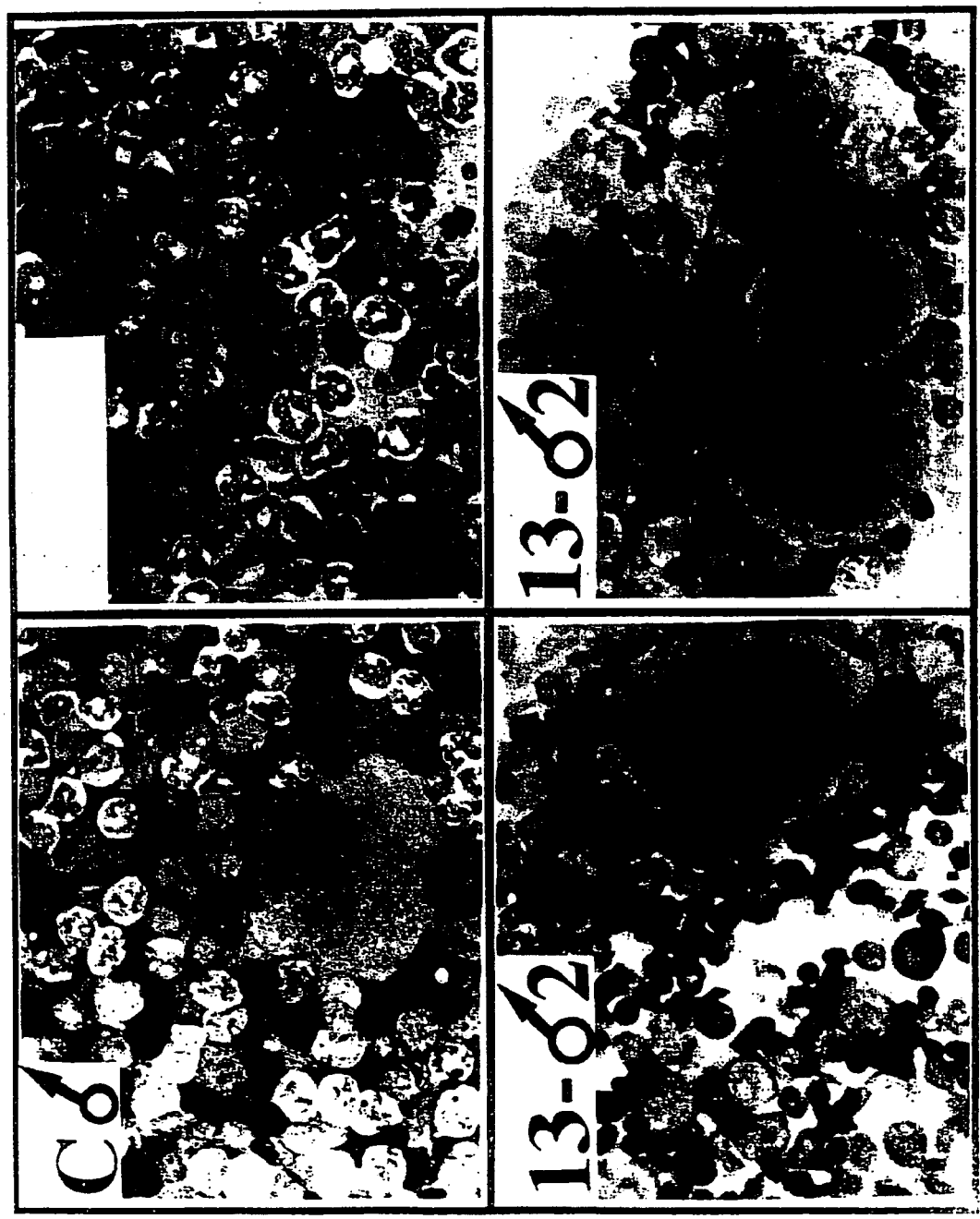
FIG. 20 shows electron micrographs from bone marrow smears from two FI transgenic mice (12-12, female and 13-2, male marked as in FIG. 17) and one control (C, male) stained with Giemsa, as described in Example 3.
Figure 21:
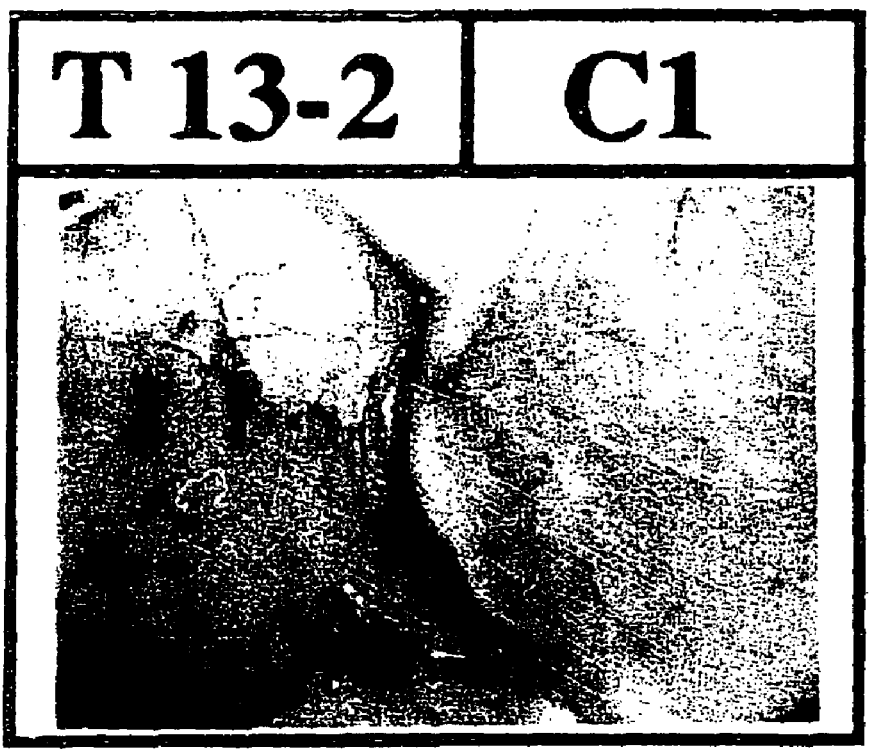
FIG. 21 shows a photograph, taken during post-mortem (P.M.) analysis, which shows multiple internal subcutaneous bleeding sites in the 13-2 transgenic mouse (T 13-2) but not in an age and sex-matched control (C1), as described in Example 3.

(iv) Hematopoietic Cells. Preliminary findings with 8 transgenic mice revealed striking phenotypic differences in bone marrow composition of some mice (Table V, below). Representative changes are demonstrated in FIG. 20 for transgenic mice of the F1 generation. In FIG. 20 there is shown electron micrographs from bone marrow smears from two FI transgenic mice (12-12, female and 13-2, male marked as in FIG. 17) and one control (c, male) were stained with Giemsa. Note lymphocytes and erythroid cells in the female mouse 12-12 as opposed to increase in erythroid cells and megakaryocytes, which share a common progenitor, in the male mouse 13-2. Thus, numerous megakaryocytes appeared in the FI male (with 2 HpAChE copies). This defect in megakaryocytopoiesis, was accompanied by a conspicuous phenomenon of subcutaneous bleeding in this particular FI male, reflecting a serious aberration in platelet production. In FIG. 21 there is shown a photograph, taken during post-mortem (P.M.) analysis, which shows multiple internal subcutaneous bleeding sites in the 13-2 transgenic mouse (T 13-2) but not in an age and sex-matched control (C1). It should be noted that applicants have previously observed a similar phenotype of multiple immature megakaryocytes in the bone marrow and extremely low platelet counts in a Lupus Erythematosus patient with AChE gene amplification in her peripheral blood cells (Zakut et al., 1992). Significant increases in erythroblasts and normoblasts, compensated by decreases in granulocytes occurred in transgenic mice (Table V below).

Figure 22A:
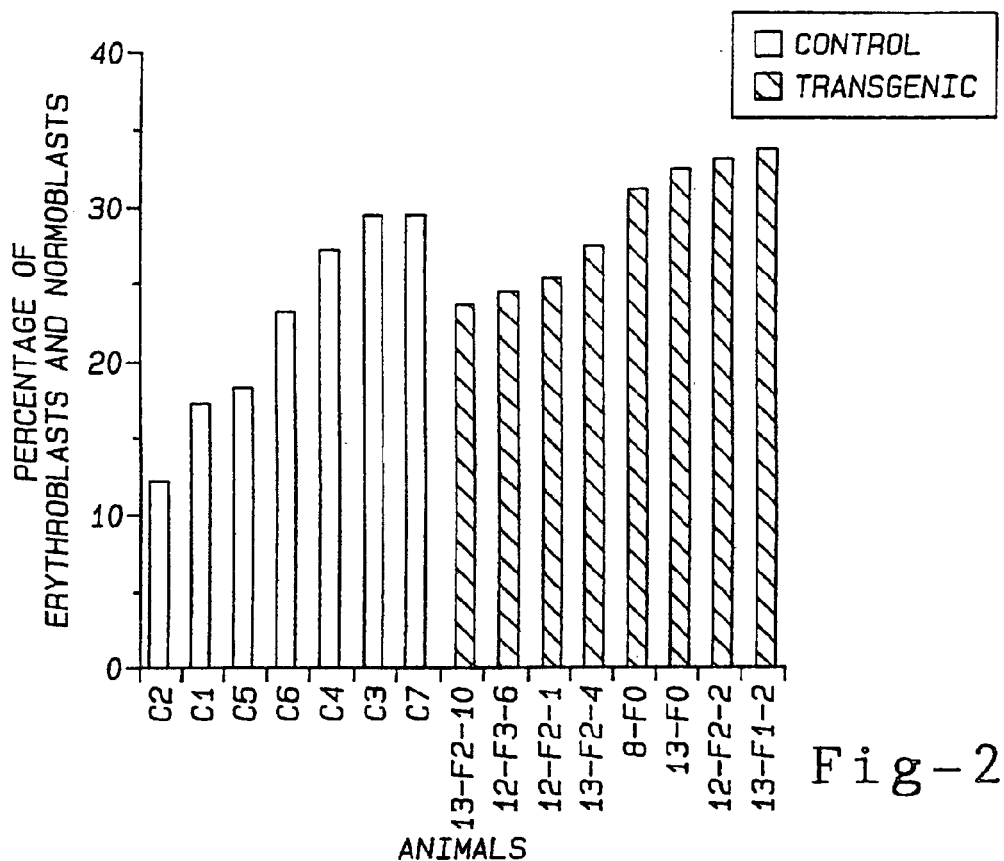
FIGS. 22(A, B) shows the results depicting the lower variability in bone marrow composition and enhanced erythropoiesis in HpAChE transgenic mice, as described in Example 3.
Figure 22B:
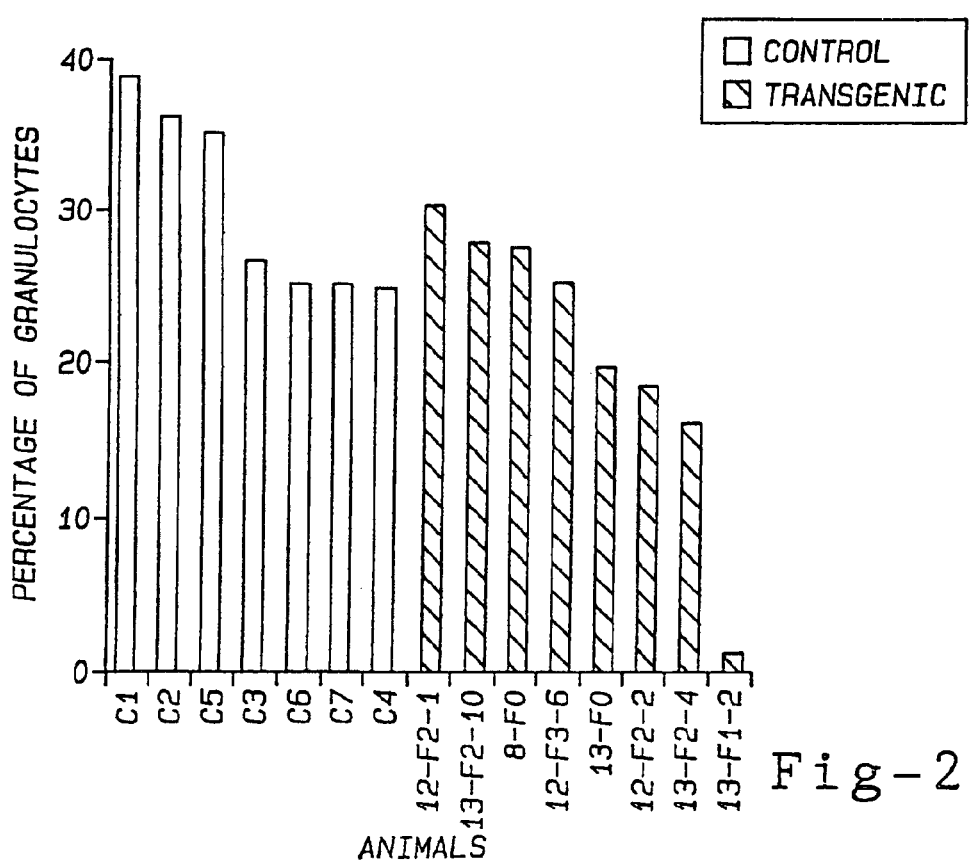

In FIGS. 22(A, B) there is shown the results depicting the lower variability in bone marrow composition and enhanced erythropoiesis in HpAChE transgenic mice. Differential cell compositions were determined in fresh bone marrow smears from the 8 noted transgenic mice and 8 age and sex-matched controls, wherein FIG. 22A shows the percentages of erythroblasts and normoblasts and FIG. 22B shows the percentages of granulocytes in the control (open bars) and transgenic (closed bars) animals. Note the limited variability (22–35%) of red blood cells in the transgenic vs. controls (12–30%), and the higher average content of red cells in the transgenic mice.

Thus, from FIG. 22 it is apparent that the percentage of erythroblasts and normoblasts in the transgenic mice is significantly less variable in the transgenic bone marrow than in the control mice and reached higher values (average 28.9% as compared with 22.4% for 8 mice in each group). An average percentage of granulocytes in the transgenic mice was lower than in the control mice (20.3% as compared with 29.7%).

Figure 23:
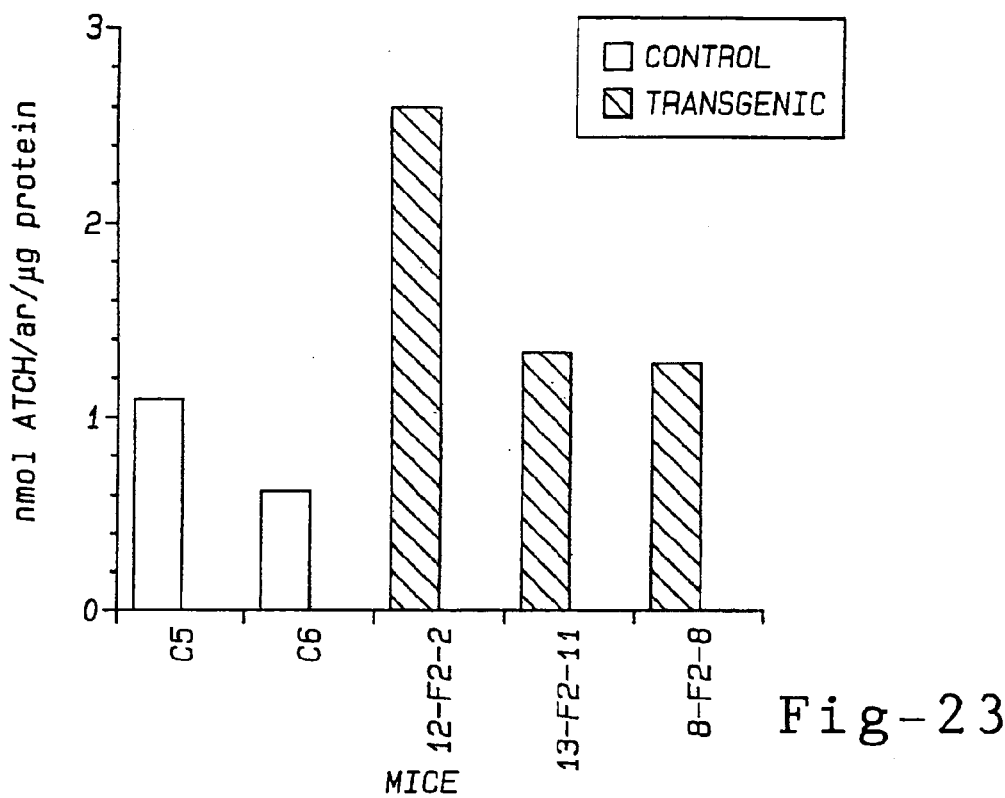
FIG. 23 represents the BW sensitive AChE activities in bone marrow from two control (open bars) and three transgenic mice (closed bars), demonstrating that the transgenic bone marrow contains high levels of AChE activity, as described in Example 3.

AChE activities in bone marrow were measured by the Elman spectrophotometric procedure, with or without BW (see Example 2 above), a selective and specific AChE inhibitor. FIG. 23 represents the BW sensitive AChE activities in bone marrow from two control (open bars) and three transgenic mice (closed bars), demonstrating that the transgenic bone marrow contains high levels of AChE activity.

Differential cell counts were determined in percentage by observing cell shape, size and histochemical staining for each of the noted mice. Note distinct variations in differential cell compositions of the transgenic mice as compared with controls.

Figure 24:
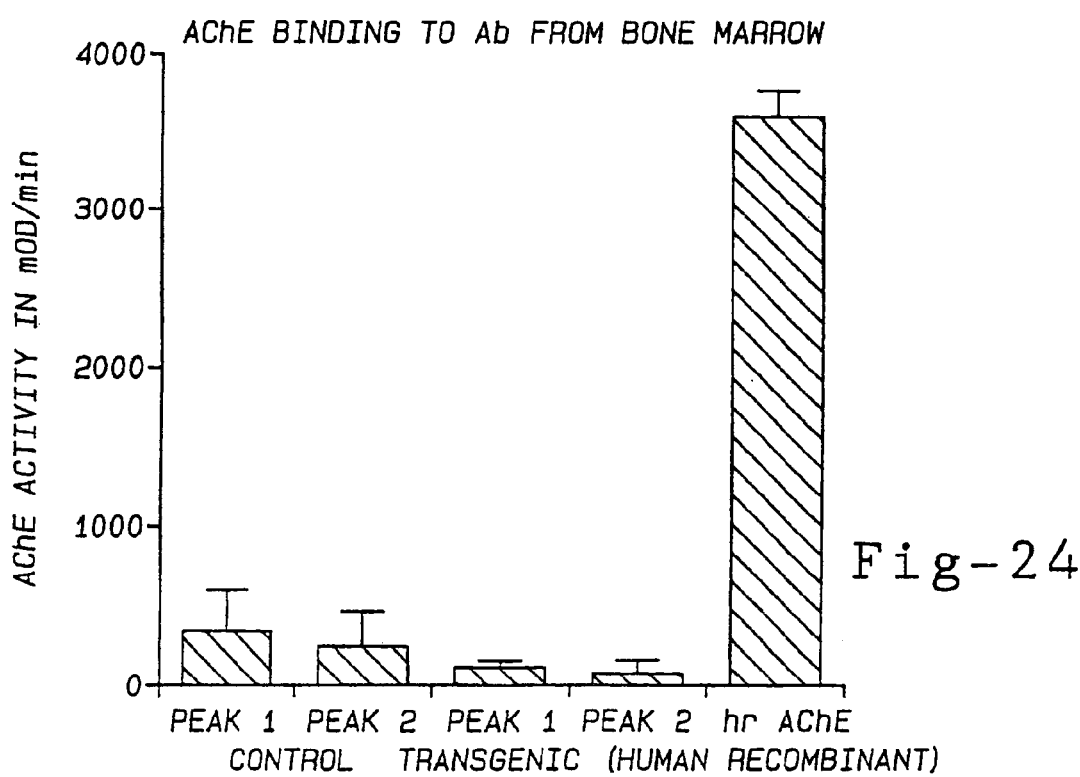
FIG. 24 shows graphically the results which indicate that the human AChE protein cannot be specifically detected in adult bone marrow of HpAChE transgenic mice, as described in Example 3.

Immunoadsorption assays using the monoclonal antibody 101-2 (specific for human AChE, see also Example 2, above) did not show any difference between the bound activity of homogenates from control and transgenic bone marrow (active fractions from the gradients were concentrated together). In FIG. 24 there is shown the results which indicate that the human AChE protein cannot be specifically detected in adult bone marrow of HpAChE transgenic mice. Bone marrow homogenates from two control and two transgenic mice were analyzed for their total AChE activities and for their content of human AChE, immunoreactive with the species-selective mAb antibodies tested previously (Example 2). Note that no human-characteristic AChE could be detected in the transgenic mice, although their total bone marrow activities were apparently higher, as noted above. Recombinant human AChE served as control for the adsorbance capacity of the employed mAb. Thus, the higher activities in the bone marrow were concluded as being of murine origin, probably in megakaryocytes. To examine the proliferative potential of bone marrow cells from these transgenic mice, primary cultures of these cells were grown in the presence of recombinant interleukin-3 into colony forming units (CFU). These were composed of megakaryocytes, macrophages, polymorphonuclear cells and erythroid cells. Colony counts were lower by 80% for transgenic as compared with control mice (Table VI, herein below), suggesting that the transgene reduced the proliferative capacity of hematopoietic cells in these mice. Within surviving colonies, there were 2-fold fewer blast cells and 2-fold larger fractions of red blood cells in the transgenics as compared with controls. Thus the transgene also promoted erythropoietic differentiation in culture, in line with the abundance of erythrocytes in the bone marrow of the transgenic mice. In the presence of erythropoietin (Epo) and IL-3 in the culture medium and growth for 12 days in three experiments, the colony numbers remained 2-fold lower in the transgenic as compared with control cultures (Table VI) (i.e., the effect of the transgenic enzyme could not be compensated by Epo) but the differentials were not in line with the fresh bone-marrow differential counts (Table VI). Most importantly, addition of 2.5 $\mu$M anti-sense AChE oligonucleotide (AS-AChE) capable of destructing AChEmRNA (Lev-Lehman et al., 1993) to the CFU-GEMM cultures enhanced colony counts and cell numbers in the transgenic cultures up to the level of controls, in one out of two experiments (Table VI). Thus, the defective proliferation of bone marrow stem cells was apparently due to the overexpression of the transgenic AChEmRNA in them.

It is important to note that the transgene (i.e. that encoded by the HpAChE construct) encodes for the brain, hydrophilic form of the enzyme and not the erythrocyte specific, phosphoinositide-linked one. This implies than the alternative C-terminus (see Example 1) does not prevent the hematopoietic growth-related effect of AChE.

(v) Apoptosis in BM cultures. In search for the cause of the suppressed proliferation of hematopoietic cells from the transgenic mice, bone marrow CFU-GEMM colonies of 2 control and 2 transgenic mice were grown in the absence or in the presence of anti-sense AChE oligonucleotide (AS-AChE oligo.—see (iv) above). DNA was extracted from these colonies and was checked for the extent of apoptotic fragmentation. As applicants know from previous studies, the AS-AChE oligo prevents the apoptotic fragmentation under these conditions. One transgenic mouse showed apoptosis levels similar to the control mice, the other showed a higher level of small DNA fragments and less protection by the AS oligo.

(vi) Sucrose gradient centrifugation. Sucrose gradient centrifugation revealed similar sedimentation profiles for AChE activities from various tissues of the HpACHE transgenics and control mice, demonstrating unmodified assembly into multimeric enzyme forms. Gel electrophoresis followed by cytochemical staining likewise revealed no differences, further suggesting similar glycosylation patterns. To distinguish between the transgene-derived and the host enzyme forms, gradient fractions were incubated with human-specific monoclonal antibodies adhered to multiwell plates (Seidman et al., 1994). Up to 20% of the active enzyme in brain and 10% of the muscle enzyme, but none in bone marrow, were thus found to be of human origin. The presence of human AChE protein but not ACHEmRNA in muscle suggested that the human enzyme observed in these homogenates was contributed by motor neurons.

(vii) in situ Hybridization and Cytochemical staining. To further associate hACHEmRNA transcripts and hAChE activities with specific CNS cell types, applicants performed in situ hybridization and cytochemical staining experiments in 50 $\mu$m thick brain sections. The extensive homology between the human and mouse products lead, in both these tests, to detection of mRNA and protein from both human and mouse sources. Labeling ACHEmRNA transcripts revealed similar brain neurons in transgenic as in control sections, yet with considerably higher efficiency. The cholinoceptive hippocampal neurons were labeled with particularly high intensity, especially in the CA1 region, as were giant striatal neurons and other cell bodies in the brainstem, cortex and cerebellum. Thus expression of the HpACHER transgene was apparently confined to host nerve cells normally expressing the ACHE gene.

Intensified cytochemical staining of AChE activity was observed in brain sections from transgenic mice in all of the areas normally stained for AChE activity. Staining was particularly intense in the neostriatum and pallidum domains, demonstrating that the transgenic enzyme produced in the neuronal cell bodies decorated in the in situ tests was faithfully transported into nerve processes and suggesting that its levels were also increased in cholinergic synapses. To examine whether this enhancement in AChE activities, and the consequent expected changes in cholinergic signally caused feedback response(s) in transcription patterns, applicants prepared differential PCR displays using an arbitrary primer from pooled RNA extracted from each of the examined brain regions. At least 50 PCR products were amplified from each region. Some of these were common to all regions and others unique to specific regions. Interestingly, several of these products were drastically reduced in the transgenic brains regions as compared with corresponding controls. Moreover, certain bands appeared to be reduced in cortex, brainstem and central nuclei. Assuming expression of at least 10,000 distinct transcripts in each brain region these differences suggest suppression of several hundred genes in the transgenic mouse brain overexpressing human AChE.

Example 4

The mouse AChE gene present in the above noted transgenic animals (Example 3) were destroyed by the recently developed, and now standard, "knockout" technology to obtain an animal model with the human AChE gene alone. To delete the murine AChE gene by targeted destruction, applicants subjected the embryonic stem to homologous recombination with a neomycin resistance gene boarded by 5' and 3' fragments from the mouse AChE gene (Li et al., 1991). Neo resistant stem cells were subsequently employed according to published procedures (see, for example, Plump et al., 1992) to create, by microinjection, transgenic mice in which one of the AChE copies cannot be expressed. Cross-hybridization of such mice with the HpAChE transgenics subsequently created the next generation of HpAChE transgenic mice. These second generation transgenics were devoid of the murine enzyme altogether, so that the only AChE expressed in them was the human enzyme. The transgenic replacement yields, for the first time, an authentic animal model with which the response of human AChE to drugs and poisons can be tested in vivo.

Example 5

Transgenic animal models for assaying substances which effect AChE expression or which inhibit AChE activity. Cholinesterases (e.g. AChE) have been implicated in a number of diseases, for example, Alzheimer's disease, leukemias, carcinomas, Parkinson's disease, glaucoma, multiple sclerosis and myasthenia gravis. Accordingly, anti-cholinesterase drugs are employed to treat such diseases. Furthermore, anti-cholinesterase poisons form a broad category of agricultural and household pesticides, including various organophosphate and carbamate agents: organophosphate (OP) insecticides have been shown to be the causative agents in about 1 million acute injuries and about 20,000 deaths per year worldwide, and are also believed to increase the risk to develop leukemias in persons coming into regular contact with these substances. In fact, the teratogenic effects of several organophosphate substances on skeletal formation (Meneely and Wyttenbach, 1989) and somitogenesis (Hannenman, 1992) have been correlated to their anticholinesterase activities (see also Zakut et al., 1991). Carbamate compounds which have cholinesterase inhibitory activity are widely used as therapeutic agents and as insecticides. Various snake venoms and plant glycoalkaloids have also been shown to have anti-cholinesterase activities.

Thus, it is desirable to develop various anti-cholinesterase drugs to treat a number of diseases where cholinesterase activity is abnormal, and also to develop various agricultural and household pesticides (insecticides) which have anti-cholinesterase activity. However, to normal healthy individuals such anti-cholinesterase substances are dangerous. Accordingly, a rapid and efficient assaying system is required to screen substances having anti-cholinesterase activities for the purposes of:

(i) developing effective drugs for treating the above noted diseases, which drugs should be highly specific for the particular cholinesterase that it is desired to inhibit and should have minimal other side effects;

(ii) screening and analyzing agricultural and household pesticides, plant and animal (e.g. snake) toxins for their anti-cholinesterase activities to determine the potential health hazards presented by such substances; and (iii) developing and producing specific cholinesterases (e.g. AChE and BChE) or active fragments thereof, by recombinant DNA. (genetic engineering) methods, which cholinesterases may be used as specific agents for treating individuals who have become exposed to dangerous levels of such toxic substances at levels that effectively inhibit their own endogenous AChE and BChE enzymes.

In accordance with the present invention, such an anti-cholinesterase assay system has been developed. As mentioned in detail in the preceding Examples (Examples 1–4), transgenic animals have been prepared which express various AChE gene constructs. The advantage of these transgenic animals (*Xenopus* embryos and mice) is that they provide, for the first time, an in vivo method to assay rapidly and effectively the effect of anti-cholinesterase substances on the expression of human AChE. For example, there is described in Example 2 and 3 above, the effect of various specific AChE inhibitors (BW284C51 or BW, and ecothiophate) as compared to the specific BChE inhibitor (iso-OMPA or IO) on the levels of expression of recombinant human AChE in transgenic *Xenopus* and mice.

Figure 25:
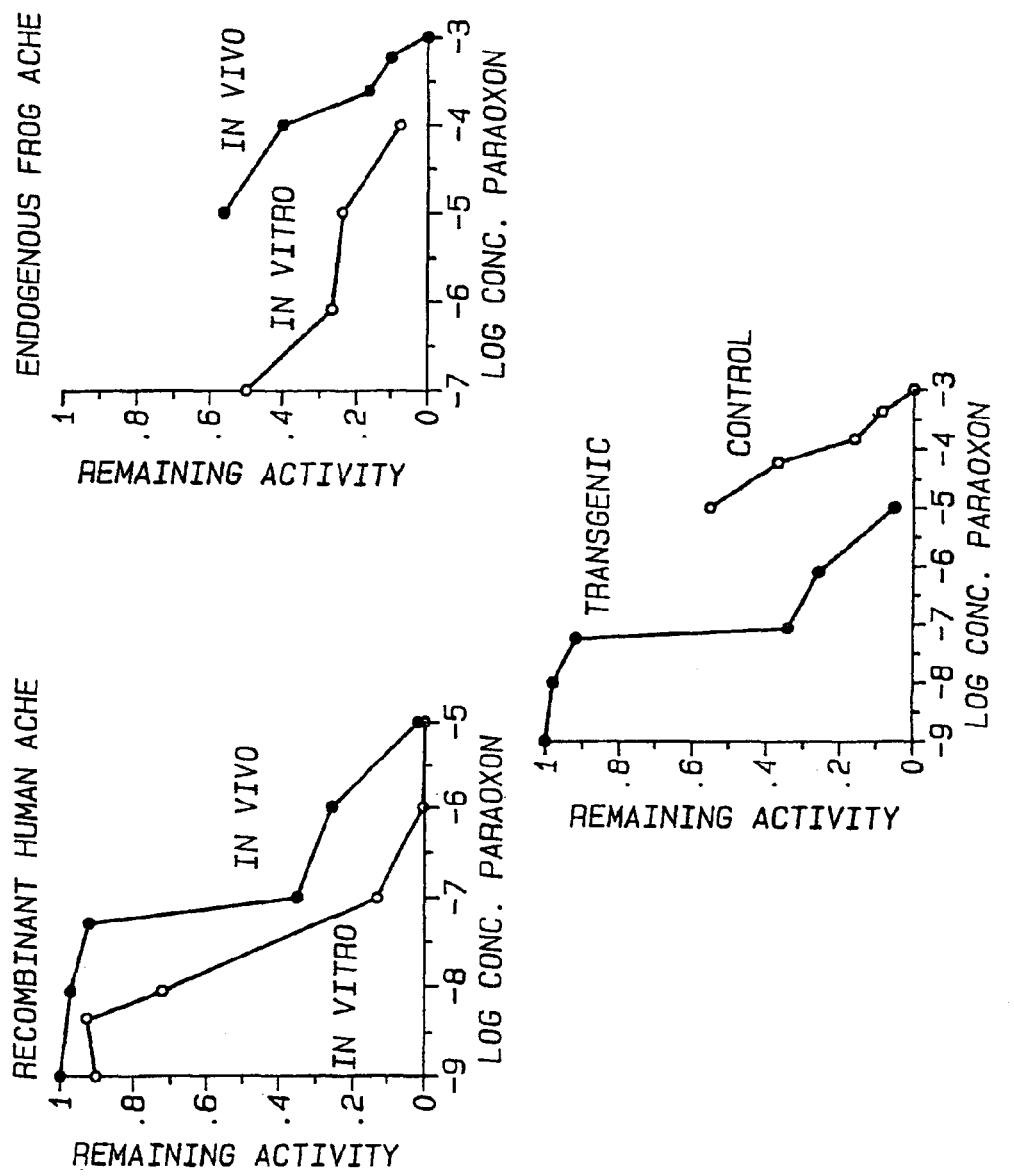
FIG. 25 shows graphically the in vivo inhibition of human recombinant AChE by Paraoxon, as described in Example 5.
Figure 26:
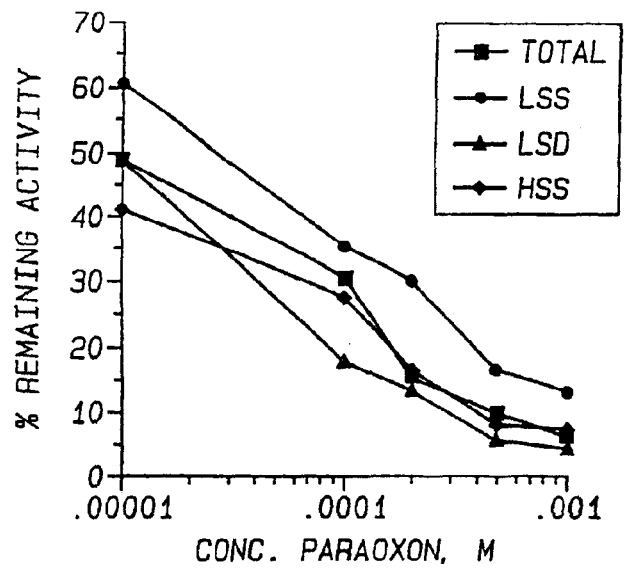
FIG. 26 shows graphically the in vivo inhibition of Xenopus AChE by Paraoxon, which inhibition affects all subcellular fractions of the enzyme, as described in Example 5.

The use of transgenic *Xenopus* embryos to assay for the toxicity of the anti-cholinesterase organophosphate poison, Paraoxon, is shown in FIGS. 25 and 26. In FIG. 25 there is shown the in vivo inhibition of human recombinant AChE by Paraoxon. Using the procedures described in Example 2 above, fertilized eggs of *Xenopus* were microinjected with 1 ng CMAChE DNA (see FIGS. 7A and B) and cultured for 2 days at 17–21° C. Groups of 4 embryos were incubated for 30 minutes with various concentrations of Paraoxon, washed, homogenized in a high salt/detergent buffer, and assayed for residual AChE activity (Upper left, in vivo). Uninjected, control embryos were similarly treated (Upper right, in vivo). For comparison, homogenates from day 1 AChE-injected or day 10 uninjected control embryos were similarly incubated with inhibitor and assayed for remaining activity (in vitro). Note the 5–10 fold decrease in sensitivity observed for both enzymes under in vivo conditions and the 100 fold higher sensitivity of human AChE to Paraoxon than that observed with embryonic *Xenopus* AChE (lower).

In FIG. 26 there is shown the in vivo inhibition of *Xenopus* AChE by Paraoxon, which inhibition affects all subcellular fractions of the enzyme. 2 day old "tailbud" embryos were exposed to increasing concentrations of the organophosphorous cholinesterase inhibitor paraoxon for 30 minutes, allowed 1.5 hours recovery, then frozen. Sequential extractions with low salt (20 mM Tris-HCl (pH 7.5), 10 mM MgCl$_2$, 50 mM NaCl), low salt/detergent (10 mM phosphate buffer (pH 7.4), 1% Triton X-100), and high salt (10 mM phosphate buffer (pH 7.4), 1 mM NaCl, 1 mM EGTA) buffers demonstrated that AChE activity in the soluble (LSS), membrane-associated (LSD), and extracellular matrix associated (HSS) fractions were equally inhibited during exposure. Each point represents one group of 3 embryos. T-total AChE activity.

Thus, from FIGS. 25 and 26 it is apparent that recombinant human AChE as expressed in *Xenopus* tadpoles represents a viable model for the in vivo testing of AChE inhibitors, including both ligand-binding and inhibitor penetration properties.

Recently, the present inventors have also studied the molecular basis underlying the anti-cholinesterase activity (toxicity) of carbamate substances. (see Loewenstein et al., 1993). In these studies comparative inhibition profiles were obtained for carbofuran and five other N-methyl carbamates, mostly carbofuran derivatives differing in length and branching of their hydrocarbonic chains, against human erythrocyte AChE (H.AChE), human serum BChE (H.BChE) in its normal form or in a mutant form containing the point mutation Asp70→Gly, and *Drosophila* nervous system ChE. The results indicated that carbofuran was most toxic to all the ChEs and that the *Drosophila* ChE was most sensitive to all the carbamates tested. Accordingly, such carbamates are good pesticides as they can be used at doses which are lethal to insects while, at the same time, cause little human ChE inhibition. Of the human ChEs, the AChE was more sensitive than the BChE to the carbamates, the BChE also having a lower flexibility towards changes in the carbamate side chain, i.e. the binding site for carbamates on BChE is less flexible than that of AChE towards changes in the carbamate side chain structure. Further, the above Asp70→Gly mutation had no effect on BChE inhibition by carbamates indicating that the Asp70 is not important in the active site for carbamate binding. Further, the results also indicated that the BChE has biological activities in mammals other than the simple scavenging activity attributed to this enzyme up to now. While the above anti-cholinesterase activity of carbamates on various ChEs was analyzed in vitro, it is clear that, on the basis of the description in Examples 1–4 above, the same analysis may be carried out in transgenic animals such as the transgenic *Xenopus* and mice. In this situation, the relevant ChE constructs (i.e. the above described AChE constructs as well as BChE and *Drosophila* ChE or other insect ChEs) may be introduced into the animals to obtain transgenic animals expressing such ChEs. These transgenic animals may then be used to analyze in vivo the effects of carbamates and other substances (e.g. organophosphates).

Furthermore, with respect to human BChE and AChE, a large number of naturally occurring (i.e. in human populations) variants of these enzymes are known: Ten variant alleles of BChE reflect amino acid substitutions that alter catalytic activity. Another 12 point mutations, insertions or deletions result in absence of enzyme activity in serum, or even of the protein itself (summarized in Soreq and Zakut, 1993). The prominent above noted D70G mutation of BChE (GAT to GGT) was first recognized as the cause of "atypical" apnea following administration of succinylcholine during anaesthesia. It is present with an allele frequency under 5% of the population of Europe and a far higher incidence in the Middle East. "Atypical" BChE does not hydrolyze succinylcholine and does not interact with various substrate analogs and inhibitors, which accounts for its resistance to natural alkaloid poisons prevalent in the Middle East and raised the possibility that it therefore confers a selective advantage. Other BChE mutations were associated with known BChE phenotypes, among them the common K variant substitution of alanine 539 by threonine (A539T, GCA to ACA), and the J variant substitution of glutamate 497 by valine (E497V, GAA to GTA), found, so far, in a single pedigree. Both these variants cause reduced activity of the serum enzyme, and a corresponding increase in sensitivity to succinylcholine during anaesthesia. In individuals residing in the United States (Americans) the A539T variant was reported to be closely linked to the G70 ("atypical") mutation, and the E497V variant was reported to have emerged on an allele carrying the A539T K variant. A dA replacement by dG, less-tightly linked to the above-mentioned mutations, was also reported at nucleotide position 2073 in the non-coding region of BChEcDNA.

The substitution of histidine 322 in erythrocyte AChE by asparagine (H322N, CAC to AAC) was first recognized as the basis of the Yt blood group system and has no known phenotype except as this serological marker (Soreq and Zakut, 1993). The rare allele has a frequency of about 5% in Europe but is much more abundant (10 to 20%) in Middle East populations. More recently, additional phenotypically innocuous mutations of AChE have been reported (Bartels et al., 1993): a change in the codon for proline 446 (P446, CCC to CCT), found in Americans in 100% linkage to the N322 mutation, and a substitution of proline 561 by arginine (P561R, CCG to CGG), unlinked to the former two, in the precursor polypeptide of hydrophobic AChE.

Example 6

Additional Protocols and Methods

Water Maze Test:

General Design. The procedures were modified from Morris (1989). The mice were tested in a square Plexiglas swimming pool, 61×61×30.5 cm, with an 11 cm high water level. The water contained 1.5 g/l powder milk and its temperature was 25° C. A hidden platform of 10×10 cm was in one quadrant of the pool, at 1 cm below the water level. At the beginning of a testing session, the mouse was placed in the water in a randomly chosen corner of the pool and the time necessary to climb to the platform was measured with a stopwatch. If the mouse didn't find the platform after 2 minutes, it was taken out of the water and put back after 30 seconds. The mice were tested 4 times each day at 30 seconds intervals.

Figure 27:
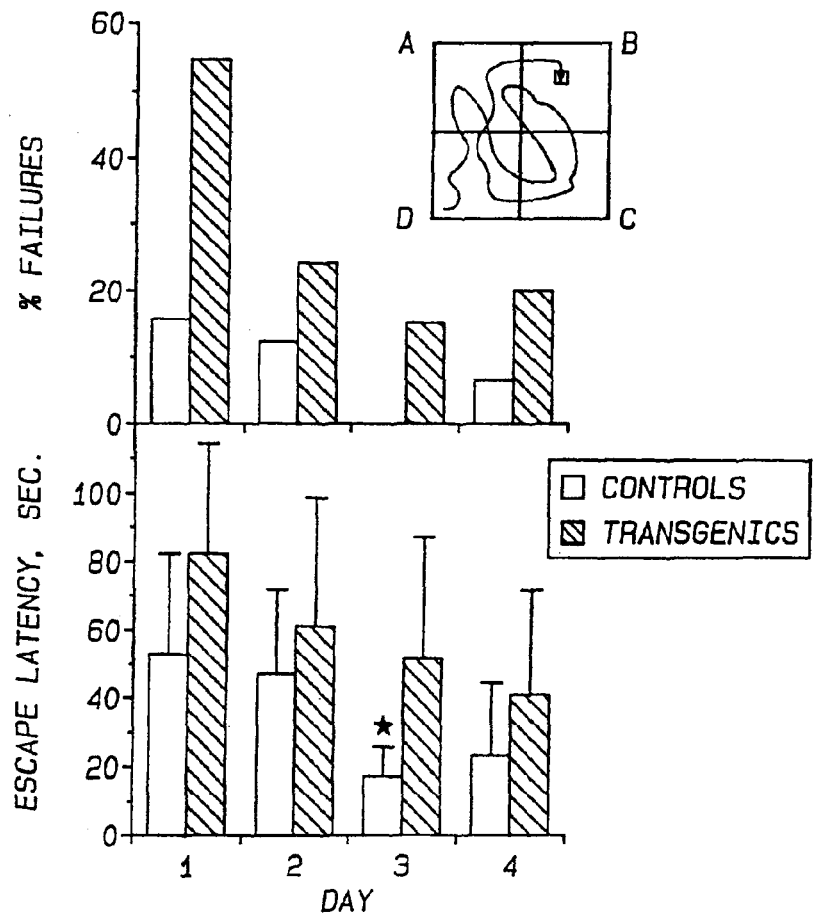
FIG. 27 shows graphically the results of the water maze test as used in Example 6.

Water Maze Protocol for initial experiments (FIG. 27). Experiment 1 was designed to train the mice and to see their general behavior. The hidden platform was fixed in one quadrant. Four sessions were repeated each day during four days (day 1 to 4). In Experiment 2, the platform was removed on day 6 after the beginning of the experiment, to see if the mice remembered its location. The time spent in each quadrant was noted in 5 sec intervals during one minute. In Experiment 3, on day 8, the platform was located in an other quadrant. The mice were first put 10 seconds on the platform, to know its position, and then removed. After 30 seconds, the mice were tested as in the first experiment. The same experiment was repeated on day 9, with a new position of the platform and with IP injection of 200 ml of 10 mg/kg tacrine in PBS or PBS alone in two equal groups.

Effect of tacrine on the learning and memory steps. The design of the experiment was as follows: mice were injected IP with 200 ml of 20 mg/kg tacrine in PBS or PBS alone. 30–60 min after injection, they were tested in the water maze as in experiment 1, with the only difference that at beginning they were first put 10 seconds on the platform, to know its position. On day two, they were injected and tested as in day 1, with the same platform localization. The design of this experiment was similar to Experiment 3, with the difference that the mice were naive to the water maze, and were injected with tacrine or PBS.

Results

To examine cholinergic functions in these transgenic mice, applicants first measured their hypothermic responses to the anti-AChE organophosphate diisopropylfluorophosphate (DFP). Relative, dose-dependent resistance to DFP-induced hypothermia was observed in the transgenic as compared with control mice. The transgenic mice were almost totally resistant to a low DFP dose (0.25 mg/kg) and displayed normal physical activity levels, shorter duration of response and limited reduction in body temperature with higher doses, while controls suffered severe cholinergic syndrome.

Moreover, the transgenic mice displayed relative resistance to the hypothermic effect of the muscarinic agonist oxotremorine, to the less potent effect of nicotine, and to the serotonergic agonist 8-OH-DPAT as compared to controls. This indicates that changes occurred in additional key proteins within their cholinergic synapses and that the action of serotonergic synapses involved in thermoregulation is influenced by the induced changes.

Applicants also examined the capacity of the transgenic mice to adapt to cholinergic insults. When repeatedly injected with 0.25 mg/kg DFP, both transgenic and control mice acquired cross-tolerance to oxotremorine-induced hypothermia, demonstrating unimpaired plasticity of their cholinergic functioning. Yet, no difference was detected between transgenic and control mice in response to the (×2-adrenergic agonist clonidine, indicating that the noradrenergic synapses involved in thermoregulation are not subject to control by cholinergic elements and that these changes did not reflect general impairment in the control over body temperature. Also, the thermic response to cold exposure was similar in the transgenic and control mice.

Electron microscopy analysis of cytochemical staining revealed more conspicuous depositions of the electron dense reaction product of ACHE within dendrites in the thermoregulatory anterior hypothalamus of transgenic as compared with control brain sections, attributing the changes in thermoregulatory responses to ACHE overexpression. However, length of synapses interacting with these stained dendrites was indistinguishable in the transgenic mice as compared with controls. Thus, these mammalian brain synapses were more resistant to the modulation of key elements conferred by overexpressed human ACHE than neuromuscular junctions in *Xenopus* tadpoles, the length of which increased when hAChE was overexpressed in them (Seidman et al., 1994).

The hippocampal overexpression of the ACHE transgene predicted involvement in learning and memory. To explore this issue, applicants employed the hidden platform test of the Morris water maze (Morris, 1989). In this test, transgenic and matched control mice are trained to escape a swimming task by learning the position of a hidden platform and climbing on it. The time it takes them to complete this task is defined as the escape latency. Applicants determined for each animal the percentage of failures to find the hidden platform within 2 minutes (FIG. 27, top). Transgenic animals failed far more frequently than controls throughout the 4 days experiment. This was particularly conspicuous in day 1, with 54% failures for the transgenics as compared with 16% failures for the controls. Even after 3–4 days training, transgenic stayed at a plateau of 20% of failures, whereas control failures were reduced to 5% or less.

In parallel, the escape latency (taking a failure as 120 sec., e.g. the duration of a session) was longer for transgenic mice as compared with corresponding controls throughout the 4 days experiment and 16 training sessions. Whereas control mice shortened their initial escape latency of 53 sec. down to a plateau of 23 sec. by day 3, transgenics slowly improved from 82 to 42 sec. in 4 days (FIG. 27, bottom). Both the extent of shortening in the escape latencies and the ratio between learning rates in the transgenics and controls were similar to the parallel parameters reported for α-calcium calmodulin kinase II mutant mice, with the exception that the transgenic strain of the present invention seemed to display slower performances than the one used by these authors.

The impairment of spatial learning and memory in hAChE-overexpressing mice displays a reciprocal paradigm to the use of anti-AChE drugs to improve cognitive functioning in Alzheimer's patients (Knapp et al, 1994). The responses of the transgenic mice to light and sound stimuli, in open field and T-maze tests should reveal whether they also suffer from other behavioral deficits. Moreover, it will be intriguing to retest the cognitive functioning of these mice when aged. Thus, the established line of AChE-overexpressing mice provides a long-needed model system for cholinergic deficits in mammals. It is most suitable for testing the correlation between cholinergic circuits and long term potentiation (LTP). Differential display studies can be employed to detect transcriptional changes in the relevant brain regions before and after treatment with selected drugs. The HpACHE transgenic model can also serve to explore the yet unknown mechanistic details of thermoregulation in mammals (Clement, 1991). In addition, the transgenic mice are expected to possess neuromuscular junctions with abnormal levels of presynaptic, but not post-synaptic AChE, an interesting correlation amyotrophic lateral sclerosis. The HPACHE transgenic mice thus provide a useful mammalian model for behavioral, physical and molecular studies of CNS cholinergic functions.

Example 7

Additional Protocols and Methods

Figure 28:
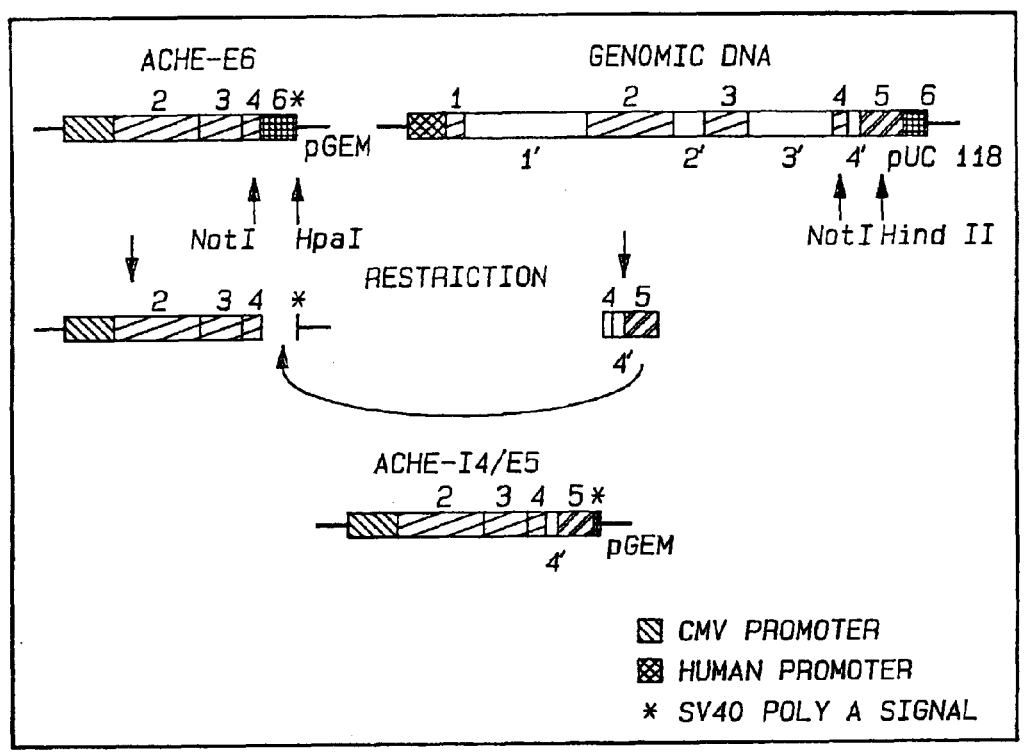
FIG. 28 shows the DNA constructs used in Example 7.

Vectors. The plasmid referred to as ACHE-E6 and employed to express the major brain and muscle form of AChE has been described in detail as CMVACHE (Velan et al., 1991 and Example 2 and FIG. 28). This plasmid contains the AChE-coding exons E2, E3, E4 and E6 (Soreq et al., 1990) downstream of the CMV promoter and followed by the SV40 polyadenylation site. ACHE-E6 was used to construct ACHE-I4/E5 by exchanging the cDNA restriction fragment NotI-HpaI with the genomic fragment NotI-HindII. ACHE-I4/E5 potentially encodes both the GPI-linked erythrocyte AChE form generated by splicing of I4, and/or the readthrough AChE form (Karpel et al., 1994).

Xenopus embryo microinjections. In vitro fertilization and microinjection of mature Xenopus eggs were performed as described hereinabove except that embryos were raised at 19–21° C.

RT-PCR Procedure and Primers. Total RNA was extracted from Xenopus embryos 1 day after injection by the RNASO1-B™ method (CINNA/BIOTECX), according to the protocol supplied by the manufacturer, and was treated with DNase (Promega) as previously described (Ben Aziz-Aloya et al., 1993). RT-PCR analyses were as detailed by Karpel et al (1994) using a Perkin-Elmer/Cetus thermal controller. Amplification was for 1 minute, 94° C., first cycle 3 minutes; 1 minute, 65° C.; 1 minute, 72° C., last cycle for 6 minutes, performed with the following primer pairs:

(1) E3/1522+ (SEQ ID No:13) and E6/2003– (SEQ ID No:14);

(2) E3/1522+ (SEQ ID No:13) and E5/1917– (SEQ ID No:16);

(3) E3/1522+ (SEQ ID No:13) and I4/1939– (SEQ ID No:15);

(4) E3/1522+ (SEQ ID No:13) and E4/1797– (SEQ ID No:28).

according to their position in the human ACHE alternative coding sequences (Soreq et al., 1990 and Karpel et al., 1994) and noted as upstream (+) or downstream (–) according to their orientation. Amplification products (20%) were electrophoresed on a 2% agarose gel and UV-photographed (320 nm).

Reverse transcription and PCR were performed on total RNA from 1-day-old Xenopus embryos injected with the ACHE-E6 (E6) or ACHE-I4/E5 (I4/E5) DNA constructs. Uninjected embryos (U) served as control. PCR products were electrophoresed as previously described (Ben Aziz-Zloya et al., 1993) and their lengths evaluated by markers (M) of known size. DNA-PCR analysis performed with the ACHE-I4/E5 DNA construct (I4/E5 DNA) confirmed the ability of primer pair number 2 to yield a PCR product. Control reactions, without reverse transcriptase, did not yield amplification products, proving the absence of contaminating DNA sequences.

AChE activity assays and subcellular fractionations. AChE activities were determined using a standard colorimetric assay adapted to a 96-well microtiter plate (Soreq et al., 1990; Seidman et al., 1994). Assays were performed in 0.1M phosphate buffer (pH 7.4), 0.5 mM dithio-bis-nitrobenzoic acid and 1 mM acetylthiocholine substrate at room temperature. $OD_{405}$ was monitored for 20 minutes at 3–5 minute intervals.

Subcellular fractionation of one-day-old embryos into low salt (0.01M Tris-HCl (pH 7.4), 0.05M $MgCl_2$, 144 mM. NaCl), low salt/detergent (1% Triton x-100 in 0.01M Na phosphate (pH 7.4)), and high salt (1M NaCl in 0.01M Na phosphate (pH 7.4)) buffers was performed as described by Seidman et al. (1994).

Non denaturing gel electrophoresis. Electrophoresis was performed in 6% polyacrylamide gels according to a standard protocol for SDS-PAGE (Sambrook et al., 1992) except that SDS was omitted from all solutions. Wherever noted 0.5% Triton X-100 was included. Gels were run in the cold for 2–4 hours, rinsed 2–3 times with double distilled water, and stained several hours to overnight for catalytically active AChE using the thiocholine method for histochemical staining of AChE developed by Karnovsky and Roots (1964), and in Example 2 and as detailed herein below.

Whole mount cytochemical staining. Two-day-old Xenopus embryos were fixed for 20 minutes in 4% paraformaldehyde (in 0.6×PBS), rinsed 3 times with PBS, and transferred to a clean glass vial. Fixed embryos were incubated in staining solution (0.67 mM acetylthiocholine, 5 mM sodium citrate, 3 mM cupric sulfate, 0.5 mM potassium ferricyanide in 0.1M acetate buffer (pH 5.9)) overnight at room temperature with gentle rotation, rinsed several times with PBS, and post-fixed with 2.5% glutaraldehyde for 1 hour. Embryos were then dehydrated by successive transfers through 30–50–70–100% methanol, mounted in Murray's clearing solution (benzyl alcohol:benzyl benzoate 1:2) and viewed under low magnification with a Zeiss stereomicroscope. Clearing permitted visualization of internal structures and improved with time up to 18–24 hours.

Electron microscopy and morphometric analyses. Histochemical staining and transmission electron microscopy was performed as previously described by Ben Aziz-Aloya et al (1993). Morphometric analyses of NMJs from two-day old embryos raised at 21° C. were performed using the SigmaScan software (Jandel Co., Berkeley, Calif.), and an IBM-compatible P.C.

Results

Alternative mRNAs Dictate Specific Accumulation of AChE in Muscle or Epidermis

To examine the ability of alternative splicing to account for tissue-specific accretion of AChE, in vitro fertilized *Xenopus* eggs were microinjected with 1 ng ACHE-E6 or ACHE-I4/E5 DNA. The resultant embryos were raised for 2–3 days, fixed, and stained for catalytically active enzyme. Following injection of ACHE-E6, encoding the brain and muscle form of AChE, 2-day-old tailbud embryos displayed conspicuous overexpression of AChE in the developing myotomes. Myotomal overexpression was primarily observed as pronounced longitudinal staining along the plane of the muscle fibers between the vertical bands representing natural intersomitic accumulations of AChE. No other tissues displayed consistently or prominently enhanced staining. However, myotomal overexpression of AChE was clearly mosaic, varying in intensity within and between individual somites. Uninjected control embryos displayed the characteristic transverse staining along the junctions between somites, but only faint staining within the myotomes.

In contrast to the striking accumulation of ACHE-E6-derived AChE in myotomes, applicants did not observe any discernible enhancement of staining in myotomes of embryos injected with ACHE-I4/E5. Rather, applicants noted pronounced punctuated staining of the epidermis which was never seen in uninjected embryos. Epidermal staining could be observed over the entire body along both the rostral-caudal and dorsal-ventral axes. Inter-somitic staining was unaffected by overexpression of ACHE-I4/E5. Although limited epidermal staining was occasionally observed in ACHE-E6-injected embryos, this phenomenon appeared restricted to sites of particularly high myotomal expression and was considerably less well defined. These observations indicated that AChE derived from ACHE-E6 DNA was specifically accumulated in muscle, whereas AChE derived from ACHE-I4/E5 was uniquely targeted to the epidermis.

A Novel Truncated Readthrough ACHEmRNA Species

Microinjected *Xenopus* embryos have been shown to correctly splice intron I1 from a human ACHE promoter-reporter construct to produce catalytically active AChE (Example 2). ACHE-I4/E5 potentially encodes both the mRNA encoding the erythrocyte GPI-linked AChE by splicing out of intron I4, and/or the complete readthrough mRNA in which the invariant exons continue directly from exon E4 into intron I4 and through it into exon E5 (Karpel et al., 1994). To determine which ACHEmRNA(s) were produced in *Xenopus* embryos of the present invention, applicants subjected total RNA extracted from one-day-old ACHE-E6 or ACHE-I4/E5 injected embryos to reverse transcription followed by PCR (RT-PCR) with E4-, I4-, E5- or E6-specific primers. When an E6-specific primer pair was employed to analyze RNA from ACHE-E6-injected gastrulae the expected 491 bp fragment representing full-length ACHE-E6-mRNA was reproducibly observed. When RNA from ACHE-I4/E5-injected embryos was subjected to RT-PCR, both the invariant exon E4 and the intronic sequence I4 were detected. However, the E5-specific primer pair repeatedly failed to generate either the 476 bp fragment representing the full-length readthrough mRNA or the 398 bp fragment representing spliced E5-bearing mRNA.

A parallel reaction using control plasmid DNA and the identical E-5-specific primers did yield the 476 bp band, however, validating the efficacy of this primer pair. Moreover, this same primer pair has been successfully utilized to detect native E5-carrying. mRNAs in human tissues and transfected mammalian cells (Karpel et al., 1994 and unpublished data). These data therefore indicated that the recombinant human AChE activity induced by ACHE-E6 reflected the complete brain and muscle AChE, whereas heterologous AChE activity produced in *Xenopus* from ACHE-I4/E5 was derived from a truncated readthrough ACHEmRNA. This, in turn, implied that the polypeptide encoded by ACHE-I4/E5-derived mRNA in *Xenopus* should display biochemical characteristics distinct from both brain/muscle and erythrocyte AChEs.

Unique Properties of ACHE-I4/E5-derived AChE

Microinjection of 1 ng ACHE-E6 DNA induces transiently high levels of catalytically active recombinant human AChE in *Xenopus* embryos (Seidman et al., 1994). When ACHE-I4/E5 was introduced into 1–2 cell cleaving embryos, similar levels and a similarly transient patter of heterologous overexpression were observed, peaking at days 1–2 post-fertilization and receding to day 4 or 5. Data represent average of 3 separate groups of 4 embryos from a single microinjection experiment. Overall development of injected embryos appeared normal through gastrulation, neurulation, hatching and the acquisition of motor function. Although control mock injections indicated that microinjection may slightly retard growth and the accumulation of endogenous AChE, quantitative RNA-PCR performed with primers specific for XmyoD and *Xenopus* GATA-2 (Zon et al., 1991) indicated that no global changes occurred in the levels of endogenous DNAs encoding these myogenesis- and hematopoiesis-promoting proteins in ACHEDNA-injected embryos.

To compare the hydrodynamic properties of the recombinant human enzymes, applicant performed sequential extractions of gastrula-stage embryos into low-salt, low-salt/detergent, and high-salt buffers. AChE activity from embryos injected with ACHE-E6 DNA consistently partitioned into both the low-salt (55%) and low-salt/detergent fractions (35%). In contrast, activity from embryos injected with ACHE-I4/E5 was 85–90% solubilized in the low-salt step. In sucrose density gradient centrifugation, a single peak between 3–4S was observed for both the ACHE-E6 and ACHE-I4/E5 derived enzymes, consistent with a monomeric configuration for the cell-associated recombinant molecules. However, in non-denaturing polyacrylamide gel electrophoresis, catalytically active AChE from ACHE-I4/E5-injected embryos migrated as a triplet band which ran significantly faster than the single band representing either recombinant human AChE from ACHE-E6-injected embryos or native AChE from human brain or erythrocytes. When electrophoresis was performed in the absence of detergent, no significant shift in the migration of ACHE-I4/Eb-derived bands was observed, suggesting that this molecule represented a non-hydrophobic AChE species.

E6 but not I4/E5 Terminal Peptide Directs NMJ Localization of Recombinant Human AChE Electron microscope analysis of myotomes stained for catalytically active AChE revealed conspicuous overexpression of enzyme in NMJs of ACHE-E6-injected embryos and correlated overexpression with alterations in synaptic ultrastructure (Seidman et al., 1994). To examine the potential for ACHE-I4/E5-derived AChE to be similarly localized, applicants performed morphometric analyses of cross-sections from a series of stained NMJs from DNA-injected or control uninjected embryos. The average AChE-stained cross-sectional area of NMJs from ACHE-E6-injected embryos reached 3 or 4 times that observed in NMJs from uninjected embryos (0.33±0.29 $\mu m^2$ vs 0.08±0.09 $\mu m^2$). However, the average stained area of NMJs from embryos injected with ACHE-I4/E5 (0.14±0.03 $\mu m^2$) displayed only a minor increase compared with controls. Transverse sections of myofibers displayed a parallel pattern of highly intensified staining in myotomes of ACHE-E6 injected embryos compared with both ACHE-I4/E5-injected and uninjected controls. A 2-fold increase in mean post-synaptic membrane length was associated with ACHE-E6-mediated overexpression compared with controls (3.8±2.1 $\mu m$ vs. 2.2±1.3 $\mu m$). In contrast, the average post-synaptic length observed in ACHE-I4/E5 embryos (1.9±0.2 $\mu m$) was approximately the same as controls.

At least 40% of NMJs from uninjected and ACHE-I4/E5 embryos displayed post-synaptic lengths less than 3 $\mu m$. In contrast, these small synapses were not observed in ACHE-E6-injected embryos. Rather, a class of large NMJs (>4 $\mu m$) rarely observed in control or ACHE-I4/E5-injected embryos dominated in those transgenic for ACHE E6. When the AChE-stained area was calculated as a function of post-synaptic length, ACHE-I4/E5-injected and control uninjected embryos displayed a similar, constant relationship between these parameters, whereas ACHE-E6-injected embryos displayed a higher ratio for all length categories. Thus, there appeared to be a correlation between AChE overexpression and enhanced post-synaptic length in individual synapses. Together, these observations imply a role for the E6-derived peptide in localizing AChE to NMJs, and demonstrate that the effects of AChE overexpression on NMJ biogenesis are dependent on the synaptic localization of the enzyme.

I4/E5 Directs Accumulation of AChE in Epidermal Cells and its Excretion

To study the cellular and sub cellular distribution of overexpressed AChE in epidermis cells from embryos injected with ACHE-I4/E5, applicants examined cytochemically stained embryos by electron microscopy. Two types of epidermal cells (Billett and Gould, 1971) were labelled by the electron dense crystals of AChE reaction product: ciliated epidermal cells derived from the inner, sensorial, epidermal layer and mucous-discharging secretory cells. There were many fewer ciliated cells than secretory cells. Yet, the frequency and intensity of staining was higher among the ciliated cells with some displaying massive apical accumulations of reaction product. This irregular mosaic of heavily stained cells corresponded well to the punctuated array of stained cells observed in whole mount embryos. In uninjected control and ACHE-E6-injected embryos, both types of epidermal cells displayed scant staining, if any.

Ciliated cells were characterized, in addition to their cilia, by their dense cytoplasm, rich accumulation of mitochondria, and by the presence of numerous small vesicles, most of which were filled with reaction product in stained cells. Crystals of reaction product were also observed, however, in the cytoplasm, increasing in size and density in a graded fashion toward the apex. In contrast, secretory cells were identified on the basis of their large, distinctive, chondroitin-laden secretory vesicles (Nishikawa and Sasaki, 1993), some of which appeared to be fused to the plasma membrane. In labelled secretory cells from ACHE-I4/E5-injected embryos, up to 20% of the vesicles were stained positively for AChE. However, only an occasional crystal of reaction product could be observed in vesicles from uninjected or ACHE-E-6-injected embryos. No gross morphological features distinguished stained cells or vesicles in ACHE-I4/E5-injected embryos from unstained ones or from those observed in control or ACHE-E6-injected embryos.

The observation that mature secretory vesicles in epidermis of ACHE-I4/E5-injected embryos stained positively for AChE suggested that this enzyme form may be secreted along with the mucous naturally contained within these vesicles. To determine whether AChE was being excreted from the body, healthy neurula-stage embryos injected with either vector or uninjected, were incubated overnight and the AChE activity found in the medium was compared with that measured in total homogenates. Only incubation medium from embryos injected with ACHE-I4/E5 DNA displayed significant AChE activity, representing up to 40% of the total measured activity. Together, these observations indicate that some property or properties intrinsic to the short I4/E5 terminal peptide confer a signal for epidermal accumulation, polarized subcellular transport and excretion of AChE.

Discussion

The native human ACHE promoter includes consensus recognition sites for transcription factors indicative of tissue-specific regulation of transcription (Ben Aziz-Aloya et al., 1993) However, the CMV promoter used to direct the expression of AChE in *Xenopus* is panactive (Schmidt et al., 1990) and is probably expressed in the embryos in a non-specific manner relatively early in development. This would explain the high levels of heterologous enzyme observed at the gastrula stage (day 1). Thus, the tissue-specific accumulation of alternative heterologous AChEs most likely reflects differential posttranscriptional management of their respective mRNAs or protein products. Stabilization of ACHEmRNA was recently shown to account for the increased AChE activity accompanying differentiation of cultured myoblast (Fuentes and Taylor, 1993).

In vivo, AChE is subject to tissue-specific and developmentally-regulated posttranslational processing which gives rise to a complex array of molecular forms varying in their extent of oligomeric assembly, association with non-catalytic subunits, hydrodynamic properties, and sites of subcellular localization (reviewed by Massoulie et al., 1993). One level at which this diversity is controlled appears to be alternative splicing of 3' exons (Sikorav et al., 1988; Li et al., 1991). Transfections of AChE-coding sequences into mammalian cells indicated that alternative splicing alone could account for these multiple molecular forms of AChE (Krejci et al., 1991; Duval et al., 1992; Legay et al., 1993b; Li et al., 1993). Applicants' results unexpectedly extend these conclusions by demonstrating that alternative splicing may dictate the final complement of specific AChE catalytic subunits available to particular cell types through selective management of specific AChE mRNAs or polypeptides.

Compartmentalized biosynthesis of the nicotinic acetylcholine receptor (Merlie and Sanec, 1985; Reviewed by Chanqeux, 1991) as well as other NMJ proteins (Pavlath et al., 1989; Ralston and Hall, 1989) suggests that an intricate network of factors are at work to produce and localize NMJ proteins around junctional regions prior to their active accumulation at the NMJ. Applicants hypothesized that this network could also potentially include cis-acting elements intrinsic to the mRNA or primary amino acid sequences of NMJ-targeted proteins, as well as trans-acting cellular components capable of anchoring or translocating these molecules within the muscle. An example for sequence-dependent translocation and anchoring of a specific mRNA is the developmentally regulated accumulation of Vg1 in *Xenopus* oocytes (Pressman-Schwartz et al., 1992). Recent work demonstrating the spatially restricted biosynthesis of AChE in avian muscle predicts the existence of localized cellular factors recognizing AChE and/or its encoding mRNA (Jasmin et al., 1993).

When DNA encoding the mouse readthrough mRNA, characterized by a nonsense codon 40 nucleotides downstream of the F4/I4 boundary, was expressed in COS cells, 97% of the total activity was soluble and secreted into the culture medium (Li et al., 1993). The current study suggests that a truncated human readthrough ACHEmRNA is also translatable, and that it gives rise to a catalytically active, non-muscle, secretory form of AChE in *Xenopus*. However, the overall timing and levels of ACHE-I4/E5 expression in the embryos as assessed in total homogenates indicates generally similar stability of its mRNA and protein product as compared to those derived from ACHE-E6. Therefore, these observations offer the first indications for the existence of yet another stable human AChE subtype representing the common exons E2, E3, E4 and the pseudo-intron I4.

The human readthrough AChEmRNA carries a 9-nucleotide sequence (5' ACCTGCCA 3') (Karpel et al., 1994) beginning 18 nucleotides downstream of the I4/E5 boundary that is identical (8 out of 9 bp) to that contained within a 19 bp consensus mRNA destabilizing site (Brown et al., 1993). This sequence mediates endonucleolytic cleavage of RNA in *Xenopus* and *Drosophila*, and could explain the appearance of the apparently truncated RNA. Alternatively, or in addition, the unusual properties exhibited by AChE derived from ACHE-I4/E5 in *Xenopus* could reflect posttranslational events such as proteolytic cleavage or incomplete processing of the E5 hydrophobic peptide. Indeed, when DNA encoding GPI-linked *Drosophila* AChE was expressed in microinjected *Xenopus* oocytes, a hydrophobic, but non-glypiated, membrane-associated was obtained. However, deletion of the sequence encoding the 27 amino acid hydrophobic C-terminal peptide yielded a soluble, secreted AChE (Fournier et al., 1992).

Example 8

Antisense prevention of neuronal damages following head injury.

Figure 29:
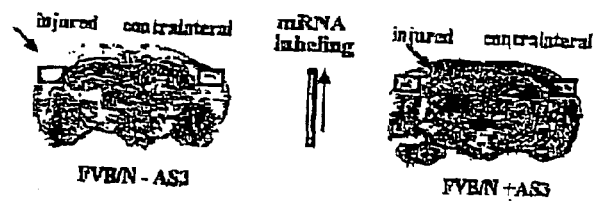
FIG. 29A shows that antisense oligonucleotides suppress the trauma-induced unilateral accumulation of readthrough AChE mRNA in mouse brain.
FIG. 29B is a pseudocolor representation of the red hybridization signal that was generated using ImagePro image analysis software.
Figure 29:

(a) Closed head injury (CHI). Adult FVB/N mice were subjected to closed head injury and injected one hour later with PBS (Shown on the left of FIGS. 29 A and B) or 2'-O-methyl protected antisense oligonucleotide targeted to AChE mRNA (AS3; Grisaru et al., MCB 19:788)(Shown on the left of FIGS. 29A and B) into the site of injury. The mice were sacrificed 14 days later. In situ hybridization was performed on five μm brain sections using a biotinylated 2'-O-methyl cRNA probe targeted to intron I4 in mouse AChE mRNA (Kaufer et al., Nature 393:373). Staining was done with Fast Red.

Pseudocolor representation of the red hybridization signal was generated using ImagePro image analysis software. Note the AChER mRNA is intensively expressed in the injured hemisphere following CHI, close to the site of injury (as shown by the arrows in FIG. 29A). A single treatment with AS3 suppressed AChER mRNA accumulation in both hemispheres. AChER mRNA was barely detectable in control injured mice.

FIG. 29B shows the representative confocal images of somatosensory cortical neurons from the boxed areas. Note the massive unilateral accumulation of AChER mRNA in somata and apical dendrites (shown by the white arrows in FIG. 29B). AS3 dramatically suppressed the neuronal accumulation of AChER mRNA with approximately equal efficiency in both subcellular compartments.

(b) Transgenic mice overexpressing the human "synaptic" AChE variant. These mice were subjected to closed head injury and injected with either AS3 or antisense oligonucleotide targeted to mRNA encoding the non-relevant, homologous butyrylcholinesterase (ASB) and analyzed as in FIG. 29A and B.

Figure 30:
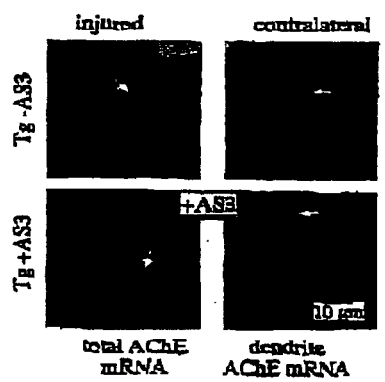
FIG. 30A shows that head trauma elicits exaggerated bilateral accumulation of endogenous readthrough AChE mRNA in AChE transgenic mice.
FIG. 30B shows graphically that head trauma elicits exaggerated bilateral accumulation of endogenous readthrough AChE mRNA in AChE transgenic mice.
Figure 30:
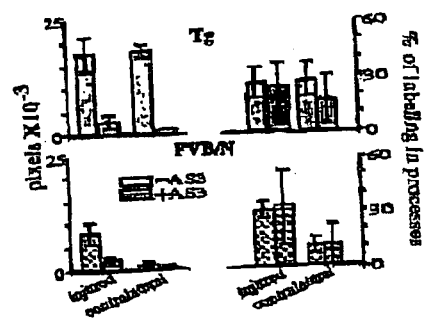

There was an intense hybridization signals in cortical neurons from both the injured and contralateral hemispheres of ASB-treated mice (FIG. 30A) and the effective suppression of AChER mRNA accumulation in neurons from AS3-treated mice (FIG. 30A).

Confocal densitometric analysis was performed on cortical neurons as depicted in FIGS. 29B and 30A. Columns represent the total number of pixels or the percent of total pixels detected within dendrites (FIG. 30B) for the injured and contralateral hemispheres of AChE transgenic (Tg) or control FVB/N mice injected with or without antisense oligonucleotides against AChE mRNA (±AS3) one hour post-injury. Analysis was performed two weeks following treatment. There were dramatically elevated levels of total AChER mRNA in neurons from both the injured and contralateral hemispheres of transgenic as compared to FVB/N mice, and the four to six-fold reduced levels in animals treated with AS3.

Figure 31:
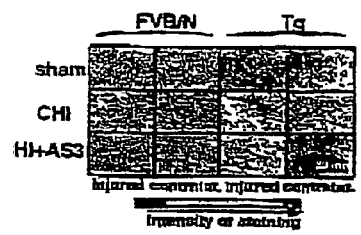
FIGS. 31A and B show that antisense treatment suppresses dendritic growth and promotes neuron survival following head trauma; (A) shows pseudocolor representations of cortical sections in which Golgi stained neurites appear red and; (B) is a graph showing the percent CA3 live neurons.
Figure 31:
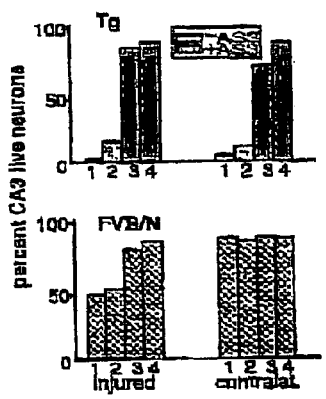
Figure 32:
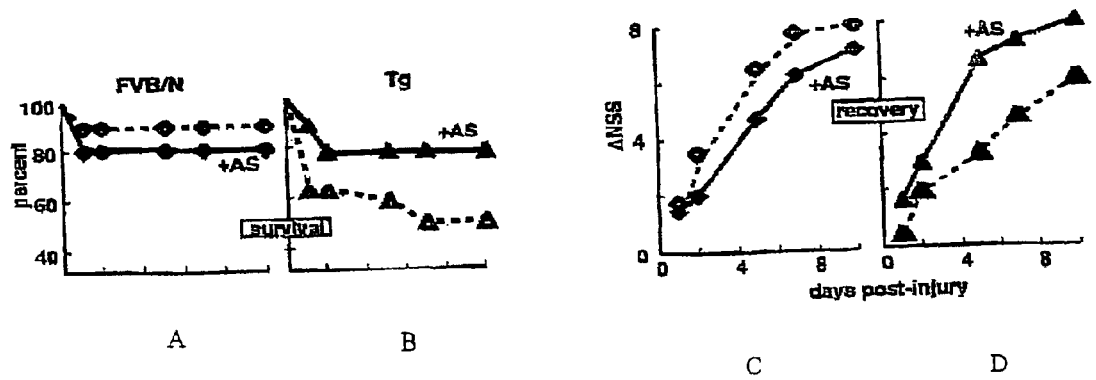
FIGS. 32A–D show that antisense treatment rescues survival and neurological recovery of AChE transgenic mice; (A) shows the percent of FVB/N; (B) shows the percent of Tg; (C) shows the ANSS of FVB/N recovered; and (D) shows the ANSS of Tg recovered.

(c) Antisense treatment suppresses dendritic growth. Golgi staining of dendrites was performed on brain sections from uninjured (sham) FVB/N or AChE transgenic (Tg) mice or from mice subjected to closed head injury untreated (CHI) or treated with a single injection of 50 ng of an antisense oligonucleotide targeted to AChE mRNA (CHI/AS3). FIG. 31A shows the pseudocolor representations of cortical sections in which Golgi stained neurites appear red. There was an intense Golgi staining representing a high density of dendrites in cortex from the injured hemisphere of both FVB/N and transgenic mice 14 days post-injury/Golgi staining was significantly reduced in mice treated with AS3.

Live and dead neurons in the hippocampal region CA3 were counted in two consecutive sections from four control and four transgenic mice 14 days following closed head injury with or without antisense treatment. Overt neuronal cell death was identified by the presence of pyknotic black cell bodies. 150–200 cells were counted for each mouse at ×400 magnification. Sections with 100% neuron loss were considered to reflect massive necrosis and were not included in the analysis. The columns of FIG. 31B represent the percent of live neurons counted for individual mice. There was dramatic bilateral neuron loss suffered by transgenic as compared with FVB/N mice and the minimal neuron loss observed among antisense treated animals.

(d) Antisense treatment rescues survival and neurological recovery of AChE transgenic mice. Control FVB/N and AChE transgenic mice were subjected to closed head injury and monitored for survival and neurological recovery. One hour following trauma, a neurological severity score (NSS) was assigned using a battery of 25 tests which included reflexive responses, motility, and grasping and balancing tasks of graded difficulty (Chen et al., J. Neurotrauma 13:557). The difference between NSS at various time points post-trauma and that at one hour was defined as ΔNSS (Increasing ΔNSS indicated improved performance and served as an indicator of recovery). Presented in FIGS. 32A–D are percentages of injured mice alive (A and B) and average ΔNSS for surviving mice (C and D) at the noted days following trauma. There was retarded recovery of neurological functions among AChE transgenic mice throughout the ten day recovery period compared to controls and its reversal to control levels following a single AS3 treatment. The starting N=20 for all mice.

(e) Conclusion. These findings demonstrate the potential of antisense therapeutics in treating acute traumatic injury and suggest antisense prevention of AChER overproduction for limiting the detrimental consequences of various traumatic insults to the nervous system.

Example 9

Transgenic human AChE variants display different capacities of inducing "corkscrew-like" neuronal processes in mouse somatosensory cortex.

Cognitive deficits in transgenic mice overexpressing human synaptic AChE-E6 variant and evidence of differential effects of AChE variants on neurite growth in vitro led to the study of immunodetection of neurofilament 200 (NF200), a marker of neuronal processes. The study revealed a "corkscrew" pattern, denoting a curving line with sinusoidal regularity in the somatosensory cortex. The cumulative lengths of corkscrew neural processes in an area of 0.48 mm$^2$ were 3000, 2950, 1350 and 500 $\mu$m in brains of AChE-E6, and InAChE-E6 variants, I4-AChE or control FVB/N mice, respectively.

The corkscrew phenotype is induced in degenerating cortical pyramidal cells after administration of phencyclidine (PCP), an N-methyl-D-aspartate (NMDA) receptor blocker. PCP blocks NMDA receptors on cortical GABAergic interneurons, relieving their inhibitory input to cortical pyramidal cells thus exposing pyramidal cells to excessive cholinergic excitation.

To test whether the corkscrew phenotype in AChE transgenic mice reflected loss or damage to GABAergic cells, Calbindin D28K and Parvalbumin were immunostained. GABAergic cell counts and morphological characteristics revealed no differences in the somatosensory cortex between the above mouse lines and controls, which attributed the observed neuropathology to the transgenic enzyme. However, catalytically active and inactive AChE both induced this pathology with similar efficacy, whereas the extrasynaptic I4-AChE variant was far less effective. These findings demonstrate induction of intriguing neuropathological changes mediated by the non-catalytic properties of AChE and affected by its variable C-terminus.

Example 10

Recent studies demonstrate the scavenging capacity of the acetylcholine hydrolzing enzymes acetylcholinesterase (AChE) and butyrylcholinesterase (BuChE) against organophosphate intoxication in primates and rodents (Wolfe et al., 1992; Maxwell et al., 1993; and Raveh et al., 1997).

To investigate the possibility of producing transgenic human AChE in mammalian milk, mammary gland expression of cholinesterases were studied in two lines of transgenic mice overexpressing the human (h) non-synaptic 3'-alternatively spliced "readthrough" AChE mRNA transcript including the I4 pseudointron and the 3' terminal exon E5, (h AChE-I4/E5) directed by the cytomegalovirus (CMV) efficient promoter. Two additional lines expressed catalytically active (Beeri et al., 1995, 1997) or insert-inactivated AChE terminated with the brain characteristic C-terminus translated from exon 6 (hAChE-E6 and hInAChE-E6, Sternfeld et al., 1998). Non transgenic FVB/N mice served as controls. In mammary gland alveoli of hAChE-I4/E5 transgenic mice, in situ hybridization demonstrated pronounced labeling of hAChE-I4/E5 mRNA transcripts, considerably higher than the endogenous mouse (m) AChE-I4/E5 mRNA transcripts detected in both wild typs FVB/N mice and the hAChE-E6 transgenic mice.

The capacity of milk cholinesterases to hydrolyse acetylthiocholine (ATCh) was tested in the absence or presence of the BuChE-specific inhibitor iso OMPA throughout the first two weeks after delivery. Transgenic mice expressing 44-fold higher levels of hAChE-I4/E5 in muscle displayed similarly higher AChE in milk. Another line, with 450-fold transgenic hAChE-I4/E5 levels in muscle, revealed increases of up to 235-fold higher than control amounts of milk. Non-denaturing gel electrophoresis followed by cytochemical staining demonstrated a complex migration pattern with a pronounced band co-migrating with hAChE-I4/E5 produced in *Xenopus* oocytes. In contrast, both control mice and transgenics expressing active hAChE-E6 displayed BuChE as the predominant cholinesterase and hydrolysed only 35 nmol ATCh/minute/ml milk. Iso OMPA (10 M$\mu$) inhibited over 80% of this activity. Transgenics expressing hInAChE-E6 displayed considerably lower levels of BuChE in milk, suggesting competitive inhibition of host ChE production. Altogether the transgenic enzyme reached higher concentrations than the 50 nM cholinesterases present in normal human blood. These findings present transgenic models for studying the secretion, control of production and biochemical properties of cholinesterases in mammalian milk.

Figure 33:
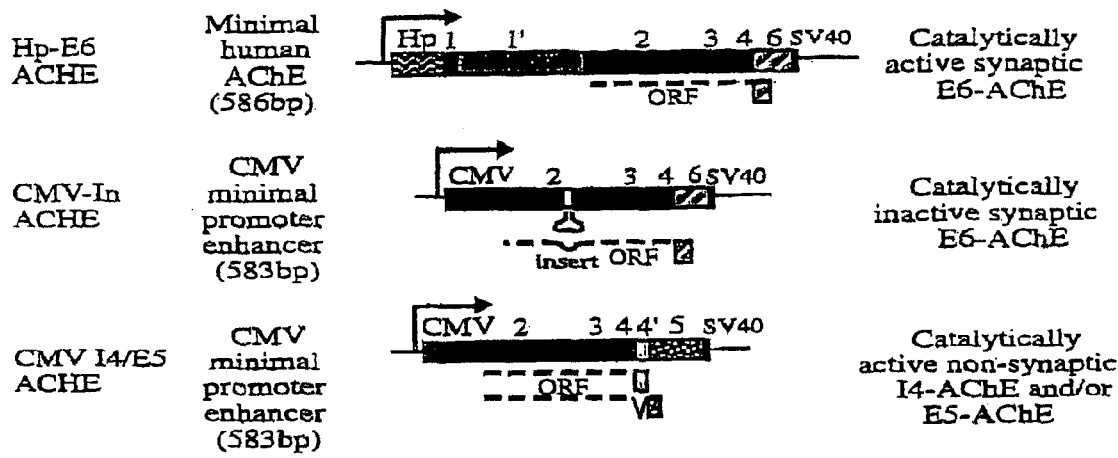
FIGS. 33A–C shows three Human AChE constructs overexpressing various AChE forms in transgenic mice models, arrows indicate the orientation of transcription and exons 1–6 are numbered.

(a) Constructs. Three constructs were used which encode for different isoforms of recombinant AChE which are shown in FIGS. 33A–C, these are as follows:

1. The synaptic AChE isoform containing the exon number 6 derived C-terminus and expressed under control of the human AChE minimal promoter (Beeri et al., 1995, 1997);

2. The synaptic insert inactivated AChE form expressed under control of cytomegalovirus (CMV) promoter. A synthetic 21 bp insert in exon 2 adds seven amino acids to the active site domain creating a catalytically inactive enzyme (Sternfeld et al., 1998);

3. The "readthrough" AChE (I4/E5) with a CMV promoter, pseudointron 4 and exon 5 at its 3'-end. Pseudointron 4 includes an open reading frame terminated by a stop codon. Therefore, without splicing of this pseudointron (I4) the protein product will be terminated by a C-terminus translated from the 5' region of I4. In case of I4 splicing, the protein product will include a C-terminus translated from exon number 5.

Arrows indicate the orientation of transcription and exons one through six are numbered. Intron I1 and pseudointron I4 are hyphenated and the open reading frame of each coding region is noted by a dashed line below it, with the naturally variable C-terminal peptides and the engineered inactivating insert highlighted.

Figure 34:
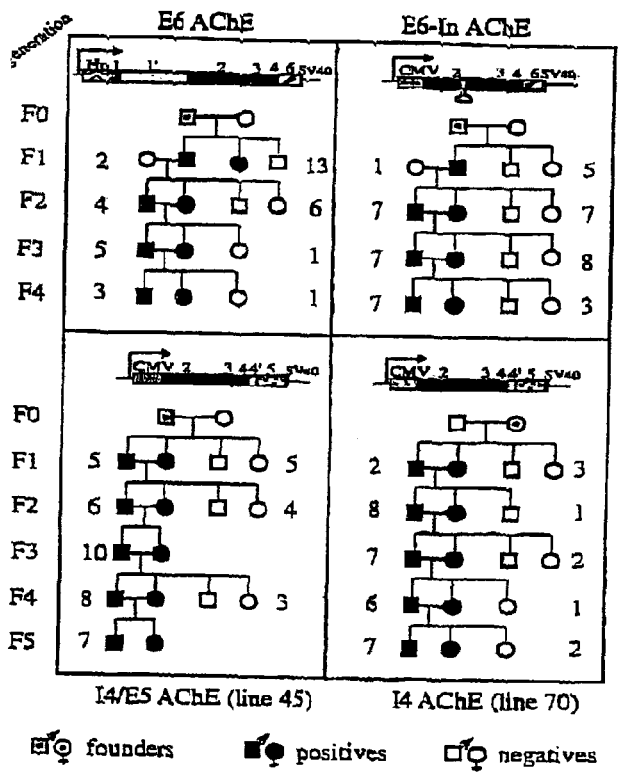
FIG. 34 shows the Mendelian inheritance of transgenic AChE variants in mouse pedigrees.

(b) Pedigree data. Presented in FIG. 34 are pedigree data for four distinct lines of mice carrying the noted transgenic AChE constructs. Transgene presence was determined by PCR amplification from tail DNA samples as detailed in Beeri et al., 1995. Numbers of positive and negative mice in each litter are noted on the left and (c) right respectively. There was an increase in positive litter mates within advanced generations, reflecting unimpaired Mendelian inheritance.

Figure 35:
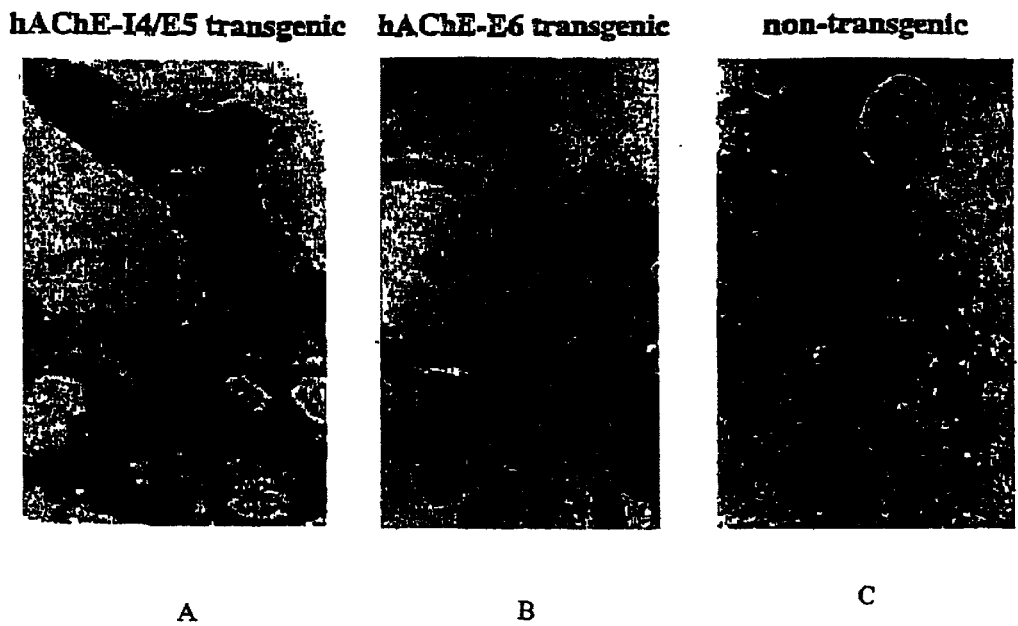
FIGS. 35A–C show the expression of transgenic "readthrough" AChE mRNA transcipts in lactating alveoli from the mouse mammary gland; (A) shows the hAChE-I4/E5 transgenic (Seq. ID 28); (B) shows the hAChE-E6 transgenic (Seq. ID 28); and (C) shows the non-transgenic.

(d) In situ hybridization. In situ hybridization was performed as described in Andres et al., 1997, on 5 μm sections of mammary gland alveoli from lactating transgenic mice expressing the "readthrough" AChE (I4) isoform (FIG. 35A) or the synaptic HpAChE (E6) isoform (FIG. 35B), as compared to non transgenic FVB/N mice (FIG. 35C).

5'-biotinylated 2-O-methyl cRNA directed to a 50 nucleotide-long sequence of pseudointron 4 in AChE mRNA was used as a probe. Fast-red chromogenic substrate was used for detection. Note that the staining intensity of I4mRNA in the mammary gland alveoli of the "readthrough"-AChE transgenic mouse (FIG. 35A) is markedly higher than that of the mouse expressing synaptic AChE (E6) transgenic mouse (FIG. 35B) and the non-transgenic mouse (FIG. 35C). Hybridization signals in mice (FIGS. 35B and C) reflect the endogenous mouse AChE-I4mRNA. Sections treated without probe or with the cRNA probe directed to exon 5 showing no alveoli staining.

Figure 36:
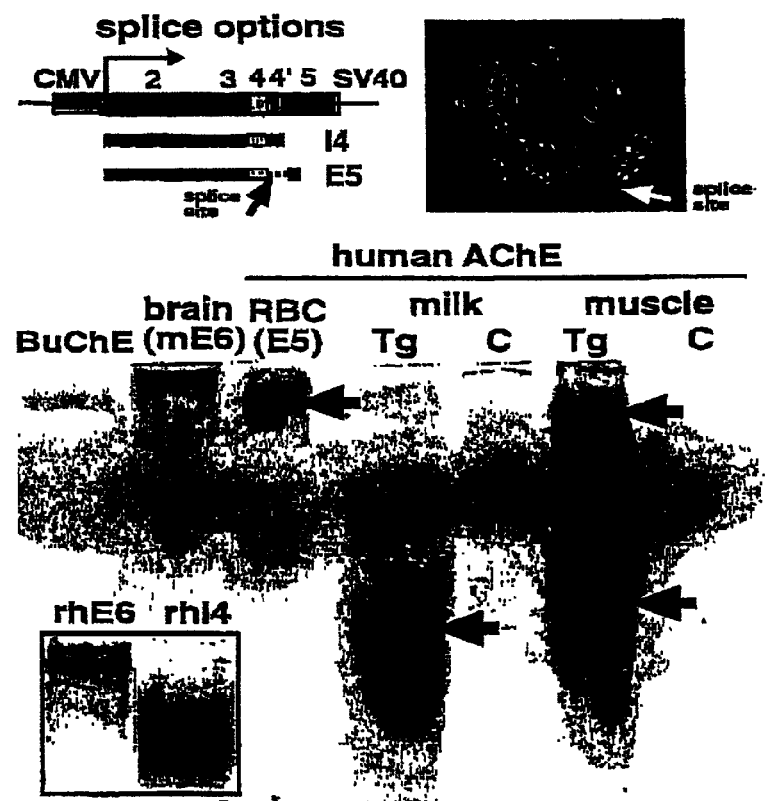
FIG. 36 shows that h-I4/E5 AChE transgenic mice overproduce distinct AChE variants in muscle and milk.

(d) h-I4/E5 AChE transgenic mice overproduce distinct AChE variants in muscle and milk. Loaded extracts were (FIG. 36 left to right): 1. Human BuChE purified from serum; 2. Mouse brain extract expressing the synaptic form of AChE (E6); 3. Purified amphiphilic form of red blood cell (RBC) E5 AChE; 4 and 5. Milk from I4/E5 AChE transgenic and control mice; and 6 and 7. Muscle extract from I4/E5 AChE transgenic and control mice. Samples were electrophoresed in 7% non-denaturing polyacrylamide gels containing 1% Triton X100. Catalytically active ChEs were stained, using the Karnovsky method (Seidman et al., 1995). Upper bands (red arrows) denote E5 AChE. Lower bands (blue arrows) denote I4 AChE. The distinct migration distances are probably due to different glycosylation patterns. The inset of FIG. 36 depicts the electrophoretic migration patterns of recombinant human E6 AChE and I4 AChE produced in *Xenopus* oocytes.

Figure 37:
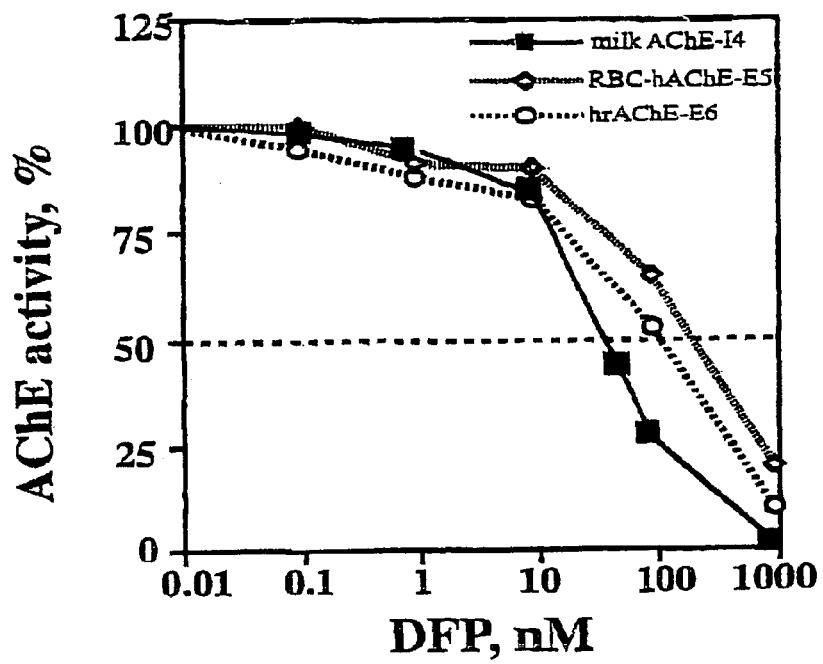
FIG. 37 is a graph showing that hI4AChE is highly sensitive to DFP.

(e) hI4AChE is highly sensitive to DFP FIG. 37). Milk AChE from I4/E5 transgenic mice, human red blood cells (RBC-hAChE-E5) and human recombinant AChE (hr AChE-E6) was pre-incubated with the noted concentrations of diisopropylphosphorofluoridate (DFP) for 20 minutes at pH 7.4 in Ellman's reagent. Acetylthiocholine (1 mM) was added and its hydrolysis rate was determined spectrophotometrically as described in Table VII. Data are presented for each AChE as percent activity of the control (minus DFP). Standard deviation at each DFP concentration was never more than 4% of the control. Note that AChE from I4/E5-AChE transgenic mice milk is more sensitive (IC50=60 nM DFP) than RBC-hAChE-E5 (IC=130 nM DFP and hrAChE-E6 (IC=110 nM DFP).

Figure 38:
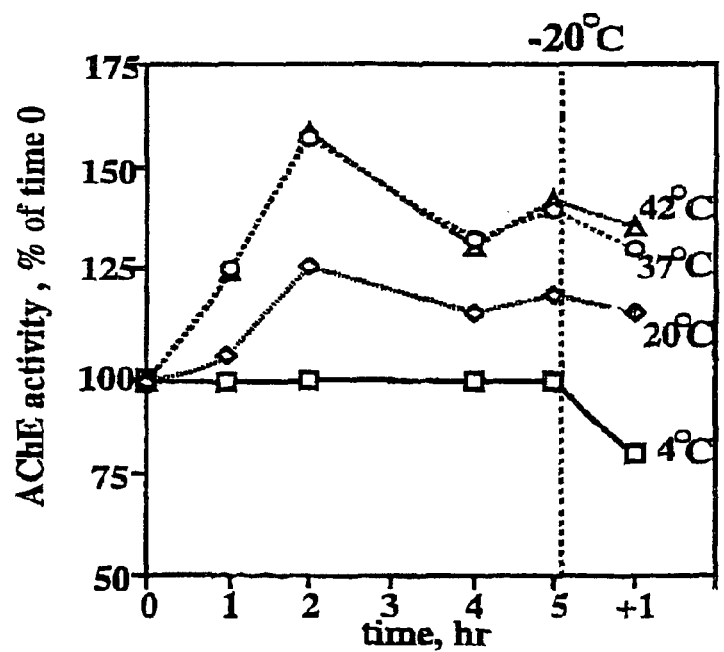
FIG. 38 shows graphically the heat stability of transgenic human AChE in milk from I4-AChE transgenic mice.

(f) Heat stability. Presented in FIG. 38 are AChE activity levels in milk from I4-AChE transgenic mice following five hours incubation at 4, 20, 37 and 42° C. After five hours all samples were frozen at 20° C. for one hour, following which period AChE activity was re-measured. AChE activity patterns were similar at 37 and 42° C. Activity elevations during the first two hours of incubation at >20° C. reveal thermostable properties at mammalian body temperature.

Throughout this application various publications are referenced. Full citations for the publications referenced are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

Expression of Alternative AChEmRNA Transcripts in Different Tumor Cell Types

| | | AChEmRNA Transcripts | | | Other mRNAs | |
|---|---|---|---|---|---|---|
| | (2) | (3) E5 | (4) Read- | (5) | (6) | (7) |
| (1) Source Exons: | Major E3,E4,E6 | transcript E3,E4,E5 | through E3,E4,I4 | 3'Conn E5,E6 | BChE | CHED |
| Teratocarcinoma (NT2/D1) | $10^6$ | +++ | +++ | ++ | — | $10^6$ |
| T Cell Lynphoma (H9) | – | – | – | – | $10^4$–$10^5$ | $10^5$ |
| Neuroblastoma (IMR 32) | $10^5$–$10^6$ | – | – | – | $10^5$ | $10^6$ |
| Transformed Embronal Kidney Cells (293) | $10^5$–$10^6$ | ± | ± | ± | — | $10^5$ |
| Small cell lung Ca (NCI N 592) | $10^6$ | + | + | ± | $10^5$ | $10^6$ |
| Medulloblastoma (TE 671) | $10^6$ | + | ± | ± | $10^5$ | $10^6$ |
| Chronic Myelogenous Leukemia K 562 | ++ | + | n.d. | n.d. | n.d. | n.d. |
| Promegakaryoblastic-D AMI | $10^5$–$10^6$ | – | – | — | — | |
| Serous ovarian Ca. | ++ | – | – | – | n.d. | n.d. |

TABLE 1-continued

Expression of Alternative AChEmRNA Transcripts in Different Tumor Cell Types

| (1) Source Exons: | AChEmRNA Transcripts | | | | Other mRNAs | |
|---|---|---|---|---|---|---|
| | (2) Major E3,E4,E6 | (3) E5 transcript E3,E4,E5 | (4) Read-through E3,E4,I4 | (5) 3'Conn E5,E6 | (6) BChE | (7) CHED |
| Moucinous cyst adenoma | ++ | – | – | – | n.d. | n.d. |
| Papillary adenocarcinoma | ± | – | – | – | n.d. | n.d. |
| Uterine myoma | +++ | – | – | – | n.d. | n.d. |
| Fetal brain (21 W) | $10^6$ | – | n.d. | n.d. | $10^3$ | $10^5$ |
| Adult brain (70 Y) | $10^5$ | – | n.d. | n.d. | $10^2$–$10^3$ | $10^4$ |
| Adipose tissue | ± | – | – | – | n.d. | n.d. | n.d.: not determined

In Table I, the meanings of (1)–(7) are as follows:

(1) RNA was extracted from cultured cells, tumor biopsies and normal tissues as detailed herein above. Samples of 100 ng total RNA were subjected to RNA-PCR amplification with the noted primer pairs.

(2) Major AChEmRNA transcripts containing E3, E4 and E6 (FIGS. 1 and 2) were detected by the primer pair 1,2.

(3) E5 containing AChEmRNA was searched for using the primer pair 1,3 detecting transcripts including the E3-E4-E5 regions.

(4) Readthrough AChEmRNA was found with primers 1,4, detecting transcripts containing the E3, E4 and I4 regions.

(5) The 3'-connection of alternative AChEmRNA transcripts was examined by the primer pair 2,5, checking for the presence of the E6 exon in E5 containing mRNAs. (6,7) BChE (Prody et al., 1987) and CHED (Lapidot-Lifson et al., 1992) transcripts were amplified to account for the integrity of the examined RNA preparations. Presented are copy numbers calculated for each transcript based on comparison with in vitro transcribed, deleted RNAs from each of the analyzed genes. Visual estimation of AChEmRNA levels based on the intensity of PCR products at 39 cycles is presented, in decreasing order, as +++ (>$10^6$), ++ ($10^5$–$10^6$), + ($10^4$–$10^5$)±(ca. $10^4$), – (<$10^4$ n.d.).

TABLE II

Subcellular Fractionation of rHAChE in CMVAChE-injected Xenopus Embryos

| FRACTION | rH DAY 1 | DAY 2 | DAY 3 | Fr DAY 3 |
|---|---|---|---|---|
| LSS | 57 ± 2 | 60 ± 4 | 53 ± 3 | 36 ± 5 |
| DS | 37 ± 2 | 34 ± 4 | 36 ± 3 | 31 ± 4 |
| HSS | 6 ± 2 | 5 ± 1 | 10 ± 1 | 33 ± 7 |

TABLE III

Overexpression of AChE in 3 days NMJ

| EXP. | Post-Synaptic Length (PSL), μm | Stained Length (SL), μm | SL/PSL, ratio | Stained Area (SA), μm² |
|---|---|---|---|---|
| Umnj. | 2.57 | 0.79 | 0.004 | 0.156 |
| | 3.95 | 0.79 | 0.200 | 0.126 |

TABLE III-continued

Overexpression of AChE in 3 days NMJ

| EXP. | Post-Snyaptic Length (PSL), μm | Stained Length (SL), μm | SL/PSL, ratio | Stained Area (SA), μm² |
|---|---|---|---|---|
| | 1.54 | 0.80 | 0.060 | 0.080 |
| | 2.35 | 0.73 | 0.310 | 0.082 |
| | 1.17 | 0.44 | 0.085 | 0.063 |
| | 1.60 | 0.29 | 0.180 | 0.056 |
| | 1.02 | 0.29 | 0.280 | 0.040 |
| | 0.88 | 0.58 | 0.650 | 0.075 |
| Av. ± SD | 1.88 ± 0.93 | 0.58 ± 0.22 | 0.22 ± 0.19 | 0.084 ± 0.038 |
| CMVAChE | 1.76 | 1.17 | 0.660 | 0.284 |
| | 2.50 | 2.05 | 0.820 | 0.331 |
| | 2.64 | 1.91 | 0.720 | 0.285 |
| | 2.50 | 2.40 | 0.960 | 0.476 |
| | 3.50 | 2.03 | 0.580 | 0.396 |
| | 1.85 | 1.66 | 0.900 | 0.333 |
| | 3.10 | 1.85 | 0.600 | 0.535 |
| | 3.23 | 1.76 | 0.540 | 0.289 |
| Av. ± SD | 2.64 ± 0.58 | 1.85 ± 0.33 | 0.72 ± 0.15 | 0.37 ± 0.09 |
| P value | P < 0.01 | P < 0.002 | P < 0.002 | P < 0.002 |

TABLE IV

Immunoadsorption of Catalytically Active Human AChE Produced in the Brain of Transgenic Mice

| Homogenate None | Control Mouse | 12F2-σ1 | 13F2-σ10 | Recombin. HAChE |
|---|---|---|---|---|
| ATCH hydrolysis 0.573 mOD/min 0.557 | 0.947 | 1.270 | 3.967 | 16.15 |
| | 0.947 | 1.160 | 4.397 | 4.397 |

TABLE V

Altered Differential Cell Counts in the Bone Marrow of Transgenic Mice

| Mice | Age | Lymphocytes % | Myoblasts % | Granniocytes % | Losinophils % | Erythroblast Normoblasts % | Copy No. | Cells |
|---|---|---|---|---|---|---|---|---|
| C1 (m) | | 20.0 | 23.66 | 38.66 | 0.66 | 17.33 | — | 300 |
| C2 (f) | | 24.0 | 27.66 | 35.66 | 0 | 12.33 | — | 800 |
| C3 (m) | 7w | 11.1 | 33.1 | 26.0 | 0.4 | 29.4 | — | 950 |
| C4 (f) | 7w | 6.6 | 41.2 | 24.3 | 0.7 | 27.2 | — | 800 |
| C5 (f) | | 16.7 | 30.00 | 34.00 | 1.66 | 17.66 | — | 300 |
| C6 (f) | 3.5 m | 19.66 | 32.66 | 24.5 | 0.5 | 23.16 | | |
| C7 | | 9 | 35.0 | 24.5 | 2.0 | 29.5 | | |
| #1.5 [fo, f] | 8 m | 12.0 | 35.66 | 19.66 | 0.33 | 32.33 | 2 | 300 |
| 13-2 [Fl, m] | 7w | 27.8 | 37.9 | 1.0 | 0 | 33.3 | 2 | 800 |
| #13-10 [Fli, f] | 7–8 w | 11.33 | 35.33 | 27.0 | 2.0 | 23.66 | 2 | 300 |
| #8 [Fu, m] | 5.5 m | 17.0 | 24.33 | 26.66 | 0.66 | 31.33 | 1 | 300 |
| #12-1 [FH, f] | 7–8 w | 24.0 | 21.66 | 30.33 | 1.66 | 25.33 | 15 | 300 |
| #8-8 [FIL, m] | 11–12 w | | | | | | | 1 |
| #13-11 [FII, f]p | | | | | | | | 2 |
| #12-2 [FII, f]p | 12 w | 23.5 | 24.5 | 18.5 | 0 | 33.0 | 15 | |
| #13-4 [FIL, f] | 3 m | 14.0 | 32.5 | 15.5 | 10.5 | 27.5 | 2 | |
| #12-6 [FII, m] | 8 w | 14.0 | 360.0 | 23.5 | 2 | 24.5 | 15 | |
| Average Normal Range Theoretical | | 12–20 | 25–35 | 35–45 | 0.5–2.5 | 18.25 | | |

***(f = female; m = male; p = pregnant; w = weeks; m = months)
Differential cell counts were determined in percentage by observing cell shape, size and histochemical staining for each of the noted mice. Note distinct variations in differential cell compositions of the transgenic mice as compared with controls.

TABLE VI

Altered CFC-GEMM Colonies from AChE Transgenic Mice

| No. & Treatment | Colony Counts | Cell No. | Mφ | PMN | E Megs | Ltd. Megs | E RBC | Lt. RBC | Total Cells | Exp. No. |
|---|---|---|---|---|---|---|---|---|---|---|
| Ch untreated | | | 16 | 14.9 | 8.1 | 2.4 | 25.5 | 33.1 | 592 | 165 |
| 12F2-1 & 13F | | | 29.1 | 40.4 | 3.9 | 1.9 | 13.2 | 11.6 | 1269 | |
| 2 10 C7 un. | 16 | | 42.3 | 26.4 | 9.2 | 7 | 9.2 | 5.7 | 277 | 170 |
| 12f3-6 un. | 8 | | 37.6 | 26.0 | 8.9 | 1.7 | 20.7 | 5.1 | 651 | |
| C7s | 7 | | | | | | | | | |
| 12F3-6S | 7 | | | | | | | | | |
| C7 AS | 13 | | 76.7 | 13.6 | 3.3 | 1.6 | 1.9 | 2.9 | 696 | |
| 12F3-6 AS | 7 | | 14.5 | 41.9 | 4.6 | 9.9 | 14.5 | 14.5 | 344 | |
| C8 un. | 51 | 8.3 × 10⁵ | 28.2 | 16.9 | 3.9 | 3.5 | 18.2 | 27.3 | 710 | 173 |
| F312-2 un | 26 | 3.4 × 10⁵ | 21.7 | 38.3 | 9.5 | 4.2 | 14.4 | 11.9 | 494 | |
| C8 s. | 23 | 2.9 × 10⁵ | 47.8 | 25.7 | 8.3 | 6.5 | 6.6 | 5.1 | 626 | |
| 13F3-2 s | 17 | 3.1 × 10⁵ | 50.7 | 29.4 | 8.4 | 3.3 | 6.0 | 2.1 | 629 | |
| C8 AS | 123 | 13.8 × 10⁵ | 69.2 | 11.4 | 8.0 | 7.8 | 2.1 | 1.5 | 812 | |
| 12F3-2 AS | 101 | 8.2 × 10⁵ | 63.7 | 17.8 | 6.0 | 5.8 | 4.4 | 1.8 | 886 | |

Note 50% of control colony number in the transgenic mice and in exp. 173 - correction by the A5 oligo.

TABLE I

Overexpression of human AChE in various transgenic mice

| | Total | $+10^{-5}$ M Iso-OMPA | Percent of control | Total | $+10^{-5}$ M Iso-OMPA | Percent of control | Total | $+10^{-5}$ M Iso-OMPA | Percent of control |
|---|---|---|---|---|---|---|---|---|---|
| CMVE6-In AChE | 24 ± 13 | 22 ± 0.7 | 115 | 1.59 ± 0.3 | 1.59 ± 0.3 | 167 | 1.2 ± 0.4 | 0.04 ± 0.01 | 8 |
| CMVI4/E5-AChE (line 45) | 32 ± 22 | 31 ± 0.7 | 163 | 42 ± 4.8 | 42 ± 5.1 | 4420 | 11 ± 1.1 | 7.4 ± 0.3 | 1510 |
| CMVI4/E5-AChE (line 70) | 26 ± 25 | 26 ± 2.8 | 136 | 434 ± 40 | 433 ± 40 | 45580 | 121 ± 4.4 | 115 ± 3.5 | 23500 |
| FVB/N control (non transgenic) | 20 ± 17 | 19 ± 1.7 | 100 | 0.9 ± 0.06 | 0.95 ± 0.06 | 100 | 4.1 ± 0.4 | 0.49 ± 0.3 | 100 |

Hydrolysis rates of acetylthiocholine (ATCH) were determined spectrophotometrically using a modification of Ellman's assay (Andres et al., 1997), in the presence or absence of 10 M of the selective BuChE inhibitor iso-OMPA (tetraisopropylpyrophosphoramide). Whole brain and striated muscle extracts were obtained as described previously (Beeri et al. 1995). Milk was collected from nursing mice seven days after parturition.

Note the pronounced high activety of AChE in muscle and milk in the two lines of the I4/E5-AchE transgenic mice (up to 450-fold in muscle and 235-fold in milk compared to non-transgenice mice). In contrast, brain AChE levels remained within a range of 1.6-fold over control. In the milk on non-transgenic mice and transgenics expressing inactive AChE most of the ChE activity is contributed by butyrylchlinesterase, which is exeedingly low in brain and muscle of all lines.

REFERENCES

Andres, C., Beeri, R., Friedman, A., Lev-Lehman, E., Henis, S., Timberg, R., Shani, M., Soreq, H. (1997) Acetylcholinesterase-transgenic mice display embryonic moduations in spinal cord choline acetyltransferase and neurexin I gene expression followed by late-onset neuromotor degeneration. Proc. Natl. Acad. Sci. USA 95, 8173–8178.

Andrews (1988) *Biochem. Biophys. Acta* 948:17–36.

Anglister and McMahan (1985). "Basal lamina directs acetylcholinesterase accumulation at synaptic sites in regenerating muscle", *J. Cell Biol.* 101:735–743.

Bartels et al. (1993) *Am. J. Hum. Genet.* 52:928–936.

Beeri, R., Andres, C., Lev-Lehman, E., Timberg, R., Huberman, T., Shani, M. and Soreq, H. (1995) Transgenic expression of human acetylcholinesterase induces progressive cognitive deterioration in mice. Curr. Biol., 5, 1063–1071.

Beeri, R., LeNovere, N., Mervis, R., Huberman, T. Grauer, E., Changeux, J. P. and Soreq, H. (1997) Enchanced hemicholinium binding and attenuated dendrite branching in cognitively impaired ACHE-transgenic mice. J. Neurochem, 69, 2441–2451.

Ben Aziz-Aloya et al., (1993). "Expression of a human acetylcholinesterase promoter-reporter construct in developing neuromuscular junctions of *Xenopus* embryos", *Proc. Natl. Acad. Sci. USA*, 90:2471–2475.

Betz et al., 1994, in Basic Neurochem. Molecular Cell, (Raven Press Ltd, NY) 5th Ed., 681–699.

Billett and Gould, (1971). "Fine ultrastructural changes in the differentiating epidermis of *Xenopus laevis* embryos", *J. Anat.*, 108, 465–480.

Blackwell et al.(1991) *Science* 250:1149–1152.

Brodbeck and Liao (1992) "Subunit assembly and glycosylation of acetylcholinesterase from mammalian brain", in *Multidisciplinary approaches to Cholinesterase Functions* (Shafferman and Velan, eds.), pp. 33–38. Plenum Press, New York.

Chen et al., J. Neurotrauma 13:557.

Clement, J. G. (1991) "Hypothermia: limited tolerance to repeated soman administration and cross-tolerance to oxothreomorine" *Biochem. Behav.* 39, 929–934.

Coyle et al. (1983) *Science* 219, 1186–1189.

Drews (1975) "Cholinesterase in embryonic development", *Prog. Histochem. Cytochem* 7:1–52.

Duval, et al. (1992) "H and T subunits of acetylcholinesterase from Torpedo, expressed in COS cells, generate all types of molecular forms" *J. Cell. Biol.*, 118, 641–653.

Fitzpatrick-McElligot and Stent (1981) "Appearance and localization of acetylcholinesterase in embryo of the leech *Helodbella Triserialis"*, *J. Neurosci.* 1:901–907.

Fournier et al. (1992) "*Drosophila* acetlycholinesterase: Expression of a functional precursor in *Xenopus* oocytes" *Eur. J. Biochem.* 203, 513–519.

Fuentes and Taylor (1993) "Control of acetylcholinesterase gene expression during myogensis" *Neuron.* 10, 379–387.

Gibney and Taylor (1990) *J. Biol. Chem.* 265:12576–12583.

Gennari and Brodbeck (1985) "Molecular forms of acetylcholinesterase from human caudate nucleus, Comparison of salt-soluble and detergent-soluble tetrameric enzyme species", *J. Neurochem.* 44:697–704.

Gnatt et al. (1990) *Cancer Res.* 50:1983–1987.

Greenberg et al. (1988) *Blood* 72:1968–1977.

Grisaru et al., MCR 19.788.

Inestrosa et al. (1987) *J. Biol. Chem.* 262:4441–4444.

Jasmin et al. (1993) "Compartmentalization of acetylcholinesterase mRNA and enzyme at the vertebrate neuromuscular junction" *Neuron.* 11, 467–477.

Jennekens et al. (1992) "Deficiency of acetylcholine receptors in a case of end-plate acetylcholinesterase deficiency: A histochemical investigation", *Muscle and Nerve* 15:63–72.

Karpel et al. (1994) *Exptl. Cell. Res.* 210, 268–277.

Karnovsky (1964) "The localization of cholinesterase activity in rat cardiac muscle by electron microscope" *J. Cell Biol.* 23:217–232.

Knapp et al. (1994) "A 30-week randomized controlled trial of high-dose tacrine in patients with Alzhemier's disease" *J. Am. Med. Assn.* 271:985–991.

Krejci et al. (1991) "Primary structure of a collagenic tail peptide of Torpedo acetylcholinesterase: co-expression with catalytic subunit induces the production of collagen-tailed forms in transfected cells", *EMBO J.* 10:1285–1293.

Kronman et al. (1992) "Production and secretion of high levels of recombinant human acetylcholinesterase in cultured cell lines: microheterogeneity of the catalytic subunit", *Gene* 121:295–304.

Lapidot-Lifson et al. (1992) "Cloning and antisense oligodeoxynucleotide inhibition of a human homolog of cdc2 required in hematopoiesis", *Proc. Natl. Acad. Sci. USA* 89: 579–583.

Lapidot-Lifson et al. (1989) "Co-amplification of human acetylcholinesterase and butyrylcholinesterase in blood cells: Correlation with various leukemias and abnormal megakaryocytopoiesis" *Proc. Natl. Acad. Sci. USA* 86: 4715–4717.

Legay et al. (1993a) Cloning and expression of a rat acetylcholinesterase subunit: generation of multiple molecular forms, complementarity with a Torpedo collagenic subunit", *J. Neurochem.* 60:337–346.

Legay et al. (1993b) *FEBS Lett* 315:163–166.

Lev-Lehman et al. (1993) "Antisense inhibition of acetylcholinesterase gene expression causes transient hematopoietic alterations in vivo", *Gene Therapy*, 1:1–11.

Li et al. (1991) "Gene structure of mammalian acetylcholinesterase: Alternative exons dictate tissue specific expression" *J. Biol. Chem.* 266:23083–23090.

Li et al. (1993) *J. Biol. Chem.* 268, 5790–97.

Liao et al. (1992) "Different glycosylation in acetylcholinesterase from mammalian brain and erythrocytes", *J. Neurochem.* 58:1230–1238.

Loewenstein et al. (1993) "Molecular dissection of cholinesterase domains responsible for carbamate toxicity" *Chem. Biol. Interactions* 87:209–216.

Low (1987) *J. Biochem.* 244:1–13.

Massoulie et al. (1992) (Shafferman and Velan, eds., Plenum Press, N.Y.) pp. 285–288.

Massoulie et al. (1993) "Molecular and cellular biology of cholinesterases" Progress in *Neurobiology* 41, 31–91.

Maxwell, D. M.; Brecht, K. M., Doctor, B. P., Wolfe, A. D. (1993) Comparison of antidote protection against soman by pyridostigmine, H1–6 and acetylcholinesterase. J. Pharmacol. Exp. Ther. 164, 1085–1089.

Meneely et al. (1989) "Effects of the organophosphate insecticides Diazinon and Parathion on bobwhite quail embryos: skeletal defects and acetylcholinesterase activity" *J. Exp. Zool.* 252:60–70.

Millard and Broomfield (In press, 1995) "Biology of Cholinesterase Inhibitors", *J. Neurochem.*

Navaratnam (1991) *Lancet* 337:447–450.

Neville et al. (1992) "Intra-molecular relationships in cholinesterases revealed by oocyte expression of site-directed and natural variants of human BChE", *EMBO J.* 11:1641–1649.

Newhouse et al. (1994) *Drug. Dev. Res.* 31, 71–79.

Nishikawa and Sasaki (1993) "Secretion of chondroitin sulfate from embryonic epidermal cells in *Xenopus laevis*" *J. Histochem. Cytochem.* 9, 1373–1381.

Pardridge, et al., (1992) *West J. Med.* 156(3) 281–286.

Pardridge, (1992) *Pharm. Toxicol.* 71(1):3–10.

Pardridge, et al., (1993) *Proc. Natl. Acad. Sci. USA* 90(7) 2618–2622.

Patinkin et al. (1990) Manipulations of cholinesterase gene expression modulate murine megakaryocytopoiesis in vitro" *Mol. Cell. Biol.* 10:6046–6050.

Paoletti et al. (1992) "Acetylcholinesterase in murine erythroleukemia (Friend) cells: evidence for megakaryocyte-like expression and potential growth-regulatory role of enzyme activity", *Blood* 79:2873–2879.

Pavlath et al. (1989) "Localization of muscle gene products in nuclear domains" *Nature* 337, 570–573.

Plump et al. (1992) "ApoE-deficient mice have been created by homologous recombination in E5 cells", *Cell* 71:343–353.

Pressman-Schwartz et al. (1992) "A 69-kDa RNA-binding protein from *Xenopus* oocytes recognizes a common motif in two vegetally localized maternal mRNAs" *Proc. Natl. Acad. Sci. USA* 89, 11895–11899.

Prody et al. (1987) "Isolation and charaterization of full-length cDNA clones coding for cholinesterase from fetal human tissue" *Proc. Natl. Acad. Sci. USA* 84:3555–3559.

Ralston and Hall (1989) "Transfer of a protein encoded by a single nucleus to nearby nuclei in multinucleated mytobes" *Nature* 244, 1066–1069.

Raveh, L., Grauer, E., Grunwald, J., Cohen, E., Ashani, Y. (1997) The stoichiometry of protection against soman and VX toxicity in monkeys pretreated with human butyrylcholinesterase. Toxicol. Appl. Pharmacol. 145, 45–53.

Roberts et al. (1991) *Biol Chem.* 266:7481–7487.

Rubinstein et al. (1984) *Biochem Gen* 22:1171–1175.

Salpeter (1967) "Electron microscope radioautography as a quantitative tool in enzyme cyotchemistry I: The distribution of acetylcholinesterase at motor endplates of a vertebrate twitch muscle" *J. Cell. Biol.* 32, 379–389.

Schmidt et al., (1990) "The cytomegalovirus enhancer: a panactive control element in transgenic mice" *Molec. Cell. Biol.* 10, 4406–4411.

Seidman et al. (1994) "Overexpressed monomeric human acetylcholinesterase induces subtle ultrastructural modifications in developing meuromuscular junctions of *Xenopus laevis* embryos" J. Neurochem. 62, 1670–1681.

Seidman, S., Sternfeld, M., Ben Aziz-Aloya, R., Timberg, R., Kaufer-Nachum, D., Soreq, H. (1995) Synaptic and epidermal accumulation of human acetylcholinesterase are encoded by alternative 3-terminal exons. Mol. Cell Biol. 15, 2993–3002.

Shani (1985) "Tissue specific expression of rat myosin light chain 3 gene in transgenic mice", *Nature* 314:283–286.

Sher et al. (1990) *Cancer Res.* 50:3892–3896.

Sikorav et al. (1988) "Complex alternative splicing of acetylcholinesterase transcripts in Torpedo electric organ: primary structure of the precursor of the glycolipid-anchored dimeric form" *EMBO J.* 7, 2983–2993.

Sokol et al. (1991) "Injected Wnt RNA induces a complete body axis in *Xenopus* embryos", *Cell* 67:741–752.

Soreq et al. (1990) "Molecular cloning and construction of the coding region for human acetylcholinesterase reveals a G,C rich attenuating structure", *Proc. Natl. Acad. Sci. USA* 87:9688–9692.

Soreq et al. (1991) *Cancer Cells* 3:511–516.

Soreq et al. (1989) "Expression and tissue specific assembly of cloned human butyrylcholine esterase in microinjected *Xenopus laevis* oocytes" *J. Biol. Chem.* 264:10608–10613.

Soreq and Zakut (1993) "Human Cholinesterases and anticholinesterases", Academic Press.

Sternfeld, M., Ming, G-L., Song, H-J., Sela, K., Timberg, R., Poo, M-M and Soreq, H. (1998) Acetylcholinesterase enchances neurite growth and synapse development through alternate contributions of its hydrolytic capacity, core protein and variable C-termini. J. Neurosci., 18, 1240–1249.

Toutant et al. (1990) *Euro J. Biochem.* 187:31–38.

Velan et al. (1991a) "Recombinant human acetylcholinesterase is secreted from transiently transfected 293 cells as a soluble globular enzyme," *Cell. Mol. Neurobiol.* 11:143–156.

Velan et al. (1991b) "The effect of elimination of intersubunit disulfide bonds on the activity, assembly and secretion of recombinant human acetylcholinesterase", *J. Biol. Chem.* 266:23977–23984.

Wolfe, A. D., Blick, D. W., Murphy, M. R., Miller, S. A., Gentry, M. K., Hartgraves, S. L., Doctor, B. P. (1992) Use of cholinesterases as pretreatment drugs for the protection of rhesus monkeys against soman toxicity. Toxicol. Appl. Pharmacol. 117, 189–193.

Wurtman (1992) *TINS* 5, 117–112.

Zakut et al. (1990) "Acetylcholinesterase and butyrylcholinesterase genes coamplify in primary ovarian carcinomas" *J. Clin. Invest.* 86:900–908.

Zakut et al. (1991) *Cancer* 61:727–737.

Zakut et al. (1992) "In vivo gene amplification in non-carcerous cells; cholinesterase genes and oncogenes amplify in throbocytopernia associated with Lupus Erythematosus" *Mutation Research* 276:275–284.

Zakut et al. (1991) "Chorionic villus cDNA library displays expression of butyrylcholinesterase: putative disposition for ecological danger", *Prenatal Diagnosis* 11:597–607.

Zon et al. (1991) "Expression of GATA-binding proteins during embryonic development in *Xenopus laevis*" *Proc. Natl. Acad. Sci. USA* 88, 10642–10646.

What is claimed is:

1. A transgenic non-human mammal whose genome comprises a recombinant nucleic acid expression vector encoding a heterologous cholinesterase positioned under the regulatory control of a promoter functional in the mammary gland of the transgenic non-human mammal, said heterologous cholinesterase selected from the group consisting of:

(a) wild-type human AChE;
   (b) wild-type human BChE;
   (c) variants of (a) and (b) having cholinesterase activity; and
   (d) wild-type insect ChEs, wherein said heterologous cholinesterase is expressed in milk of said nonhuman mammal in detectable quantities.

2. The transgenic non-human animal of claim 1, wherein the animal is *Xenopus* or mammal.

3. The transgenic non-human mammal of claim 1, wherein the recombinant expression vector comprises a nucleic acid encoding a human AChE or a variant thereof having cholinesterase activity, which nucleic acid comprises:

(i) consecutive nucleotides having the nucleic acid sequence set forth in SEQ ID NO: 1 or a fragment thereof;
   (ii) consecutive nucleotides having the nucleic acid sequence set forth in SEQ ID NO: 3 or a fragment thereof; or
   (iii) consecutive nucleotides having the nucleic acid sequence set forth in SEQ ID NO: 5 or a fragment thereof.

4. The transgenic non-human mammal of claim 1, wherein the transgenic non-human mammal is female and wherein said promoter is a mammary gland specific promoter.

5. The transgenic non-human mammal of claim 1, wherein (c) are recombinantly-produced variants having at least one point mutation and/or deletion of one or more nucleotides.

6. The transgenic non-human mammal of claim 1, wherein said mammal is a female goat and said heterologous cholinesterase expressed in said milk of said mammal is wild-type human AChE or BChE or a biologically active variant thereof.

7. The transgenic non-human mammal of claim 4, wherein the mammal is a mouse, a goat, a cow or a pig.

8. A method of producing recombinant cholinesterase comprising the steps of:

(i) inducing lactation in the transgenic non-human female mammal according to claim 4;
   (ii) obtaining milk from the transgenic non-human mammal of step (i); and
   (iii) isolating human cholinesterase from the milk obtained in step (ii), so as to thereby produce recombinant human cholinesterase.

* * * * *